(12) United States Patent
Watabe et al.

(10) Patent No.: US 12,252,496 B2
(45) Date of Patent: Mar. 18, 2025

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satomi Watabe, Kanagawa (JP); Hideko Yoshizumi, Kanagawa (JP); Satoshi Seo, Kanagawa (JP); Hiromitsu Kido, Kanagawa (JP); Toshiki Sasaki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1078 days.

(21) Appl. No.: 17/056,625

(22) PCT Filed: May 21, 2019

(86) PCT No.: PCT/IB2019/054167
§ 371 (c)(1),
(2) Date: Nov. 18, 2020

(87) PCT Pub. No.: WO2019/229584
PCT Pub. Date: Dec. 5, 2019

(65) Prior Publication Data
US 2021/0206775 A1   Jul. 8, 2021

(30) Foreign Application Priority Data
May 31, 2018   (JP) .................................. 2018-104892

(51) Int. Cl.
*H01L 51/50*   (2006.01)
*C07D 491/048*   (2006.01)
(Continued)

(52) U.S. Cl.
CPC ....... *C07D 491/048* (2013.01); *C07D 519/00* (2013.01); *H10K 85/653* (2023.02);
(Continued)

(58) Field of Classification Search
None
See application file for complete search history.

(56) References Cited

U.S. PATENT DOCUMENTS 7,906,226 B2   3/2011   Matsuura et al.
8,105,701 B2   1/2012   Matsuura et al.
(Continued)

FOREIGN PATENT DOCUMENTS

CN   105103327 A   11/2015
CN   106573938 A   4/2017
(Continued)

OTHER PUBLICATIONS

Chinese Office Action (Application No. 201980036561.8) Dated Mar. 31, 2023.
(Continued)

*Primary Examiner* — Gregory D Clark
(74) *Attorney, Agent, or Firm* — Husch Blackwell LLP

(57) ABSTRACT

Provided is a novel organic compound, a benzofuropyrimidine derivative or a benzothienopyrimidine derivative, which is an organic compound represented by General Formula (G1) below.

(Continued)

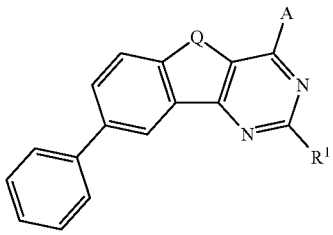

(G1)

In General Formula (G1), Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure.

21 Claims, 30 Drawing Sheets

(51) Int. Cl.
    *C07D 519/00*     (2006.01)
    *H10K 85/60*     (2023.01)
(52) U.S. Cl.
    CPC ....... *H10K 85/654* (2023.02); *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 8,470,455 B2 | 6/2013 | Matsuura et al. | |
| 9,905,782 B2 | 2/2018 | Inoue et al. | |
| 10,193,086 B2 | 1/2019 | Inoue et al. | |
| 10,586,931 B2 | 3/2020 | Kanamoto et al. | |
| 10,700,291 B2 | 6/2020 | Inoue et al. | |
| 10,717,744 B2 | 7/2020 | Park et al. | |
| 10,734,588 B2 | 8/2020 | Park et al. | |
| 10,868,258 B2 | 12/2020 | Kurihara et al. | |
| 11,530,225 B2 | 12/2022 | Kim et al. | |
| 11,600,789 B2 | 3/2023 | Inoue et al. | |
| 2014/0291645 A1* | 10/2014 | Inoue ................. | H10K 85/6574 257/40 |
| 2015/0207082 A1 | 7/2015 | Dyatkin et al. | |
| 2017/0186971 A1* | 6/2017 | Kanamoto ............. | C09K 11/06 |
| 2017/0200903 A1 | 7/2017 | Park et al. | |
| 2018/0141957 A1 | 5/2018 | Park et al. | |
| 2020/0024282 A1 | 1/2020 | Parham et al. | |
| 2020/0055865 A1 | 2/2020 | Kim et al. | |
| 2020/0161564 A1 | 5/2020 | Kim et al. | |
| 2020/0259099 A1 | 8/2020 | Kurihara et al. | |
| 2020/0295267 A1 | 9/2020 | Kanamoto et al. | |

FOREIGN PATENT DOCUMENTS

| | | | | |
|---|---|---|---|---|
| CN | 107428773 | A | 12/2017 | |
| CN | 108431010 | A | 8/2018 | |
| EP | 3 266 787 | A2 | 1/2018 | |
| EP | 3 553 049 | A1 | 10/2019 | |
| JP | 2010-182699 | A | 8/2010 | |
| JP | 2017-119682 | A | 7/2017 | |
| JP | 2018-510148 | | 4/2018 | |
| JP | 2020-505338 | | 2/2020 | |
| KR | 2015-0088176 | A | 7/2015 | |
| KR | 2018-0022608 | A | 3/2018 | |
| KR | 2018-0095919 | A | 8/2018 | |
| KR | 2019-0010498 | A | 1/2019 | |
| KR | 20180022608 | * | 1/2019 | ............. H01L 51/50 |
| WO | WO 2014/157599 | A1 | 10/2014 | |
| WO | WO 2015/182872 | A1 | 12/2015 | |
| WO | WO 2016/140497 | A2 | 9/2016 | |
| WO | WO 2017/109637 | A1 | 6/2017 | |
| WO | WO 2019/017741 | A1 | 1/2019 | |

OTHER PUBLICATIONS

International Search Report (Application No. PCT/IB2019/054167) Dated Jul. 16, 2019.
Written Opinion (Application No. PCT/IB2019/054167) Dated Jul. 16, 2019.

* cited by examiner

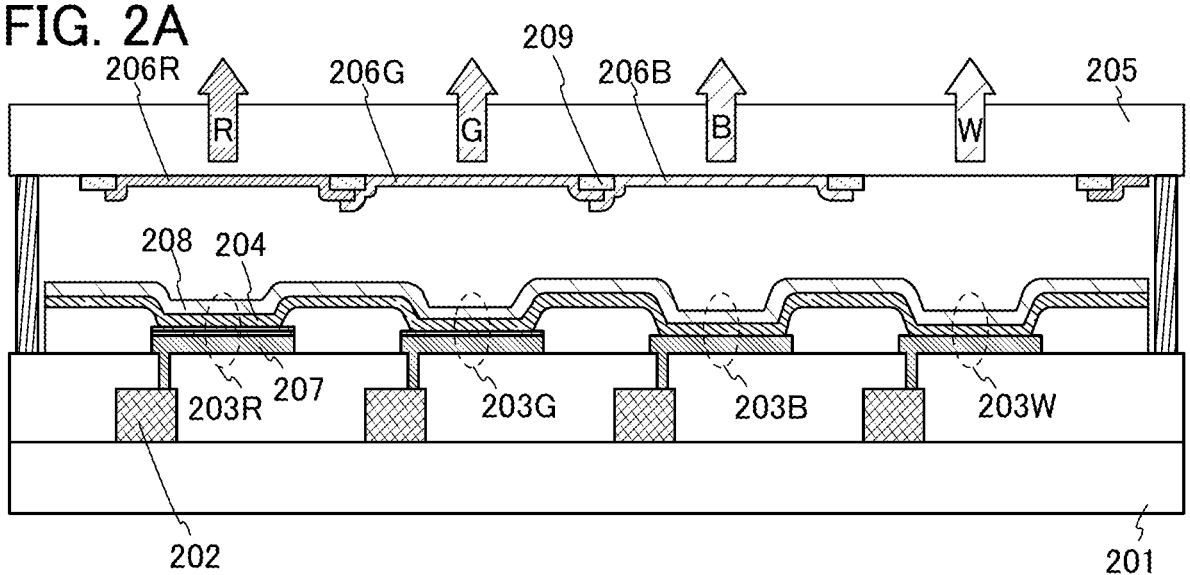
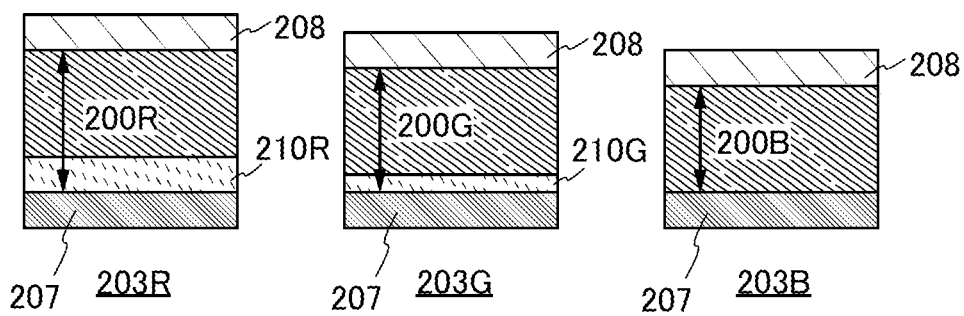
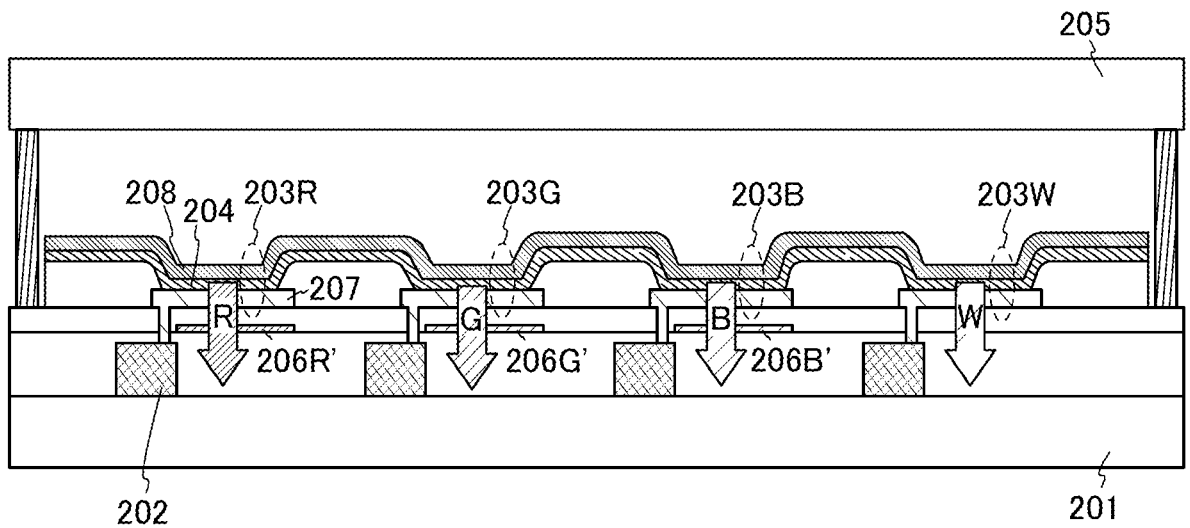

4000

4200

ORGANIC COMPOUND, LIGHT-EMITTING ELEMENT, LIGHT-EMITTING DEVICE, ELECTRONIC DEVICE, AND LIGHTING DEVICE

This application is a 371 of international application PCT/IB2019/054167 filed on May 21, 2019 which is incorporated herein by reference.

TECHNICAL FIELD

One embodiment of the present invention relates to an organic compound, a light-emitting element, a light-emitting device, an electronic device, and a lighting device. However, one embodiment of the present invention is not limited to the above technical field. That is, one embodiment of the present invention relates to an object, a method, a manufacturing method, or a driving method. Alternatively, one embodiment of the present invention relates to a process, a machine, manufacture, or a composition of matter. Specific examples include a semiconductor device, a display device, a liquid crystal display device, and the like.

BACKGROUND ART

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the emission spectrum obtained from a light-emitting substance depends on the light-emitting substance, the use of different types of organic compounds as light-emitting substances makes it possible to obtain light-emitting elements which exhibit various emission colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

SUMMARY OF THE INVENTION

Problems to be Solved by the Invention

Thus, in one embodiment of the present invention, a novel organic compound is provided. In another embodiment of the present invention, a benzofuropyrimidine derivative or a benzothienopyrimidine derivative that is a novel organic compound is provided. In one embodiment of the present invention, a novel organic compound that can be used in a light-emitting element is provided. In one embodiment of the present invention, a novel organic compound that can be used in an EL layer of a light-emitting element is provided. In addition, a highly reliable and novel light-emitting element using a novel organic compound of one embodiment of the present invention is provided. In addition, a novel light-emitting device, a novel electronic device, or a novel lighting device is provided. Note that the description of these objects does not preclude the existence of other objects. In one embodiment of the present invention, there is no need to achieve all of these objects. Objects other than these are apparent from the description of the specification, the drawings, the claims, and the like, and objects other than these can be derived from the description of the specification, the drawings, the claims, and the like.

Means for Solving the Problems

One embodiment of the present invention is a benzofuropyrimidine derivative or a benzothienopyrimidine derivative which is an organic compound represented by General Formula (G1) below. As shown in General Formula (G1) below, the organic compound has a structure which includes an unsubstituted phenyl group at the 8-position of a benzofuropyrimidine skeleton or a benzothienopyrimidine skeleton.

[Chemical Formula 1]

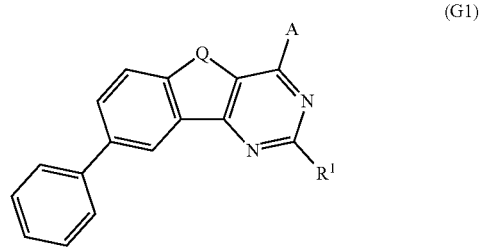

(G1)

In the above General Formula (G1), Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is a benzofuropyrimidine derivative or a benzothienopyrimidine derivative which is an organic compound represented by General Formula (G2) below. As shown in General Formula (G2) below, the organic compound has a structure which includes an unsubstituted phenyl group at the 8-position of a benzofuropyrimidine skeleton or a benzothienopyrimidine skeleton.

[Chemical Formula 2]

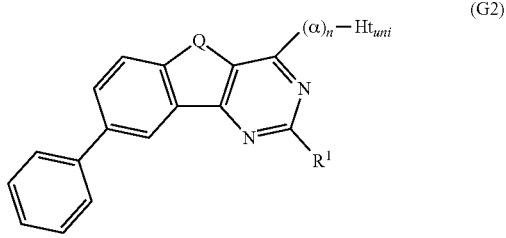
(G2)

In the above General Formula (G2), Q represents oxygen or sulfur. Furthermore, α represents a substituted or unsubstituted phenylene group, and n represents an integer of 0 to 4. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is a benzofuropyrimidine derivative or a benzothienopyrimidine derivative which is an organic compound represented by General Formula (G3) below. As shown in General Formula (G3) below, the organic compound has a structure which includes an unsubstituted phenyl group at the 8-position of a benzofuropyrimidine skeleton or a benzothienopyrimidine skeleton.

[Chemical Formula 3]

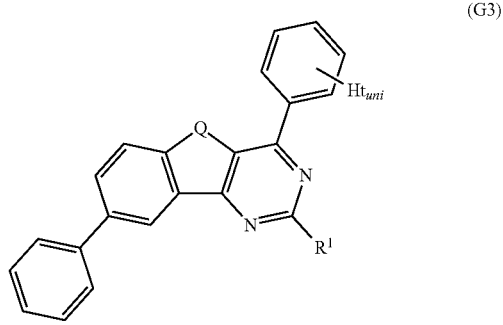
(G3)

In the above General Formula (G3), Q represents oxygen or sulfur. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is a benzofuropyrimidine derivative or a benzothienopyrimidine derivative which is an organic compound represented by General Formula (G4) below. As shown in General Formula (G4) below, the organic compound has a structure which includes an unsubstituted phenyl group at the 8-position of a benzofuropyrimidine skeleton or a benzothienopyrimidine skeleton.

[Chemical Formula 4]

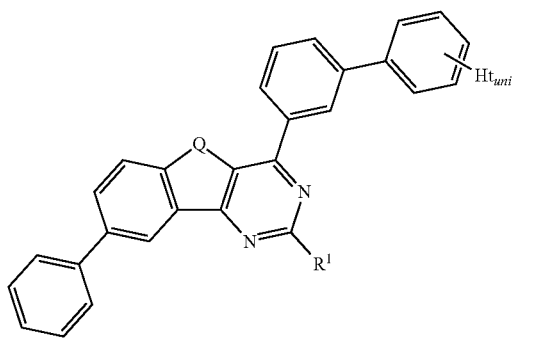
(G4)

In the above General Formula (G4), Q represents oxygen or sulfur. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Note that in each of the above-described structures, the $Ht_{uni}$ in the above General Formulae (G2), (G3), and (G4) each independently have any one of a pyrrole ring structure, a furan ring structure, or a thiophene ring structure.

Furthermore, in each of the above-described structures, the $Ht_{uni}$ in the above General Formulae (G2), (G3), and (G4) are each independently represented by any one of General Formulae (Ht-1) to (Ht-26) below.

[Chemical Formulae 5]

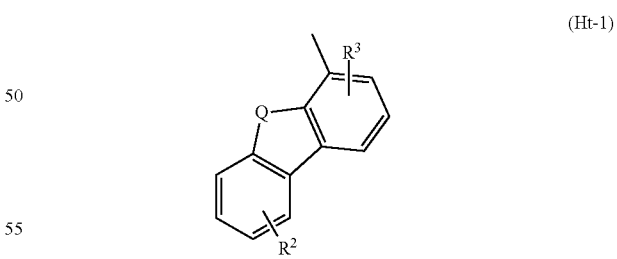
(Ht-1)

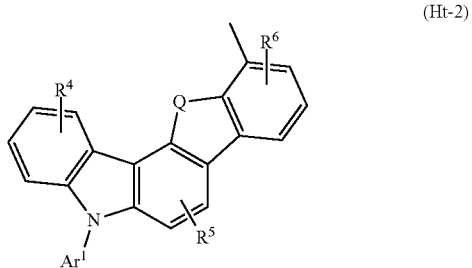
(Ht-2)

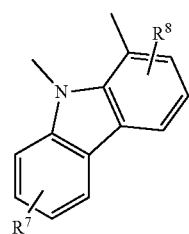 (Ht-3)
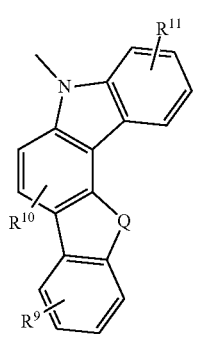 (Ht-4)
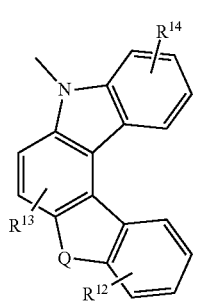 (Ht-5)
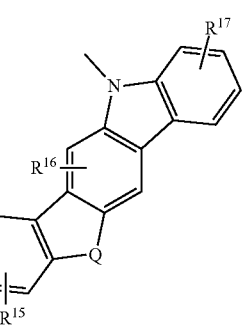 (Ht-6)
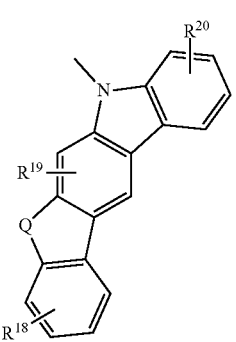 (Ht-7)
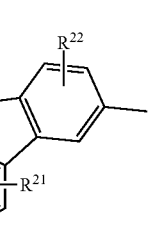 (Ht-8)
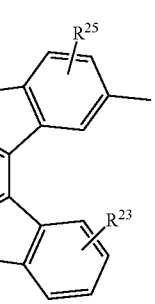 (Ht-9)
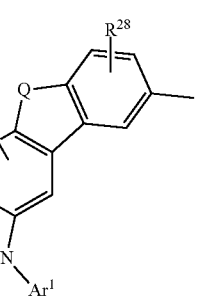 (Ht-10)
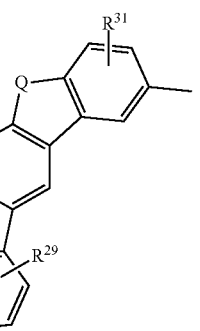 (Ht-11)
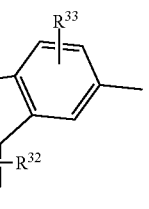 (Ht-12)

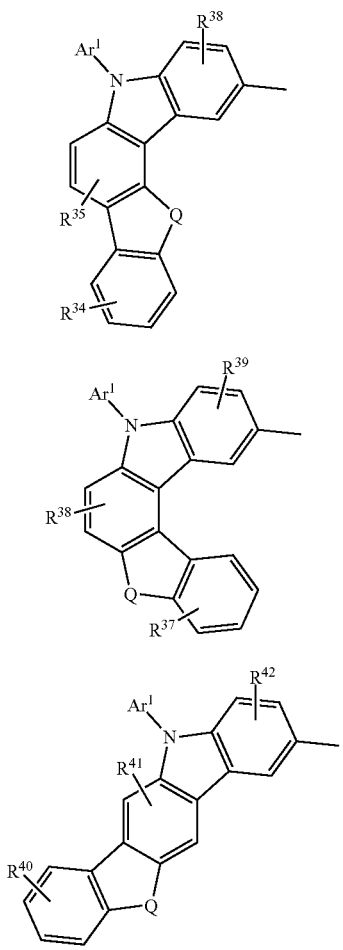
(Ht-13)
(Ht-14)
(Ht-15)
(Ht-16)
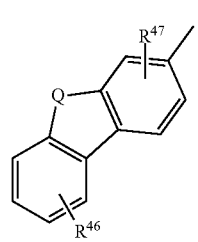
(Ht-17)
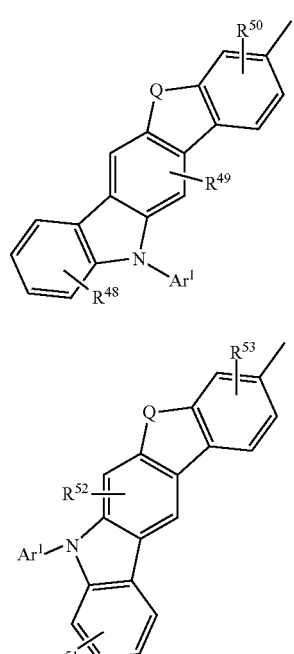
(Ht-18)
(Ht-19)
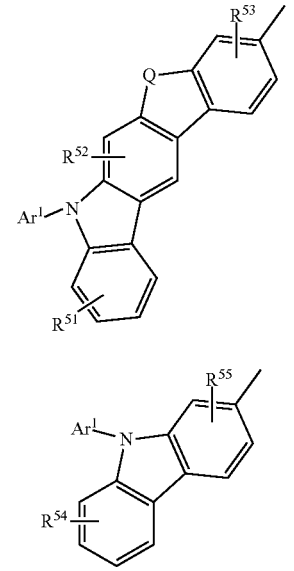
(Ht-20)
(Ht-21)
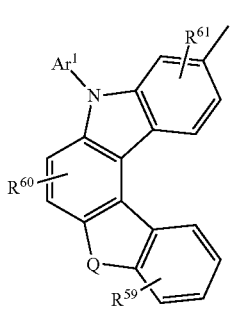
(Ht-22)

-continued (Ht-23)
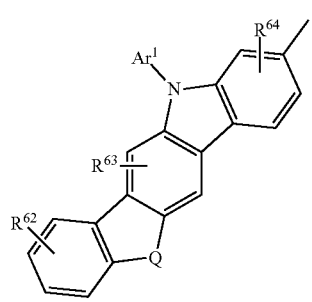

(Ht-24)
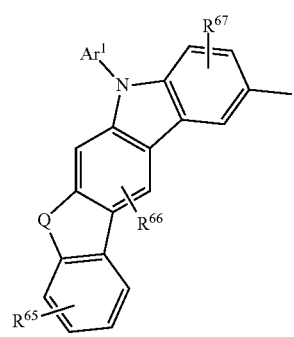

(Ht-25)

(Ht-26)
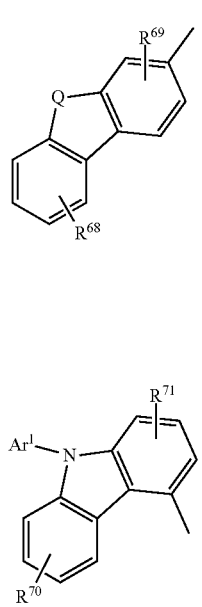

[Chemical Formulae 6]

(100)
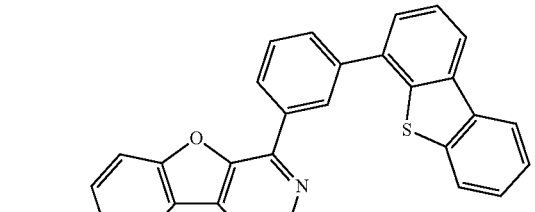

(101)
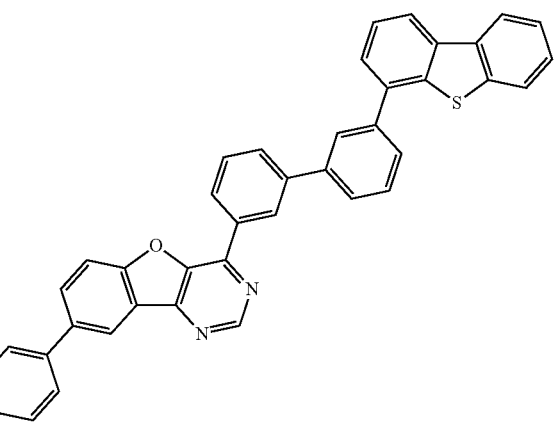

(102)
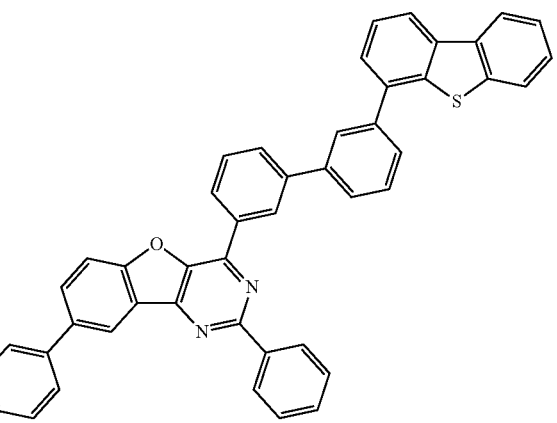

(117)
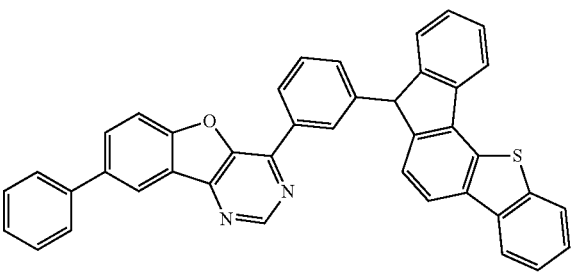

In the above General Formulae (Ht-1) to (Ht-26) above, Q represents oxygen or sulfur. Furthermore, $R^2$ to $R^{71}$ each represent 1 to 4 substituents and each independently represent any one of hydrogen, an alkyl group having 1 to 6 carbon atoms, and a substituted or unsubstituted phenyl group. Furthermore, $Ar^1$ represents a substituted or unsubstituted aryl group having 6 to 13 carbon atoms.

Furthermore, another embodiment of the present invention is an organic compound represented by any one of Structural Formulae (100), (101), (102), (117), and (200).

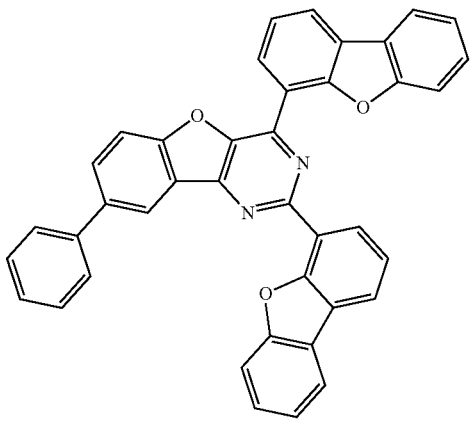

(200)

Another embodiment of the present invention is a light-emitting element in which the above-described organic compound of one embodiment of the present invention is used. The present invention also includes a light-emitting element including a guest material in addition to the above-described organic compound.

Another embodiment of the present invention is a light-emitting element in which the above-described organic compound of one embodiment of the present invention is used. Note that the present invention also includes a light-emitting element that is formed using the organic compound of one embodiment of the present invention for an EL layer between a pair of electrodes or a light-emitting layer included in the EL layer. In addition to the aforementioned light-emitting elements, the present invention includes a light-emitting element including a layer (e.g., a cap layer) that is in contact with an electrode and contains an organic compound. In addition to the light-emitting elements, a light-emitting device including a transistor, a substrate, and the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

In addition, the scope of one embodiment of the present invention includes a light-emitting device including a light-emitting element, and a lighting device including the light-emitting device. Accordingly, the light-emitting device in this specification refers to an image display device or a light source (including a lighting device). In addition, a light-emitting device includes a module in which a light-emitting device is connected to a connector such as an FPC (Flexible printed circuit) or a TCP (Tape Carrier Package), a module in which a printed wiring board is provided on the tip of a TCP, or a module in which an IC (integrated circuit) is directly mounted on a light-emitting element by a COG (Chip On Glass) method.

Effect of the Invention

In one embodiment of the present invention, a novel organic compound can be provided. In another embodiment of the present invention, a benzofuropyrimidine derivative or a benzothienopyrimidine derivative that is a novel organic compound can be provided. In one embodiment of the present invention, a novel organic compound that can be used in a light-emitting element can be provided. In one embodiment of the present invention, a novel organic compound that can be used in an EL layer of a light-emitting element can be provided. In addition, a highly reliable and novel light-emitting element can be provided by using a novel organic compound of one embodiment of the present invention. In addition, a novel light-emitting device, a novel electronic device, or a novel lighting device can be provided.

BRIEF DESCRIPTION OF THE DRAWINGS

FIGS. 2A-2C are drawings illustrating light-emitting devices.

MODE FOR CARRYING OUT THE INVENTION

Figure 1A:
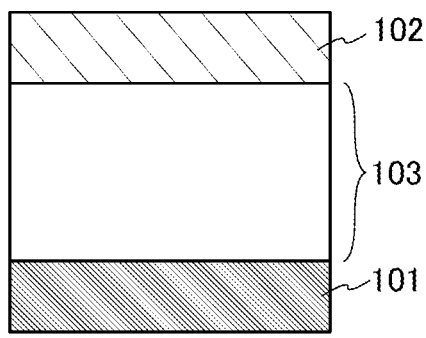
FIGS. 1A-1E are drawings illustrating structures of light-emitting elements.

Embodiments of the present invention are described in detail below with reference to drawings. Note that the present invention is not limited to the following description, and the modes and details of the present invention can be modified in various ways without departing from the spirit and scope of the present invention. Thus, the present invention should not be construed as being limited to the descriptions in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in drawings and the like.

Furthermore, when describing the structures of the invention with reference to the drawings in this specification and the like, the reference numerals denoting the same components are commonly used in different drawings.

Embodiment 1

In this embodiment, organic compounds of embodiments of the present invention will be described. An organic compound of one embodiment of the present invention is a benzofuropyrimidine derivative or a benzothienopyrimidine derivative represented by General Formula (G1) below. The organic compound which is one embodiment of the present invention has a structure which includes an unsubstituted phenyl group at the 8-position of a benzofuropyrimidine skeleton or a benzothienopyrimidine skeleton as shown in General Formula (G1) below.

[Chemical Formula 7]

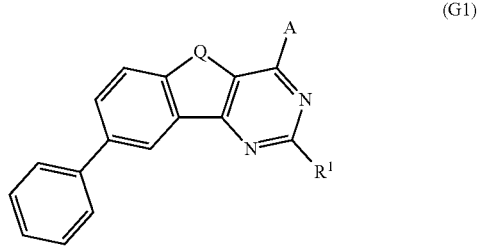

(G1)

In General Formula (G1), Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G2) below.

[Chemical Formula 8]

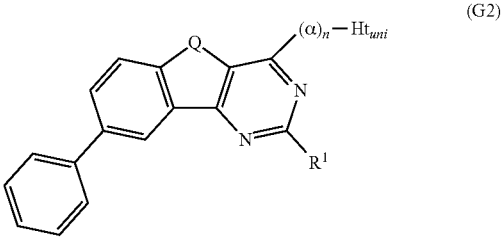

(G2)

In the above General Formula (G2), Q represents oxygen or sulfur. Furthermore, α represents a substituted or unsubstituted phenylene group, and n represents an integer of 0 to 4. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G3) below.

[Chemical Formula 9]

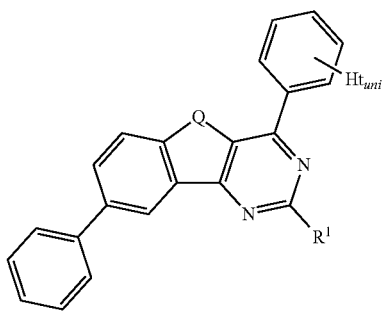

(G3)

In the above General Formula (G3), Q represents oxygen or sulfur. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G4) below.

[Chemical Formula 10]

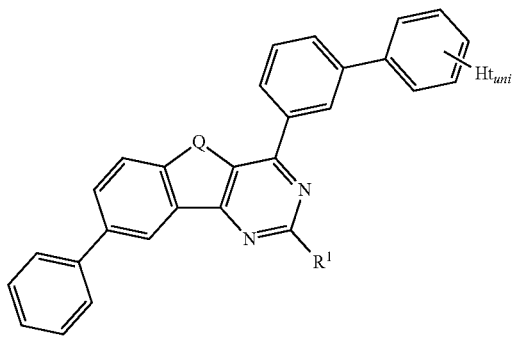

(G4)

In the above General Formula (G4), Q represents oxygen or sulfur. In addition, $Ht_{uni}$ represents a skeleton having a hole-transport property. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Note that $Ht_{uni}$ in the above General Formulae (G2), (G3), and (G4) each independently have any one of a pyrrole ring structure, a furan ring structure, or a thiophene ring structure.

In addition, $Ht_{uni}$ in General Formulae (G2), (G3), and (G4) above are each independently represented by any one of General Formulae (Ht-1) to (Ht-26) below.

[Chemical Formulae 11]

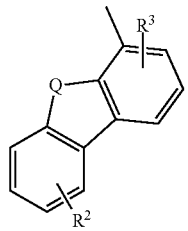

(Ht-1)

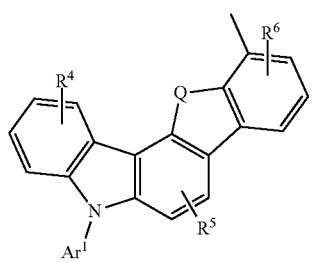

(Ht-2)

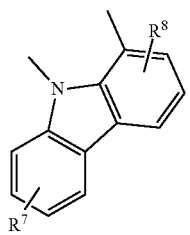

(Ht-3)

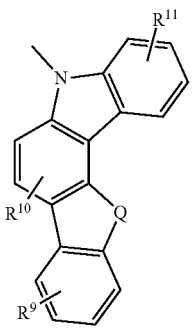

(Ht-4)

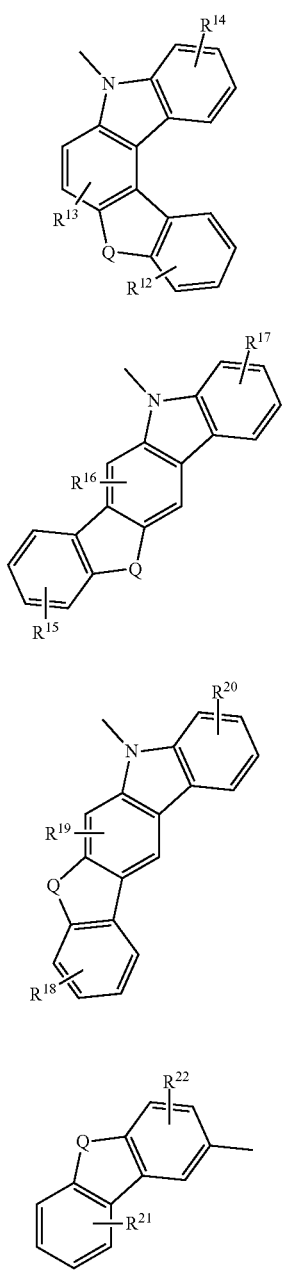
(Ht-5)
(Ht-6)
(Ht-7)
(Ht-8)
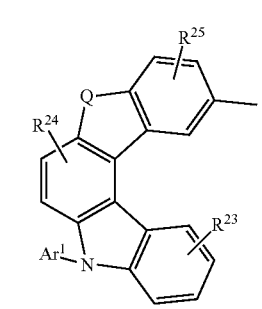
(Ht-9)
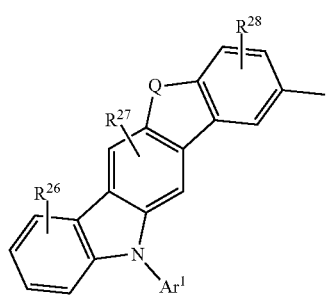
(Ht-10)
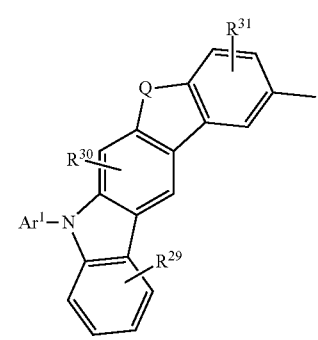
(Ht-11)
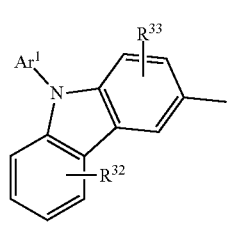
(Ht-12)
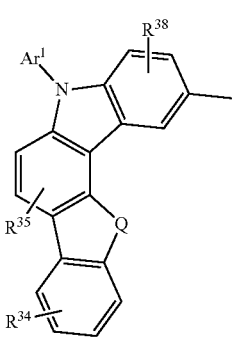
(Ht-13)
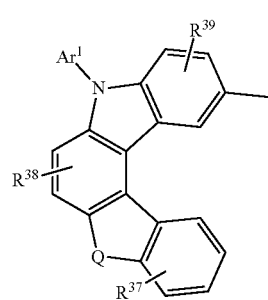
(Ht-14)

(Ht-15)
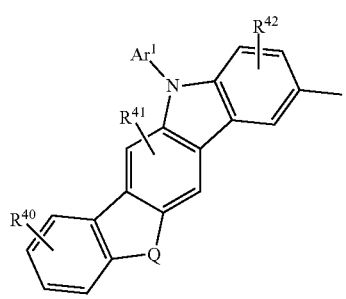
(Ht-16)
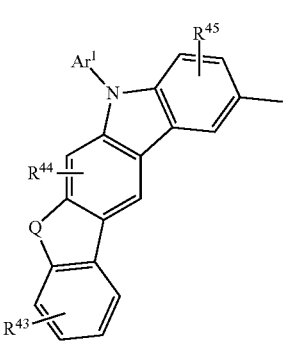
(Ht-17)
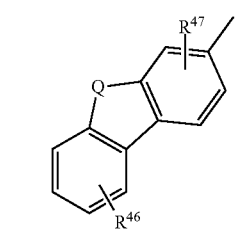
(Ht-18)
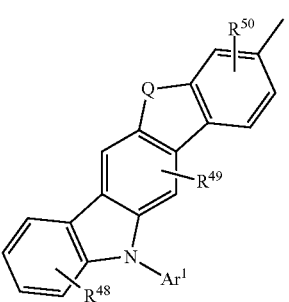
(Ht-19)
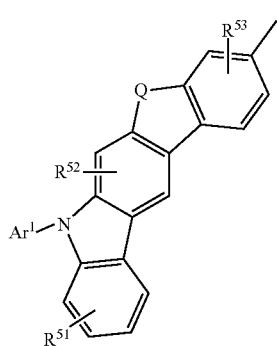
(Ht-20)
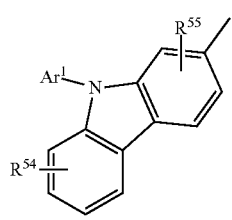
(Ht-21)
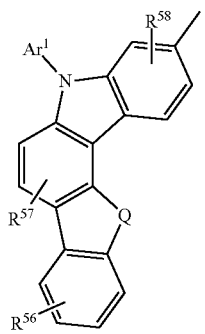
(Ht-22)
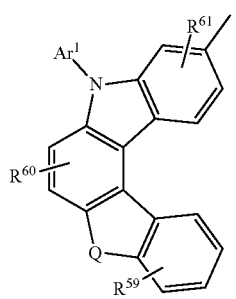
(Ht-23)
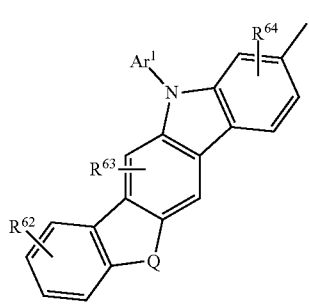
(Ht-24)
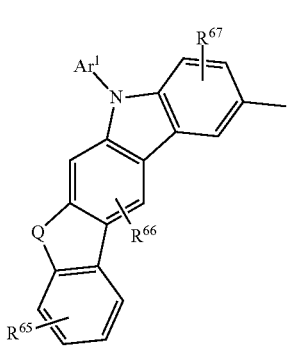

(Ht-25)

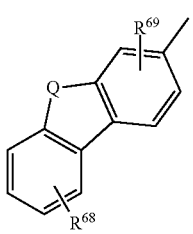

(Ht-26)

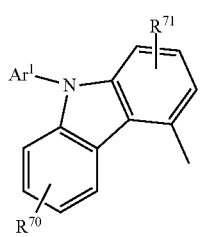

In General Formulae (Ht-1) to (Ht-26) above, Q represents oxygen or sulfur. Furthermore, $R^2$ to $R^{71}$ each represent 1 to 4 substituents and each independently represent any one of hydrogen, an alkyl group having 1 to 6 carbon atoms, and a substituted or unsubstituted phenyl group. Furthermore, Ar' represents a substituted or unsubstituted aryl group having 6 to 13 carbon atoms.

Note that in the case where the substituted or unsubstituted monocyclic saturated hydrocarbon having 5 to 7 carbon atoms, the substituted or unsubstituted polycyclic saturated hydrocarbon having 7 to 10 carbon atoms, the substituted or unsubstituted aryl group having 6 to 13 carbon atoms, the substituted or unsubstituted heteroaryl group having 3 to 12 carbon atoms, or the substituted or unsubstituted phenylene group in the above General Formulae (G1), (G2), (G3), and (G4) has a substituent, examples of the substituent include an alkyl group having 1 to 7 carbon atoms such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms such as a cyclopentyl group, a cyclohexyl group, a cycloheptyl group, or a 8,9,10-trinorbornanyl group, and an aryl group having 6 to 12 carbon atoms such as a phenyl group, a naphthyl group, or a biphenyl group.

In the case where $R^1$ in the above General Formulae (G1), (G2), (G3), and (G4) represents a monocyclic saturated hydrocarbon having 5 to 7 carbon atoms, specific examples thereof include a cyclopentyl group, a cyclohexyl group, a 1-methylcyclohexyl group, and a cycloheptyl group.

In the case where $R^1$ in General Formulae (G1), (G2), (G3), and (G4) above represents a polycyclic saturated hydrocarbon having 7 to 10 carbon atoms, specific examples thereof include a norbornyl group, an adamantyl group, a decalin group, and a tricyclodecyl group.

In the case where $R^1$ in the above General Formulae (G1), (G2), (G3), and (G4) represents an aryl group having 6 to 13 carbon atoms, specific examples thereof include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, and a fluorenyl group.

In the case where $R^1$ in General Formulae (G1), (G2), (G3), and (G4) above represents an alkyl group having 1 to 6 carbon atoms, specific examples thereof include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

In the case where $R^1$ in the above General Formulae (G1), (G2), (G3), and (G4) represents a heteroaryl group having 3 to 12 carbon atoms, specific examples thereof include a triadinyl group, a pyrazinyl group, a pyrimidinyl group, a pyridinyl group, a quinolinyl group, an isoquinolinyl group, a benzothienyl group, a benzofuranyl group, an indolyl group, a dibenzothienyl group, a dibenzofuranyl group, and a carbazolyl group.

Note that when $R^1$ in the above General Formulae (G1), (G2), (G3), and (G4) has the group represented by the above-described specific examples, the organic compound of one embodiment of the present invention has a high T1 level.

Next, specific structural formulae of the above-described organic compound of one embodiment of the present invention are shown below. Note that the present invention is not limited to these formulae.

[Chemical Formulae 12]

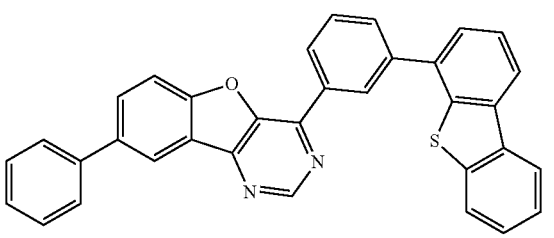

(100)

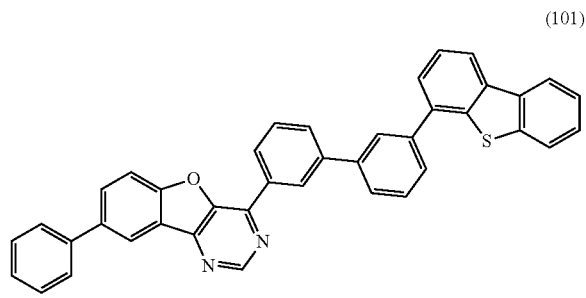

(101)

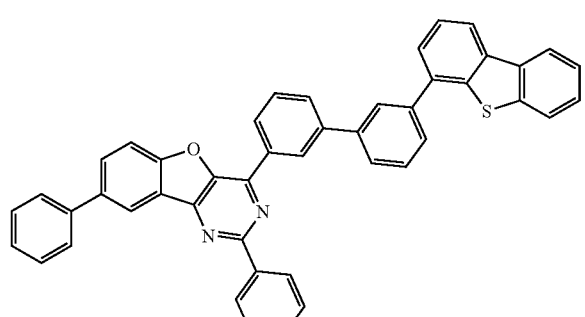

(102)

(103)
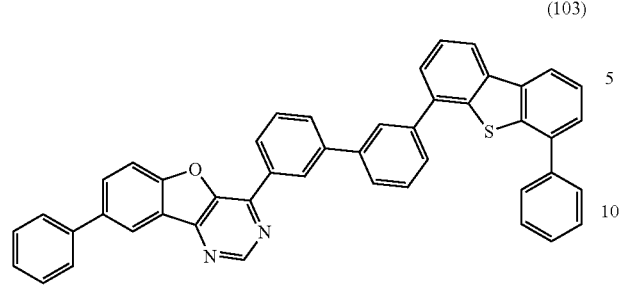
(104)
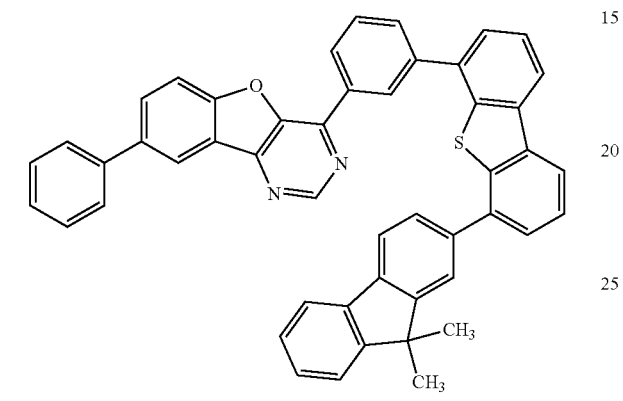
(105)
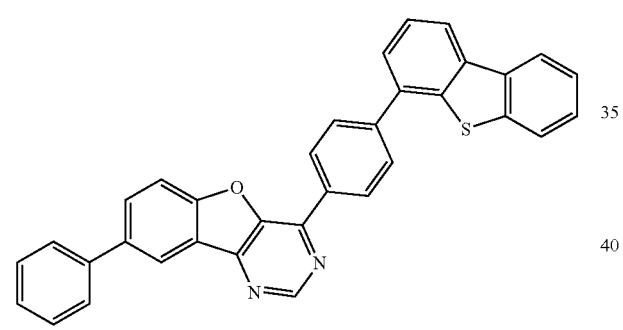
(106)
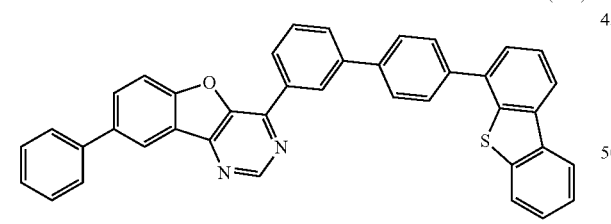
(107)
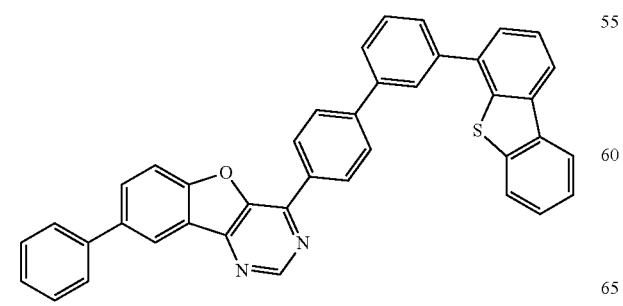
(108)
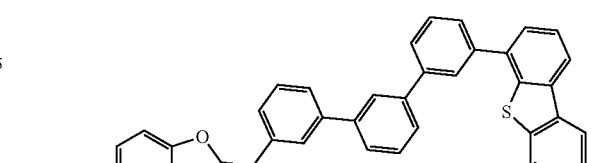
(109)
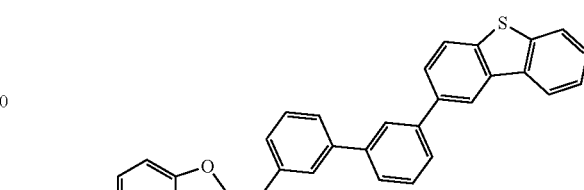
(110)
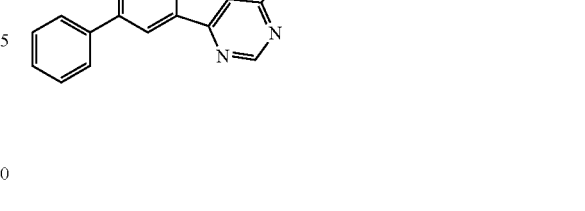
(111)

[Chemical Formulae 13]
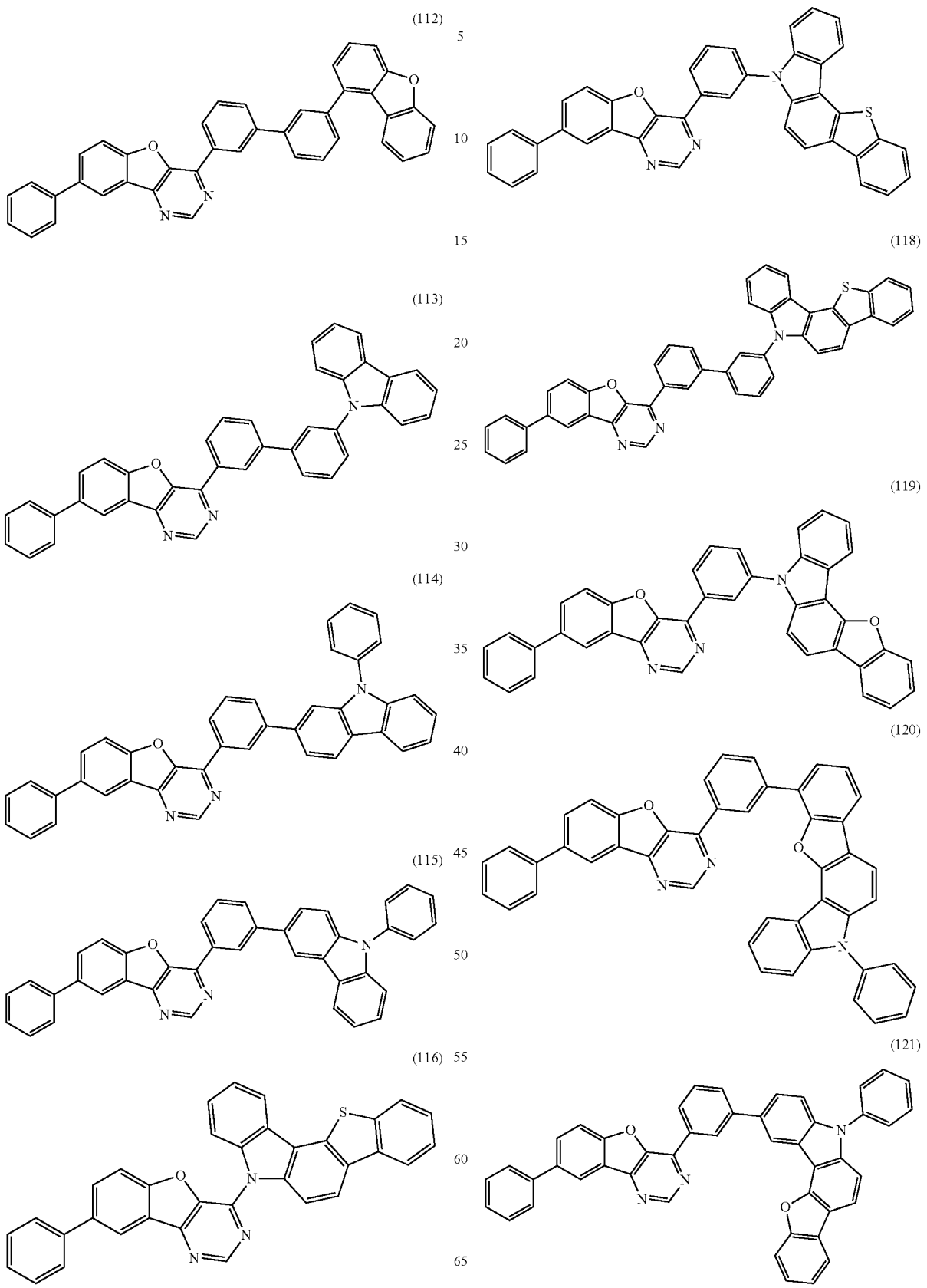

(122)
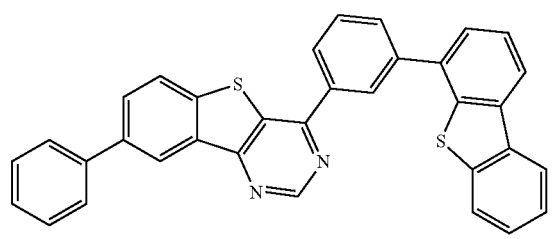
(123)
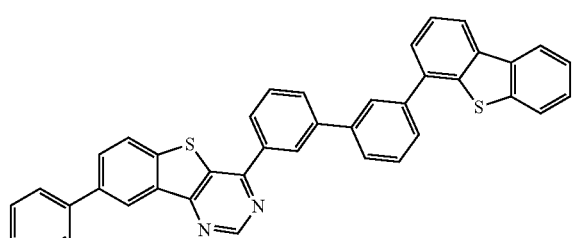
[Chemical Formula 14]
(200)
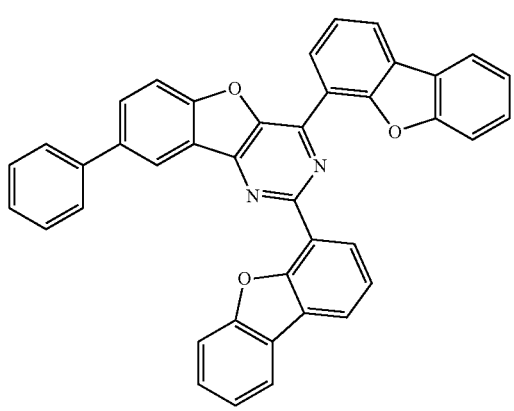
(201)
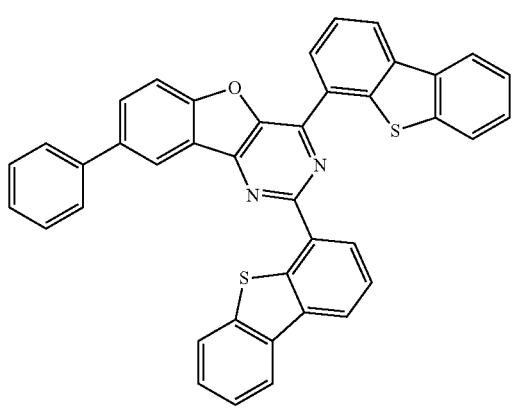
(202)
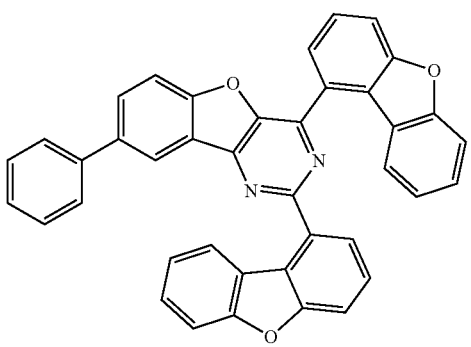
(203)
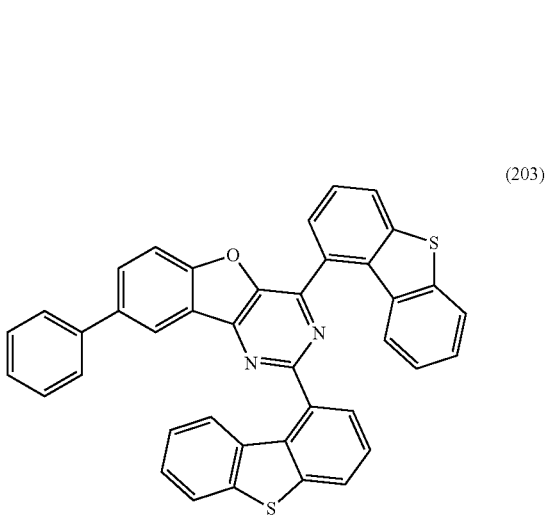
(204)
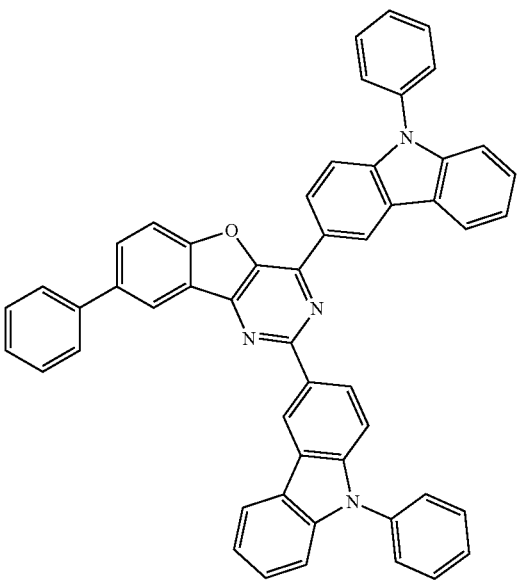

-continued

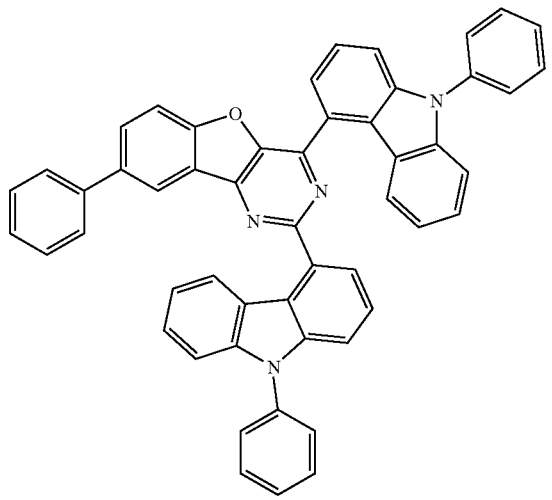

(205)

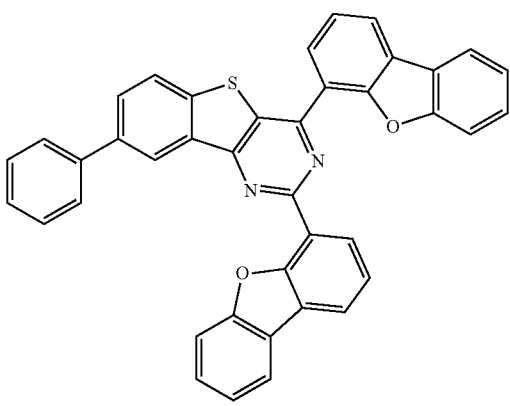

(206)

Note that the organic compounds represented by the above Structural Formulae (100) to (123) and (200) to (206) are examples of the organic compound represented by the above General Formula (G1), and the organic compound of one embodiment of the present invention is not limited thereto.

Next, a synthesis method of a benzofuropyrimidine derivative or a benzothienopyrimidine derivative, which is one embodiment of the present invention and represented by General Formula (G1) below, will be described.

[Chemical Formula 15]

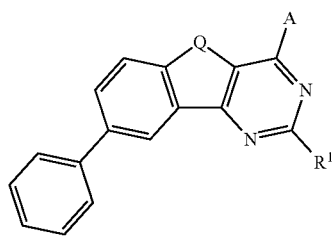

(G1)

In General Formula (G1), Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

<<Method for Synthesizing Organic Compound Represented by General Formula (G1)>>

A variety of reactions can be used for the synthesis of the organic compound represented by the above General Formula (G1); for example, the organic compound represented by General Formula (G1) can be synthesized by a simple method shown by synthesis schemes below.

The organic compound represented by General Formula (G1) can be obtained by the reaction of a halogen compound (A1) having a benzofuropyrimidine skeleton or a benzothienopyrimidine skeleton whose 8-position is substituted by a phenyl group and a boronic acid compound of A (A2), as shown in a synthesis scheme (P1) below.

[Chemical Formulae 16]

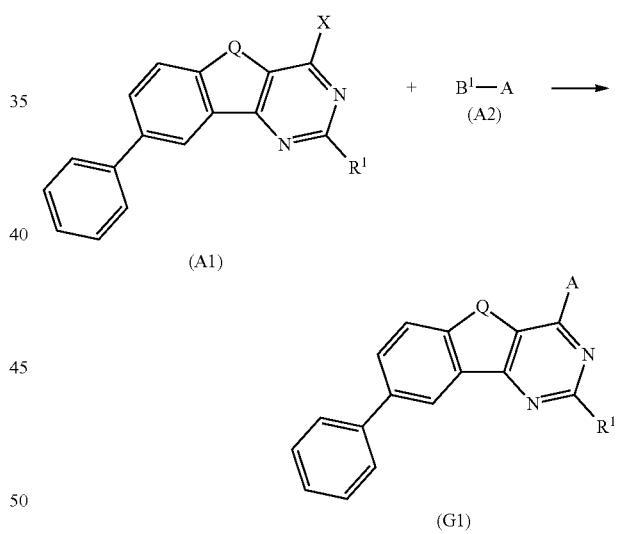

In the above synthesis scheme (P1), X represents a halogen and Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

The organic compound represented by General Formula (G1) can also be obtained by the reaction of a dihalogen compound (B1) having a benzofuropyrimidine skeleton or a benzothienopyrimidine skeleton and a boronic acid compound of A (A2) and the reaction of an intermediate (B2) and a phenylboronic acid compound (B3), as shown in a synthesis scheme (P2) below.

[Chemical Formulae 17]

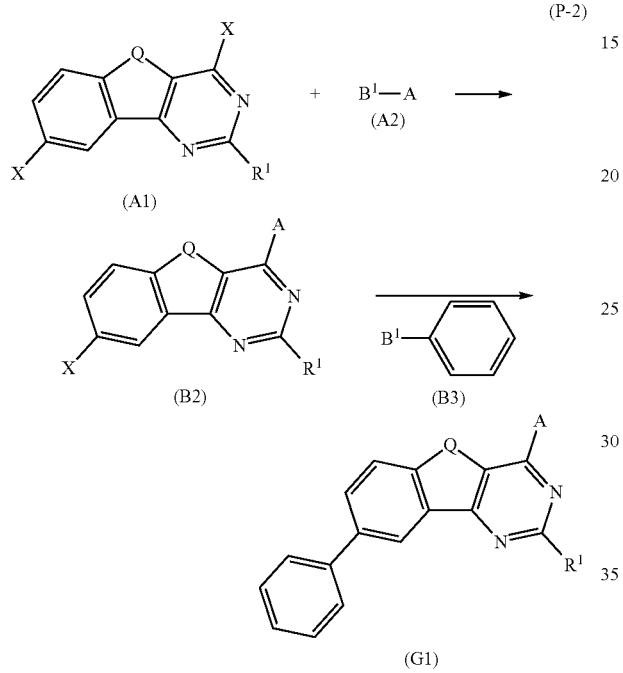

[Chemical Formula 18]

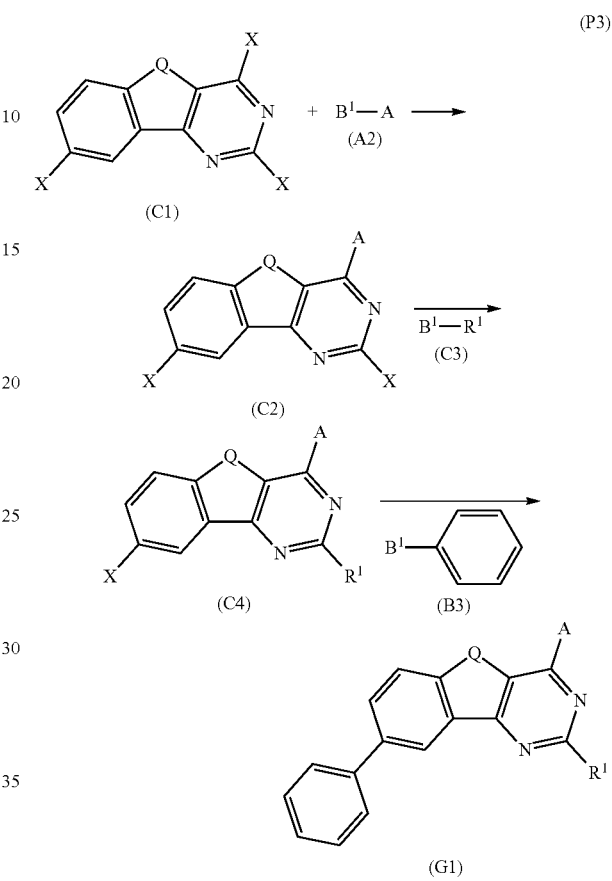

intermediate (C4) and a phenylboronic acid compound (B3), as shown in a synthesis scheme (P3) below.

In the above synthesis scheme (P2), X represents a halogen and Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms. In addition, $B^1$ represents a boronic acid, a boronic ester, a cyclic-triolborate salt, or the like. As the cyclic-triolborate salt, a lithium salt, a potassium salt, or a sodium salt may be used.

The organic compound represented by General Formula (G1) can also be obtained by the reaction of a trihalogen compound (C1) having a benzofuropyrimidine skeleton or a benzothienopyrimidine skeleton and a boronic acid compound of A (A2), the reaction of an intermediate (C2) and a boronic acid compound of $R^1$ (C3), and the reaction of an In the above synthesis scheme (P3), X represents a halogen and Q represents oxygen or sulfur. Furthermore, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms. In addition, $B^1$ represents a boronic acid, a boronic ester, a cyclic-triolborate salt, or the like. As the cyclic-triolborate salt, a lithium salt, a potassium salt, or a sodium salt may be used.

Note that various kinds of the halogen compound (A1) including a benzofuropyrimidine skeleton or a benzothienopyrimidine skeleton whose 8-position is substituted by a phenyl group, the boronic acid compound of A (A2), the dihalogen compound (B1) including a benzofuropyrimidine skeleton or a benzothienopyrimidine skeleton, the intermediate (B2), the phenylboronic acid compound (B3), the trihalogen compound (C1) including a benzofuropyrimidine skeleton or a benzothienopyrimidine skeleton, the intermediate (C2), the boronic acid compound of $R^1$ (C3), and the intermediate (C4) used in the above synthesis schemes (P1), (P2), and (P3) are commercially available or can be synthesized; accordingly, many kinds of the benzofuropyrimidine derivatives or benzothienopyrimidine derivatives represented by General Formula (G1) can be synthesized. Thus, the organic compound of one embodiment of the present invention is characterized by having numerous variations.

Described above are the organic compounds of embodiments of the present invention and examples of the synthesis method; however, the present invention is not limited thereto and the organic compound may be synthesized by another synthesis method.

The structures described in this embodiment can be used in an appropriate combination with the structures described in the other embodiments.

Embodiment 2

In this embodiment, a light-emitting element in which the organic compound described in Embodiment 1 is used will be described with reference to FIG. 1.

<<Basic Structure of Light-Emitting Element>>

First, a basic structure of a light-emitting element will be described. FIG. 1(A) illustrates an example of a light-emitting element including, between a pair of electrodes, an EL layer having a light-emitting layer. Specifically, the light-emitting element has a structure in which an EL layer 103 is sandwiched between a first electrode 101 and a second electrode 102.

Figure 1B:
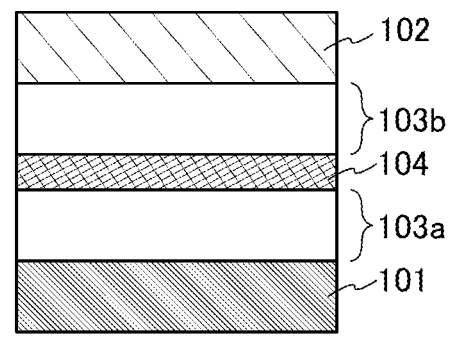

FIG. 1(B) illustrates an example of a light-emitting element with a stacked-layer structure (tandem structure) in which a plurality of (two layers, in FIG. 1(B)) EL layers (103a and 103b) are provided between a pair of electrodes and a charge-generation layer 104 is provided between the EL layers. With a tandem light-emitting element, a light-emitting device that can be driven at low voltage with low power consumption can be obtained.

The charge-generation layer 104 has a function of injecting electrons into one of the EL layers (103a or 103b) and injecting holes into the other of the EL layers (103b or 103a) when voltage is applied to the first electrode 101 and the second electrode 102. Thus, when voltage is applied in FIG. 1(B) such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a light-transmitting property with respect to visible light (specifically, the visible light transmittance with respect to the charge-generation layer 104 is 40% or higher). Furthermore, the charge-generation layer 104 functions even when having lower conductivity than the first electrode 101 or the second electrode 102.

Figure 1C:
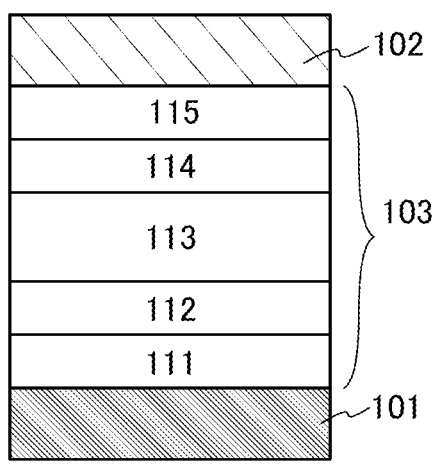

FIG. 1(C) illustrates an example of the case where the EL layer 103 illustrated in FIG. 1(A) has a stacked-layer structure (which also applies to the case where the EL layers (103a and 103b) in FIG. 1(B) have stacked-layer structures). Note that in this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked sequentially over the first electrode 101. Even in the case where a plurality of EL layers are provided as in the tandem structure illustrated in FIG. 1(B), each EL layer has a stacked-layer structure, sequentially stacked from the anode side as described above. When the first electrode 101 is a cathode and the second electrode 102 is an anode, the stacking order in the EL layer is reversed.

The light-emitting layers 113 included in the EL layers (103, 103a, and 103b) each contain an appropriate combination of a light-emitting substance and a plurality of substances, so that fluorescence or phosphorescence with a desired emission color can be obtained. Furthermore, the light-emitting layer 113 may have a stacked-layer structure having different emission colors. In that case, different materials may be used for the light-emitting substance and other substances used in each of the light-emitting layers that are stacked. Furthermore, a structure in which different emission colors can be obtained from the plurality of EL layers (103a and 103b) illustrated in FIG. 1(B) may be employed. Also in that case, different materials may be used for the light-emitting substance and other substances used in each of the light-emitting layers.

In addition, in the light-emitting element of one embodiment of the present invention, a structure may be employed in which light emission obtained from the EL layers (103, 103a, and 103b) is resonated between both of the electrodes so that the obtained light emission is intensified. For example, in FIG. 1(C), the light-emitting element can have a micro optical resonator (microcavity) structure when the first electrode 101 is a reflective electrode and the second electrode 102 is a semi-transmissive and semi-reflective electrode, and light emission obtained from the EL layer 103 can be intensified.

Note that when the first electrode 101 of the light-emitting element is a reflective electrode having a stacked-layer structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region refers to a region where holes and electrons are recombined in the light-emitting layer 113.

By performing such optical adjustment, the spectrum of specific monochromatic light obtained from the light-emitting layer 113 can be narrowed and light emission with high color purity can be obtained.

However, in the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained with given positions in the first electrode 101 and the second electrode 102 being supposed to be reflective regions. Furthermore, the optical path length between the first electrode 101 and the light-emitting layer from which the desired light is obtained is, to be exact, the optical path length between the reflective region in the first electrode 101 and the light-emitting region in the light-emitting layer from which the desired light is obtained. However, it is difficult to precisely determine the reflective region in the first electrode 101 and the light-emitting region in the light-emitting layer from which the desired light is obtained; thus, it is assumed that the above effect can be sufficiently obtained with a given position in the first electrode 101 being supposed to be the reflective region and a given position in the light-emitting layer from which the desired light is obtained being supposed to be the light-emitting region.

In the case where the light-emitting element illustrated in FIG. 1(C) has a microcavity structure, light (monochromatic light) with different wavelengths can be extracted even when the same EL layer is used. Thus, separate coloring for obtaining different emission colors (e.g., R, G, and B) is not necessary, and high definition can be achieved. In addition, a combination with coloring layers (color filters) is also possible. Furthermore, emission intensity of light with a specific wavelength in the front direction can be increased, so that power consumption can be reduced.

Figure 1D:
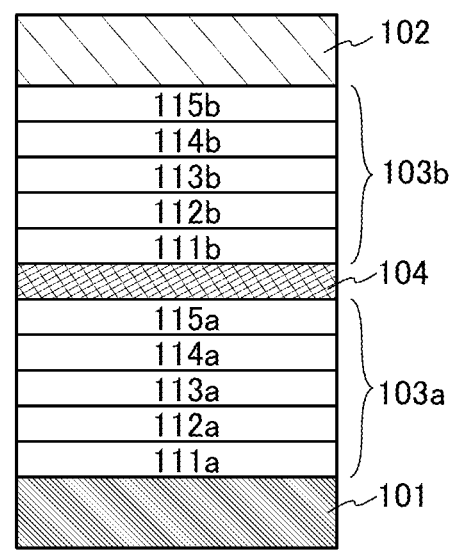
Figure 1E:
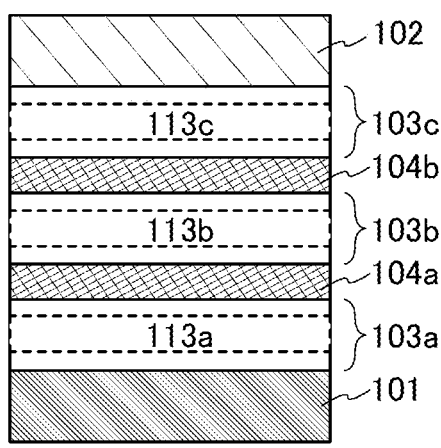

A light-emitting element illustrated in FIG. 1(E) is an example of the light-emitting element with the tandem structure illustrated in FIG. 1(B), and includes three EL layers (103a, 103b, and 103c) stacked with charge-generation layers (104a and 104b) sandwiched therebetween, as illustrated in the drawing. Note that the three EL layers (103a, 103b, and 103c) include respective light-emitting layers (113a, 113b, and 113c) and the emission colors of the respective light-emitting layers can be combined freely. For example, the light-emitting layer 113a can be blue, the light-emitting layer 113b can be red, green, or yellow, and the light-emitting layer 113c can be blue; for another example, the light-emitting layer 113a can be red, the light-emitting layer 113b can be blue, green, or yellow, and the light-emitting layer 113c can be red.

In the above light-emitting element of one embodiment of the present invention, at least one of the first electrode 101 and the second electrode 102 is a light-transmitting electrode (transparent electrode, semi-transmissive and semi-reflective electrode, or the like). In the case where the light-transmitting electrode is a transparent electrode, the visible light transmittance of the transparent electrode is 40% or higher. In the case where the light-transmitting electrode is a semi-transmissive and semi-reflective electrode, the visible light reflectance of the semi-transmissive and semi-reflective electrode is higher than or equal to 20% and lower than or equal to 80%, preferably higher than or equal to 40% and lower than or equal to 70%. The resistivity of these electrodes is preferably $1 \times 10^{-2}$ Ωcm or lower.

Furthermore, when one of the first electrode 101 and the second electrode 102 is a reflective electrode in the above light-emitting element of one embodiment of the present invention, the visible light reflectance of the reflective electrode is higher than or equal to 40% and lower than or equal to 100%, preferably higher than or equal to 70% and lower than or equal to 100%. The resistivity of this electrode is preferably $1 \times 10^{-2}$ Ωcm or lower.

<<Specific Structure and Fabrication Method of Light-Emitting Element>>

Next, specific structures and fabrication methods of the light-emitting elements of embodiments of the present invention illustrated in FIG. 1 will be described. Note that here, collective description is made on a light-emitting element with a tandem structure illustrated in FIG. 1(B), FIG. 1(D), and FIG. 1(E) in addition to the light-emitting element whose EL layer 103 has a single-layer structure as illustrated in FIG. 1(A) and FIG. 1(C). In the case where the light-emitting element illustrated in FIG. 1 has a microcavity structure, the first electrode 101 is formed as a reflective electrode and the second electrode 102 is formed as a semi-transmissive and semi-reflective electrode, for example. The electrode can be formed, using one or more kinds of desired electrode materials, as a single layer or a stacked layer. The second electrode 102 is formed after formation of the EL layer (103 or 103b), with the use of a material selected as described above. For fabrication of these electrodes, a sputtering method or a vacuum evaporation method can be used.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, and an In—W—Zn oxide can be given. In addition, it is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above as an example (for example, lithium (Li), cesium (Cs), calcium (Ca), or strontium (Sr)), a rare earth metal such as europium (Eu) or ytterbium (Yb), an alloy containing an appropriate combination of any of these elements, graphene, or the like.

When the light-emitting element illustrated in FIG. 1 includes the EL layer 103 having a stacked-layer structure as in FIG. 1(C) and the first electrode 101 is an anode, the hole-injection layer 111 and the hole-transport layer 112 of the EL layer 103 are sequentially stacked over the first electrode 101 by a vacuum evaporation method. Alternatively, when the plurality of EL layers (103a and 103b) each having a stacked-layer structure are stacked with the charge-generation layer 104 therebetween as in FIG. 1(D) and the first electrode 101 is an anode, a hole-injection layer 111a and a hole-transport layer 112a of the EL layer 103a are sequentially stacked over the first electrode 101 by a vacuum evaporation method. Furthermore, after the EL layer 103a and the charge-generation layer 104 are sequentially stacked, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) are each a layer that injects holes from the first electrode 101 which is an anode and the charge-generation layer (104) to the EL layers (103, 103a, and 103b) and contains a material with a high hole-injection property.

As examples of the material with a high hole-injection property, transition metal oxides such as a molybdenum oxide, a vanadium oxide, a ruthenium oxide, a tungsten oxide, and a manganese oxide can be given. Alternatively, it is possible to use a phthalocyanine-based compound such as phthalocyanine (abbreviation: H$_2$Pc) or copper phthalocyanine (abbreviation: CuPc), or the like.

It is also possible to use an aromatic amine compound, which is a low molecular compound, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

It is also possible to use a high molecular compound (an oligomer, a dendrimer, a polymer, or the like) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl) methacrylamide] (abbreviation: PTPDMA), or poly[N,N'-bis(4-butylphenyl)-N,N'-bis(phenyl)benzidine] (abbreviation: Poly-TPD). Alternatively, it is also possible to use a high molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS).

Alternatively, as the material with a high hole-injection property, a composite material containing a hole-transport material and an acceptor material (electron-accepting material) can be used. In that case, the acceptor material extracts electrons from the hole-transport material, so that holes are generated in the hole-injection layers (111, 111*a*, and 111*b*) and the holes are injected into the light-emitting layers (113, 113*a*, and 113*b*) through the hole-transport layers (112, 112*a*, and 112*b*). Note that each of the hole-injection layers (111, 111*a*, and 111*b*) may be formed as a single layer formed of a composite material containing a hole-transport material and an acceptor material (electron-accepting material), or may be formed by stacking a layer including a hole-transport material and a layer including an acceptor material (electron-accepting material).

The hole-transport layers (112, 112*a*, and 112*b*) are each a layer that transports the holes, which are injected from the first electrode 101 by the hole-injection layers (111, 111*a*, and 111*b*), to the light-emitting layers (113, 113*a*, and 113*b*). Note that the hole-transport layers (112, 112*a*, and 112*b*) are each a layer containing a hole-transport material. It is particularly preferable that the HOMO level of the hole-transport material used in the hole-transport layers (112, 112*a*, and 112*b*) be the same as or close to the HOMO level of the hole-injection layers (111, 111*a*, and 111*b*).

As the acceptor material used in the hole-injection layers (111, 111*a*, and 111*b*), an oxide of a metal belonging to any of Group 4 to Group 8 of the periodic table can be used. Specific examples include molybdenum oxide, vanadium oxide, niobium oxide, tantalum oxide, chromium oxide, tungsten oxide, manganese oxide, and rhenium oxide. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. As examples of ones having an electron-withdrawing group (halogen group or cyano group), 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyanonaphthoquinodimethane (abbreviation: F6-TCNNQ), and the like can be given. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile].

The hole-transport materials used in the hole-injection layers (111, 111*a*, and 111*b*) and the hole-transport layers (112, 112*a*, and 112*b*) are preferably substances with a hole mobility of higher than or equal to $10^{-6}$ cm$^2$/Vs. Note that other substances can be used as long as the substances have a hole-transport property higher than an electron-transport property.

As the hole-transport material, materials having a high hole-transport property, such as a π-electron rich heteroaromatic compound (e.g., a carbazole derivative, a furan derivative, and a thiophene derivative) and an aromatic amine (compound having an aromatic amine skeleton), are preferred.

Examples of the above carbazole derivative (a compound having a carbazole skeleton) include a bicarbazole derivative (e.g., a 3,3'-bicarbazole derivative) and an aromatic amine having a carbazolyl group.

Note that specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), 9-(2-naphthyl)-9'-phenyl-9H,9'H-3,3'-bicarbazole (abbreviation: βNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-

N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4''-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above thiophene derivative and the furan derivative include compounds having a thiophene skeleton, such as 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBT-FLP-III), and 4-[4-(9-phenyl-9H-fluoren-9-yl)phenyl]-6-phenyldibenzothiophene (abbreviation: DBTFLP-IV), and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4''-tris[N-(1-naphthyl)-N-phenylamino]triphenylamine (abbreviation: 1-TNATA), 4,4',4''-tris(N,N'-diphenylamino)triphenylamine (abbreviation: TDATA), 4,4',4''-tris[N-(3-methylphenyl)-N-phenylamino]triphenylamine (abbreviation: m-MTDATA), N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Furthermore, as the hole-transport material, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and one of or a combination of various known materials can be used as the hole-transport material for the hole-injection layers (111, 111a, and 111b) and the hole-transport layers (112, 112a, and 112b). Note that the hole-transport layers (112, 112a, and 112b) may each be formed of a plurality of layers. That is, a first hole-transport layer and a second hole-transport layer may be stacked, for example.

In the light-emitting element illustrated in FIG. 1, the light-emitting layer (113 or 113a) is formed over the hole-transport layer (112 or 112a) of the EL layer (103 or 103a) by a vacuum evaporation method. Note that in the case of the light-emitting element with the tandem structure illustrated in FIG. 1(D), after the EL layer 103a and the charge-generation layer 104 are formed, the light-emitting layer 113b is also formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance that exhibits emission color of blue, purple, bluish purple, green, yellowish green, yellow, orange, red, or the like is appropriately used. When the light-emitting layers (113a, 113b, and 113c) are formed using different light-emitting substances, different emission colors can be exhibited (for example, complementary emission colors are combined to obtain white light emission). Furthermore, a stacked-layer structure in which one light-emitting layer contains different light-emitting substances may be employed.

The light-emitting layers (113, 113a, 113b, and 113c) may each contain one or more kinds of organic compounds (a host material and the like) in addition to a light-emitting substance (guest material). As the one or more kinds of organic compounds, the organic compound of one embodiment of the present invention or one or both of the hole-transport material and the electron-transport material described in this embodiment can be used.

The light-emitting substance that can be used in the light-emitting layers (113, 113a, 113b, and 113c) is not particularly limited, and a light-emitting substance that converts singlet excitation energy into light emission in the visible light range or a light-emitting substance that converts triplet excitation energy into light emission in the visible light range can be used.

Examples of other light-emitting substances are given below.

As an example of the light-emitting substance that converts singlet excitation energy into light emission, a substance that emits fluorescence (fluorescent material) can be given; examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'- bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'''-(2-tert-butyl anthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit different emission colors (emission peaks) and thus, any of them is selected and used appropriately according to need.

As a phosphorescent material that exhibits blue or green and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-N$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)); and the like can be given.

As a phosphorescent material that exhibits green or yellow and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III)(abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation:[Ir(pq)$_2$(acac)]), bis[2-(2-pyridinyl-KN)phenyl-κC][2-(4-phenyl-2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As a phosphorescent material that exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III)

(abbreviation: [Ir(dlnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-KN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-N]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$O,O')iridium(III); platinum complexes such as 2,3,7,8,12,13,17,18-octaethyl-21H,23H-porphyrinplatinum(II)(abbreviation:[PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the like) used in the light-emitting layers (113, 113*a*, 113*b*, and 113*c*), one or more kinds of substances having a larger energy gap than the light-emitting substance (the guest material) are selected to be used.

Accordingly, in the case where the light-emitting substance used in the light-emitting layer (113, 113*a*, 113*b*, 113*c*) is a fluorescent material, an organic compound (host material) used in combination with the light-emitting substance is preferably an organic compound that has a high energy level in a singlet excited state and has a low energy level in a triplet excited state. Note that as the organic compound (host material) used in combination with the light-emitting substance, not only the organic compound described in Embodiment 1, which is one embodiment of the present invention, or the hole-transport material (described above) or an electron-transport material (described later), which are described in this embodiment, but also a bipolar material or the like can be used. When the organic compound described in Embodiment 1, which is one embodiment of the present invention, is used in a light-emitting layer (especially when used as a host material), initial degradation of the light-emitting element can be suppressed, leading to higher reliability.

In terms of a preferable combination with a light-emitting substance (a fluorescent material or a phosphorescent material), specific examples of the organic compounds are shown below though some of them overlap the specific examples shown above.

In the case where the light-emitting substance is a fluorescent material, examples of the organic compound (the host material) that can be used in combination with the light-emitting substance include condensed polycyclic aromatic compounds, such as an anthracene derivative, a tetracene derivative, a phenanthrene derivative, a pyrene derivative, a chrysene derivative, and a dibenzo[g,p]chrysene derivative. Furthermore, it is preferable to use the organic compound described in Embodiment 1, which is one embodiment of the present invention.

Specific examples of the organic compound (the host material) used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N,N',N',N''',N'''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}-anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS),9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the organic compound (the host material) used in combination with the light-emitting substance. In particular, the organic compound described in Embodiment 1, which is one embodiment of the present invention, is suitable. Note that in the case where a plurality of organic compounds (e.g., a first host material and a second host material (or an assist material)) are used in combination with a light-emitting substance in order to form an exciplex, the plurality of organic compounds are preferably mixed with a phosphorescent material.

Such a structure makes it possible to efficiently obtain light emission utilizing ExTET (Exciplex-Triplet Energy Transfer), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material). The organic compound of one embodiment of the present invention described in Embodiment 1 has a stable triplet excited state and thus is suitable for a host material in the case where the light-emitting substance is a phosphorescent material. In the case where an exciplex as described above is formed, the organic compound is suitable as the electron-transport material. Owing to its triplet excitation energy level, the organic compound is particularly suitable when used in combination with a phosphorescent material that emits green light.

In the case where the light-emitting substance is a phosphorescent material, examples of the organic compound (host material or assist material) that can be used in combination with the light-emitting substance include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a triazine derivative, a pyridine derivative, a bipyridine derivative, and a phenanthroline derivative.

Among the above-described compounds, the same compounds as those given above as specific examples of the hole-transport material are given as specific examples of the aromatic amine (a compound having an aromatic amine skeleton), which is an organic compound having a high hole-transport property.

Moreover, the same compounds as those given above as specific examples of the hole-transport material are given as specific examples of the carbazole derivative, which is an organic compound having a high hole-transport property.

Specific examples of the dibenzothiophene derivative and the dibenzofuran derivative, which are organic compounds having a high hole-transport property, include 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II).

Specific examples of zinc- and aluminum-based metal complexes, which are organic compounds having a high electron-transport property, include metal complexes having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), or the like can also be used.

Specific examples of the oxadiazole derivative, the triazole derivative, the benzimidazole derivative, the benzimidazole derivative, the quinoxaline derivative, the dibenzoquinoxaline derivative, and the phenanthroline derivative, which are organic compounds having a high electron-transport property, include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7),9-[4-(5-phenyl-1,3,4-oxadiazol-2-yl)phenyl]-9H-carbazole (abbreviation: CO11),3-(4-biphenylyl)-5-(4-tert-butylphenyl)-4-phenyl-1,2,4-triazole (abbreviation: TAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOS), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation:2mDBTBPDBq-II),2-[3'-(9H-carbazol-9-yl)biphenyl-3-yl]dibenzo[f,h]quinoxaline (abbreviation:2mCzBPDBq),2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation:6mDBTPDBq-II).

Specific examples of a heterocyclic compound having a diazine skeleton, a heterocyclic compound having a triazine skeleton, and a heterocyclic compound having a pyridine skeleton, which are organic compounds having a high electron-transport property, include 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB). Furthermore, in particular, the organic compound described in Embodiment 1, which is one embodiment of the present invention, can also be used.

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used as an organic compound having a high electron-transport property.

In the case where a plurality of organic compounds are used in the light-emitting layers (113, 113a, 113b, and 113c), two kinds of compounds that form an exciplex (a first compound and a second compound) and an organometallic complex may be mixed and used. In that case, various organic compounds can be combined appropriately to be used; to form an exciplex efficiently, it is particularly preferable to combine a compound that easily accepts holes (hole-transport material) and a compound that easily accepts electrons (electron-transport material). Note that, as specific examples of the hole-transport material and the electron-transport material, the materials described in this embodiment can be used. With the structure, high efficiency, low voltage, and a long lifetime can be achieved at the same time.

The TADF material refers to a material that can up-convert a triplet excited state into a singlet excited state (i.e., reverse intersystem crossing) using a little thermal energy and efficiently exhibits light emission (fluorescence) from the singlet excited state. As the condition under which the thermally activated delayed fluorescence is efficiently obtained, energy difference between the triplet excited level and the singlet excited level being greater than or equal to 0 eV and less than or equal to 0.2 eV, preferably greater than or equal to 0 eV and less than or equal to 0.1 eV can be given. Note that delayed fluorescence exhibited by the TADF material refers to light emission having a spectrum similar to that of normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. In addition, a metal-containing porphyrin containing magnesium (Mg), zinc (Zn), cadmium (Cd), tin (Sn), platinum (Pt), indium (In), palladium (Pd), or the like can be given. Examples of the metal-containing porphyrin include a protoporphyrin-tin fluoride complex (abbreviation: $SnF_2$ (Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Other than these, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can also be used in combination with another organic compound. In particular, the TADF material can be combined with the host materials, the hole-transport materials, and the electron-transport materials described above, and the organic compound of one embodiment of the present invention described in Embodiment 1 is preferably used as a host material for the TADF material.

Furthermore, when the above materials are used in combination with a low molecular material or a high molecular material, the above materials can be used to form the light-emitting layers (113, 113a, 113b, and 113c). For the deposition, a known method (an evaporation method, a coating method, a printing method, or the like) can be used as appropriate.

In the light-emitting element illustrated in FIG. 1, an electron-transport layer (114 or 114a) is formed over the light-emitting layer (113 or 113a) of the EL layer (103 or 103a). Note that in the case of the light-emitting element with the tandem structure illustrated in FIG. 1(D), after the EL layer 103a and the charge-generation layer 104 are formed, an electron-transport layer 114b is also formed over the light-emitting layer 113b of the EL layer 103b.

<Electron-Transport Layer>

The electron-transport layers (114, 114a, and 114b) are each a layer that transports the electrons, which are injected from the second electrode 102 by the electron-injection layers (115, 115a, and 115b), to the light-emitting layers (113, 113a, and 113b). Note that the electron-transport layers (114, 114a, and 114b) are each a layer containing an electron-transport material. It is preferable that the electron-transport materials used in the electron-transport layers (114, 114a, and 114b) be substances with an electron mobility of higher than or equal to $1\times10^{-6}$ $cm^2$/Vs. Note that other substances can be used as long as the substances have an electron-transport property higher than a hole-transport property. The organic compound of one embodiment of the present invention described in Embodiment 1 has an excellent electron-transport property and thus can also be used for an electron-transport layer.

As the electron-transport material, it is possible to use a material having a high electron-transport property, such as a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, or a π-electron deficient heteroaromatic compound such as a nitrogen-containing heteroaromatic compound.

Specific examples of the electron-transport material include metal complexes having a quinoline skeleton or a benzoquinoline skeleton, such as tris(8-quinolinolato)aluminum(III) (abbreviation: $Alq_3$), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), bis[2-(2-benzothiazolyl)phenolato]zinc(II) (abbreviation: ZnBTZ), and bis[2-(2-hydroxyphenyl)benzothiazolato]zinc(II) (abbreviation: $Zn(BTZ)_2$).

Other than metal complexes, any of the following can also be used: an oxadiazole derivative such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-5-(4-tert-butylphenyl)-4-phenyl-1,2,4-triazole (abbreviation: TAZ) and 3-(4-tert-butylphenyl)-4-(4-ethylphenyl)-5-(4-biphenylyl)-1,2,4-triazole (abbreviation: p-EtTAZ); an imidazole derivative (including a benzimidazole derivative) such as 2,2',2''-(1,3,5-benzenetriyl)tris(1-phenyl-1H-benzimidazole) (abbreviation: TPBI) and 2-[3-(dibenzothiophen-4-yl)phenyl]-1-phenyl-1H-benzimidazole (abbreviation: mDBT-BIm-II); an oxazole derivative such as 4,4'-bis(5-methylbenzoxazol-2-yl)stilbene (abbreviation: BzOS); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); a quinoxaline derivative or a dibenzoquinoxaline derivative such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation:2mDBTBPDBq-II),2-[3'-(9H-carbazol-9-yl)biphenyl-3-yl]dibenzo[f,h]quinoxaline (abbreviation:2mCzBPDBq),2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]

dibenzo[f,h]quinoxaline (abbreviation: 6mDBTPDBq-II); a pyridine derivative such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB); a pyrimidine derivative such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); and a triazine derivative such as 2-{4-[3-(N-phenyl-9H-carbazol-3-yl)-9H-carbazol-9-yl]phenyl}-4,6-diphenyl-1,3,5-triazine (abbreviation: PCCzPTzn). Furthermore, in particular, the organic compound described in Embodiment 1, which is one embodiment of the present invention, can also be used.

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Each of the electron-transport layers (114, 114a, and 114b) is not limited to a single layer, and may be a stack of two or more layers each made of any of the above substances.

In the light-emitting element illustrated in FIG. 1(D), the electron-injection layer 115a is formed over the electron-transport layer 114a of the EL layer 103a by a vacuum evaporation method. Subsequently, the EL layer 103a and the charge-generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) are each a layer containing a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound such as erbium fluoride (ErF$_3$) can be used. Electride may also be used for the electron-injection layers (115, 115a, and 115b). Examples of the electride include a substance in which electrons are added at high concentration to a mixed oxide of calcium and aluminum. Note that any of the substances used in the electron-transport layers (114, 114a, and 114b), which are given above, can also be used.

A composite material in which an organic compound and an electron donor (donor) are mixed may also be used in the electron-injection layers (115, 115a, and 115b). Such a composite material is excellent in an electron-injection property and an electron-transport property because electrons are generated in the organic compound by the electron donor. In this case, the organic compound is preferably a material excellent in transporting the generated electrons; specifically, for example, the above-mentioned electron-transport materials (metal complexes, heteroaromatic compounds, and the like) used in the electron-transport layers (114, 114a, and 114b) can be used. Any substance showing an electron-donating property with respect to the organic compound can serve as an electron donor. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. A Lewis base such as magnesium oxide can also be used. An organic compound such as tetrathiafulvalene (abbreviation: TTF) can also be used.

Note that in the case where light obtained from the light-emitting layer 113b is amplified in the light-emitting element illustrated in FIG. 1(D), the optical path length between the second electrode 102 and the light-emitting layer 113b is preferably less than one fourth of the wavelength λ of light emitted from the light-emitting layer 113b. In that case, the optical path length can be adjusted by changing the thickness of the electron-transport layer 114b or the electron-injection layer 115b.

<Charge-Generation Layer>

In the light-emitting element illustrated in FIG. 1(D), the charge-generation layer 104 has a function of injecting electrons into the EL layer 103a and injecting holes into the EL layer 103b when voltage is applied between the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage in the case where the EL layers are stacked.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoroquinodimethane (abbreviation: F$_4$-TCNQ), chloranil, and the like can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, and the like can be given.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1(E) has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

Note that for fabrication of the light-emitting element described in this embodiment, a vacuum process such as an evaporation method or a solution process such as a spin coating method or an ink-jet method can be used. In the case where an evaporation method is used, a physical vapor deposition method (PVD method) such as a sputtering method, an ion plating method, an ion beam evaporation method, a molecular beam evaporation method, or a vacuum evaporation method; a chemical vapor deposition method (CVD method); or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers and the charge-generation layers (104, 104a, and 104b) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, a micro-contact printing method, or a nanoinprinting method), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers (103, 103a, and 103b) and the charge-generation layers (104, 104a, and 104b) of the light-emitting element described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. Note that as the quantum dot material, a colloidal quantum dot material, an alloyed quantum dot material, a core-shell quantum dot material, a core quantum dot material, or the like can be used.

The structure described in this embodiment can be used in an appropriate combination with any of the structures described in the other embodiments.

Embodiment 3

In this embodiment, a light-emitting device of one embodiment of the present invention will be described. Note that a light-emitting device illustrated in FIG. 2(A) is an active-matrix light-emitting device in which transistors (FETs) 202 over a first substrate 201 are electrically connected to light-emitting elements (203R, 203G, 203B, and 203W); the light-emitting elements (203R, 203G, 203B, and 203W) include a common EL layer 204 and each have a microcavity structure in which the optical path length between electrodes of each light-emitting element is adjusted according to the emission color of the light-emitting element. In addition, the light-emitting device is a top-emission light-emitting device in which light is emitted from the EL layer 204 through color filters (206R, 206G, and 206B) formed on a second substrate 205.

In the light-emitting device illustrated in FIG. 2(A), the first electrode 207 is formed so as to function as a reflective electrode. The second electrode 208 is formed so as to function as a semi-transmissive and semi-reflective electrode. Note that description in any of the other embodiments can be referred to for electrode materials forming the first electrode 207 and the second electrode 208 and appropriate materials can be used.

In the case where the light-emitting element 203R is a red-light-emitting element, the light-emitting element 203G is a green-light-emitting element, the light-emitting element 203B is a blue-light-emitting element, and the light-emitting element 203W is a white-light-emitting element in FIG. 2(A), for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2(B). Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2(B).

The color filters (206R, 206G, and 206B) are formed on the second substrate 205. Note that the color filters each transmit visible light in a specific wavelength range and blocks visible light in a specific wavelength range. Thus, as illustrated in FIG. 2(A), the color filter 206R that transmits only light in the red wavelength range is provided in a position overlapping with the light-emitting element 203R, whereby red light emission can be obtained from the light-emitting element 203R. The color filter 206G that transmits only light in the green wavelength range is provided in a position overlapping with the light-emitting element 203G, whereby green light emission can be obtained from the light-emitting element 203G. The color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of one type of color filter. The color filters (206R, 206G, and 206B) and the black layer 209 may be covered with an overcoat layer using a transparent material.

Although the light-emitting device illustrated in FIG. 2(A) has a structure in which light is extracted from the second substrate 205 side (top emission structure), the light-emitting device may have a structure in which light is extracted from the first substrate 201 side where the FETs 202 are formed (bottom emission structure) as illustrated in FIG. 2(C). For a bottom-emission light-emitting device, the first electrode 207 is formed so as to function as a semi-transmissive and semi-reflective electrode and the second electrode 208 is formed so as to function as a reflective electrode. As the first substrate 201, a substrate having at least a light-transmitting property is used. As illustrated in FIG. 2(C), color filters (206R', 206G', and 206B') are provided closer to the first substrate 201 than the light-emitting elements (203R, 203G, and 203B) are.

FIG. 2(A) illustrates the case where the light-emitting elements are the red-light-emitting element, the green-light-emitting element, the blue-light-emitting element, and the white-light-emitting element; however, the light-emitting elements of embodiments of the present invention are not limited to the above structures, and a yellow-light-emitting element or an orange-light-emitting element may be included. Note that description in any of the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting elements and appropriate materials can be used. In that case, a color filter needs to be appropriately selected according to the emission color of the light-emitting element.

With the above structure, a light-emitting device including light-emitting elements that exhibit a plurality of emission colors can be obtained.

Note that the structures described in this embodiment can be used in an appropriate combination with any of the structures described in the other embodiments.

Embodiment 4

In this embodiment, a light-emitting device of one embodiment of the present invention will be described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is included in one embodiment of the present invention. Note that any of the light-emitting elements described in the other embodiments can be used in the light-emitting device described in this embodiment.

In this embodiment, an active-matrix light-emitting device will be described with reference to FIG. 3.

Figure 3A:
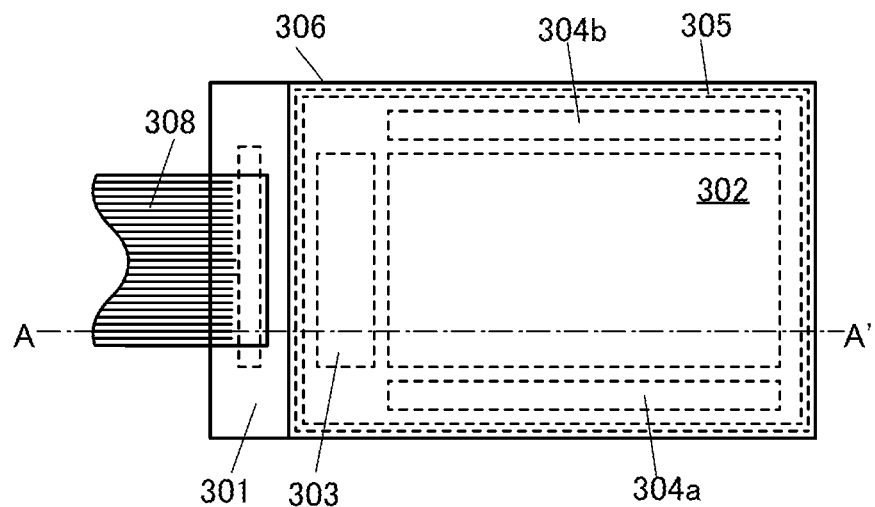
FIGS. 3A and 3B are drawings illustrating a light-emitting device.
Figure 3B:
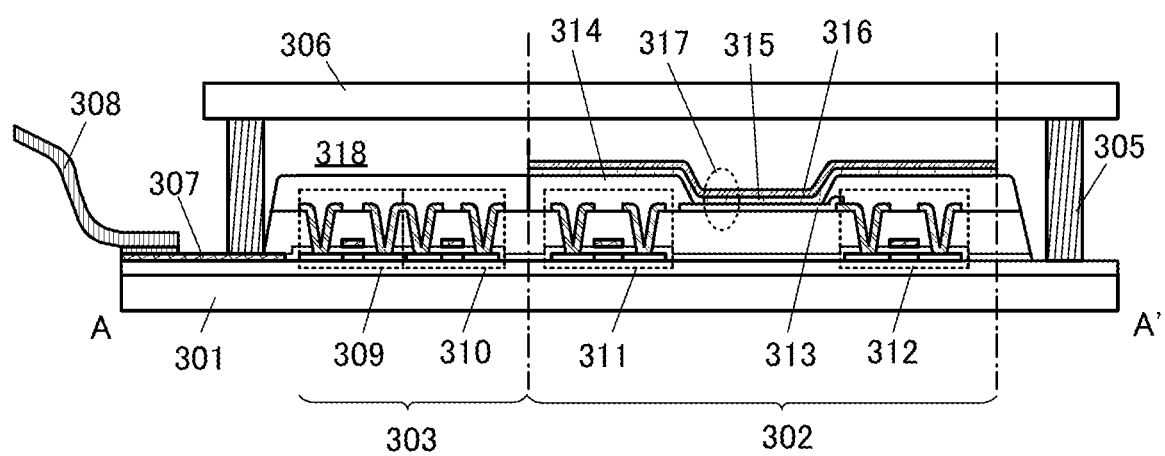

FIG. 3(A) is a top view illustrating a light-emitting device, and FIG. 3(B) is a cross-sectional view taken along a chain line A-A' in FIG. 3(A). The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 which is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

Next, FIG. 3(B) illustrates the cross-sectional structure.

The pixel portion 302 is made up of a plurality of pixels each of which includes an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity can suppress deterioration of the transistor characteristics, which is preferable.

For these semiconductors, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting element 317 described in this embodiment. Although not illustrated here, the second electrode 316 is electrically connected to the FPC 308 which is an external input terminal.

Although the cross-sectional view illustrated in FIG. 3(B) illustrates only one light-emitting element 317, a plurality of light-emitting elements are arranged in a matrix in the pixel portion 302. Light-emitting elements from which light of three kinds of colors (R, G, and B) are obtained are selectively formed in the pixel portion 302, whereby a light-emitting device capable of full-color display can be formed. In addition to the light-emitting elements from which light of three kinds of colors (R, G, and B) are obtained, for example, light-emitting elements from which light of white (W), yellow (Y), magenta (M), cyan (C), and the like are obtained may be formed. For example, the light-emitting elements from which light of some of the above colors are obtained are added to the light-emitting elements from which light of three kinds of colors (R, G, and B) are obtained, whereby effects such as an improvement in color purity and a reduction in power consumption can be obtained. Alternatively, a light-emitting device that is capable of full-color display may be fabricated by a combination with color filters. As the kinds of color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin or glass frit can be used for the sealant 305. It is preferable to use a material that is permeable to as little moisture and oxygen as possible for the sealant 305. As the second substrate 306, a material that can be used as the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting device can be obtained.

In the case where the active-matrix light-emitting device is formed over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser irradiation, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupro, rayon, or regenerated polyester), or the like), a leather substrate, and a rubber substrate. With the use of any of these substrates, high durability, high heat resistance, a reduction in weight, and a reduction in thickness can be achieved.

Note that the structures described in this embodiment can be used in an appropriate combination with the structures described in the other embodiments.

Embodiment 5

In this embodiment, examples of a variety of electronic devices and an automobile completed using the light-emitting element of one embodiment of the present invention or a light-emitting device including the light-emitting element of one embodiment of the present invention are described. Note that the light-emitting device can be used mainly in a display portion of the electronic device described in this embodiment.

Figure 4A:
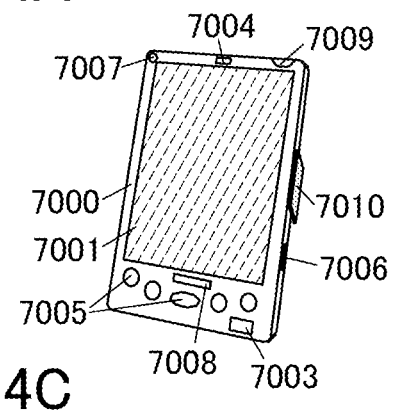
FIGS. 4A-4G are drawings illustrating electronic devices.
Figure 4B:
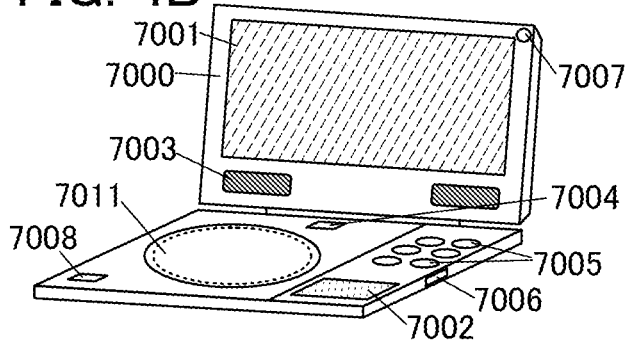
Figure 4C:
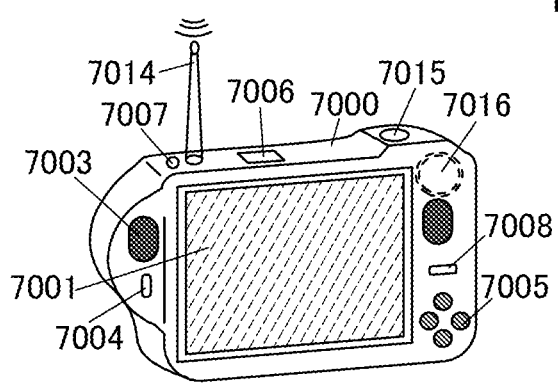

Electronic devices illustrated in FIG. 4(A) to FIG. 4(C) can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4(A) is a mobile computer which can include a switch 7009, an infrared port 7010, and the like in addition to the above components.

FIG. 4(B) is a portable image reproducing device (e.g., a DVD player) which is provided with a recording medium and can include a second display portion 7002, a recording medium reading portion 7011, and the like in addition to the above components.

FIG. 4(C) is a digital camera with a television reception function, which can include an antenna 7014, a shutter button 7015, an image receiving portion 7016, and the like in addition to the above components.

Figure 4D:
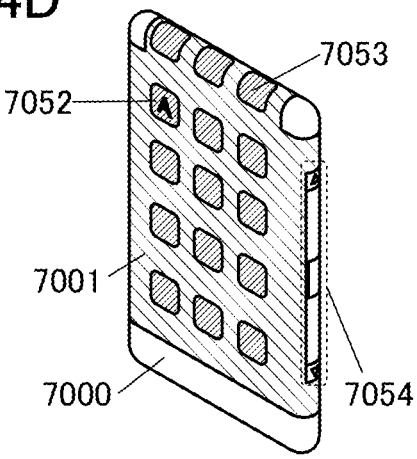

FIG. 4(D) is a portable information terminal. The portable information terminal has a function of displaying information on three or more surfaces of the display portion 7001. Here, an example in which information 7052, information 7053, and information 7054 are displayed on different surfaces is shown. For example, the user can check the information 7053 displayed in a position that can be observed from above the portable information terminal, with the portable information terminal put in a breast pocket of his/her clothes. The user can see the display without taking out the portable information terminal from the pocket and decide whether to answer the call, for example.

Figure 4E:
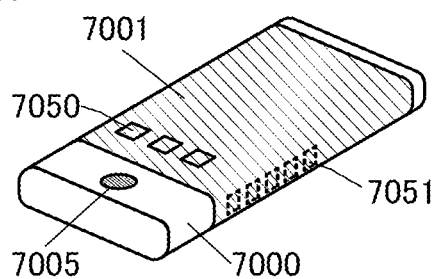

FIG. 4(E) is a portable information terminal (e.g., a smartphone) and can include the display portion 7001, the operation key 7005, and the like in the housing 7000. Note that the speaker 7003, the connection terminal 7006, the sensor 7007, or the like may be provided in the portable information terminal. The portable information terminal can display characters and image information on its plurality of surfaces. Here, an example is shown in which three icons 7050 are displayed. Information 7051 indicated by dashed rectangles can be displayed on another surface of the display portion 7001. Examples of the information 7051 include notification of reception of an e-mail, SNS, or an incoming call, the title and sender of an e-mail, SNS, or the like, the date, the time, remaining battery, and the reception strength of an antenna. Alternatively, the icon 7050 or the like may be displayed in the position where the information 7051 is displayed.

Figure 4F:
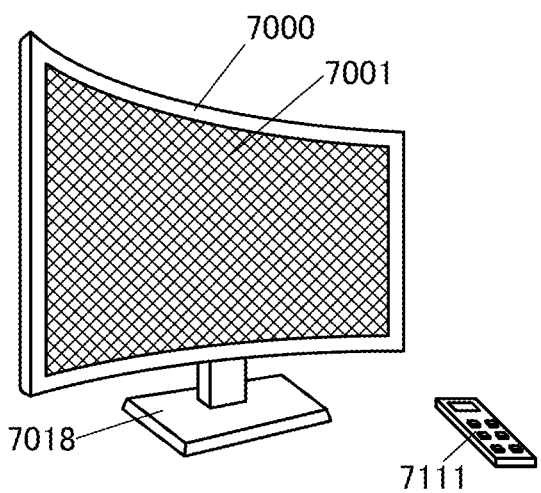

FIG. 4(F) is a large-size television set (also referred to as TV or a television receiver), which can include the housing 7000, the display portion 7001, and the like. In addition, shown here is a structure where the housing 7000 is supported by a stand 7018. The television set can be operated with a separate remote controller 7111 or the like. Note that the display portion 7001 may include a touch sensor, in which case the television set may be operated by touch on the display portion 7001 with a finger or the like. The remote controller 7111 may be provided with a display portion for displaying data output from the remote controller 7111. With operation keys or a touch panel provided in the remote controller 7111, channels and volume can be operated and images displayed on the display portion 7001 can be operated.

The electronic devices illustrated in FIG. 4(A) to FIG. 4(F) can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image data mainly on one display portion while displaying text data mainly on the other display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that the electronic devices illustrated in FIG. 4(A) to FIG. 4(F) can have are not limited to those, and the electronic devices can have a variety of functions.

Figure 4G:
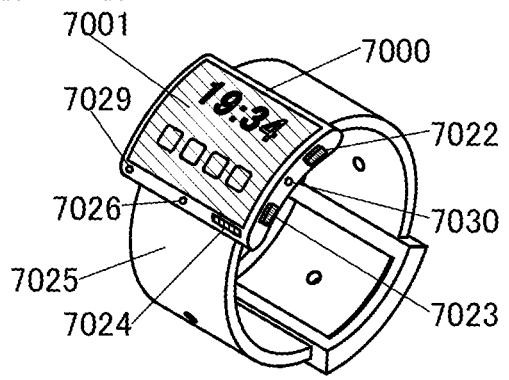

FIG. 4(G) is a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is bent, and display can be performed on the bent display surface. Furthermore, mutual communication between the portable information terminal and, for example, a headset capable of wireless communication can be performed, and thus hands-free calling is possible with the portable information terminal. With the connection terminal 7024, the portable information terminal can perform mutual data transmission with another information terminal and charging. Wireless power feeding can also be employed for the charging operation.

The display portion 7001 mounted in the housing 7000 also serving as a bezel includes a non-rectangular display region. The display portion 7001 can display an icon indicating time, another icon, and the like. The display portion 7001 may be a touch panel (input/output device) including a touch sensor (input device).

Note that the smart watch illustrated in FIG. 4(G) can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting device of one embodiment of the present invention and the display device including the light-emitting element of one embodiment of the present invention can be used in the display portions of the electronic devices described in this embodiment, enabling the electronic devices to have a long lifetime.

Figure 5A:
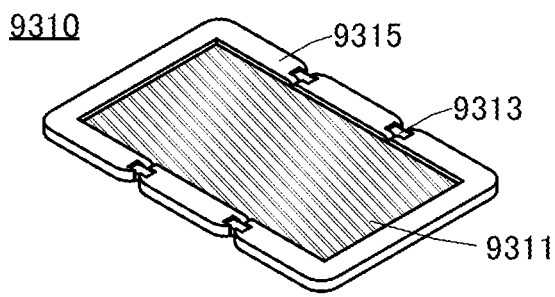
FIGS. 5A-5C are drawings illustrating an electronic device.
Figure 5B:
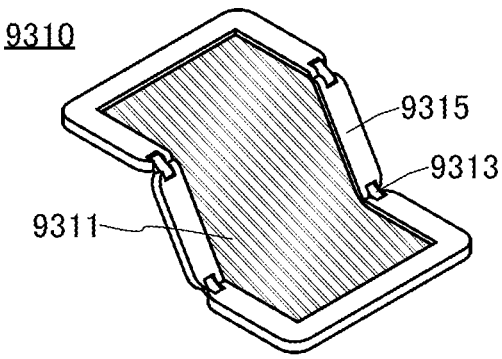
Figure 5C:
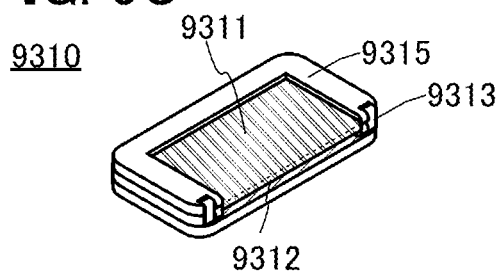

Another electronic device including the light-emitting device is a foldable portable information terminal illustrated in FIGS. 5(A) to 5(C). FIG. 5(A) illustrates a portable information terminal 9310 which is opened. FIG. 5(B) illustrates the portable information terminal 9310 in a state in the middle of change from one of an opened state and a folded state to the other. FIG. 5(C) illustrates the portable information terminal 9310 which is folded. The portable information terminal 9310 is excellent in portability when folded, and is excellent in display browsability when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a portion between two housings 9315 with the use of the hinges 9313, the portable information terminal 9310 can be reversibly changed in shape from an opened state to a folded state. The light-emitting device of one embodiment of the present invention can be used for the display portion 9311. In addition, an electronic device having along lifetime can be provided. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of an application can be smoothly performed.

Figure 6A:
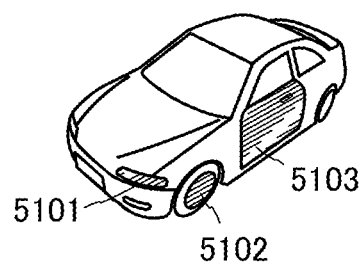
FIGS. 6A and 6B are drawings illustrating an automobile.
Figure 6B:
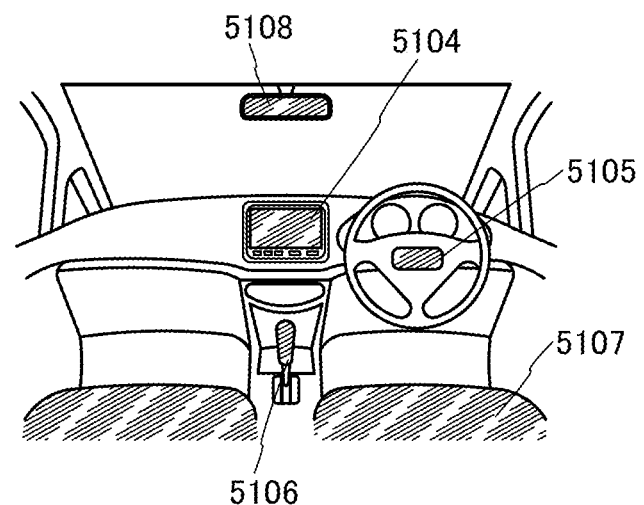

FIGS. 6(A) and 6(B) illustrate an automobile including the light-emitting device. In other words, the light-emitting device can be integrated into an automobile. Specifically, the light-emitting device can be applied to lights 5101 (including lights of the rear part of the car), a wheel 5102, a part or the whole of a door 5103, or the like on the outer side of the automobile which is illustrated in FIG. 6(A). The light-emitting device can also be applied to a display portion 5104, a steering wheel 5105, a shifter 5106, a seat 5107, an inner rearview mirror 5108, or the like on the inner side of the automobile which is illustrated in FIG. 6(B). Apart from that, the light-emitting device may be used for a part of the glass window.

In the above manner, the electronic devices and automobiles in which the light-emitting device or the display device of one embodiment of the present invention is used can be obtained. In that case, a long-lifetime electronic device can be obtained. Note that the light-emitting device or the display device can be used for electronic devices and automobiles in a variety of fields without being limited to those described in this embodiment.

Note that the structures described in this embodiment can be used in an appropriate combination with any of the structures described in the other embodiments.

Embodiment 6

In this embodiment, the structure of a lighting device fabricated using the light-emitting device of one embodiment of the present invention or the light-emitting element which is part of the light-emitting device will be described with reference to FIG. 7.

Figure 7A:
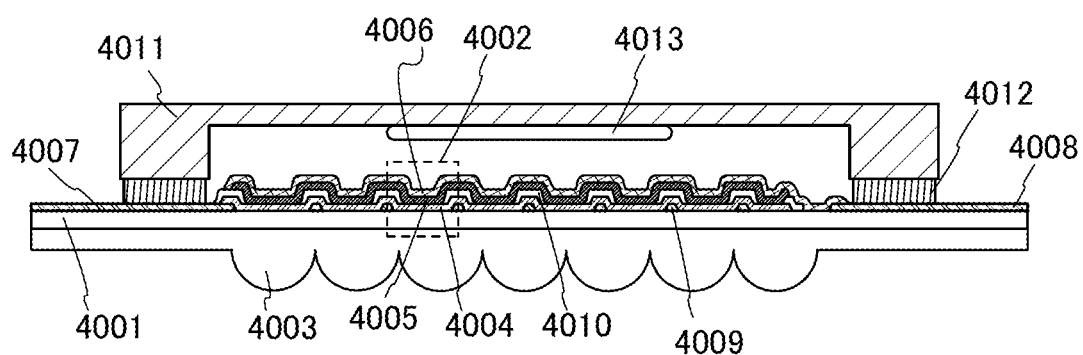
FIGS. 7A and 7B are drawings illustrating lighting devices.
Figure 7B:
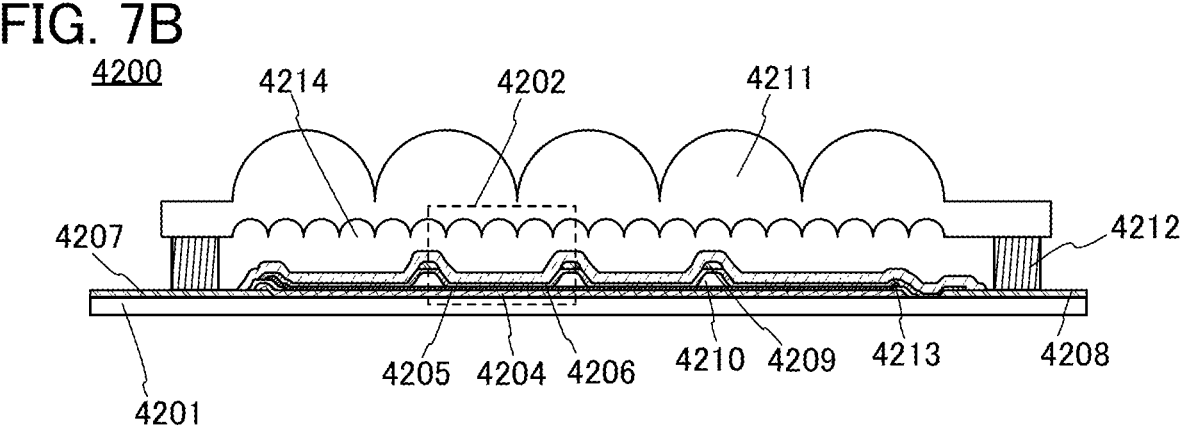

FIGS. 7(A) and 7(B) show examples of cross-sectional views of lighting devices. FIG. 7(A) is a bottom-emission lighting device in which light is extracted from the substrate side, and FIG. 7(B) is a top-emission lighting device in which light is extracted from the sealing substrate side.

A lighting device 4000 illustrated in FIG. 7(A) includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7(A), whereby the extraction efficiency of light generated in the light-emitting element 4002 can be increased.

A lighting device 4200 illustrated in FIG. 7(B) includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7(B), whereby the extraction efficiency of light generated in the light-emitting element 4202 can be increased.

Application examples of such lighting devices include a ceiling light for indoor lighting. Examples of the ceiling light include a ceiling direct mount light and a ceiling embedded light. Such a lighting device is fabricated using the light-emitting device and a housing or a cover in combination.

For another example, such lighting devices can be used for a foot light that illuminates a floor so that safety on the floor can be improved. For example, the foot light can be effectively used in a bedroom, on a staircase, or on a passage. In that case, the size or shape of the foot light can be changed depending on the area or structure of a room.

The foot light can be a stationary lighting device fabricated using the light-emitting device and a support base in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, the light-emitting device which is one embodiment of the present invention or the light-emitting element which is a part of the light-emitting device can be used as part of furniture in a room, so that a lighting device which has a function of the furniture can be obtained.

As described above, a variety of lighting devices that include the light-emitting device can be obtained. Note that these lighting devices are also embodiments of the present invention.

The structures described in this embodiment can be used in an appropriate combination with the structures described in the other embodiments.

Example 1

Synthesis Example 1

In this example, a synthesis method of 4-[3-(dibenzothiophen-4-yl)phenyl]-8-phenyl-[1]benzofuro[3,2-d]pyrimidine (abbreviation: 8Ph-4mDBtPBfpm), which is an organic compound of one embodiment of the present invention represented by Structural Formula (100) in Embodiment 1, will be described. Note that the structure of 8Ph-4mDBtPBfpm is shown below.

[Chemical Formula 19]

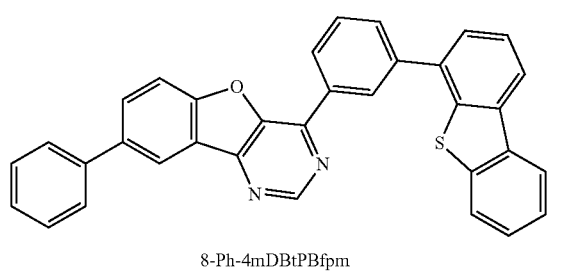

(100)

8-Ph-4mDBtPBfpm

Synthesis of 4-[3-(dibenzothiophen-4-yl)phenyl]-8-phenyl-[1]benzofuro[3,2-d]pyrimidine Into a three-neck flask, 3.00 g of 8-chloro-4-[3-(dibenzothiophen-4-yl)phenyl]-[1]benzofuro[3,2-d]pyrimidine, 0.95 g of a phenylboronic acid, 4.12 g of tripotassium phosphate, 65 mL of diglyme, and 1.44 g of t-butanol were put, they were degassed by being stirred under reduced pressure, and the air in the flask was replaced with nitrogen. To this mixture, 42.7 mg of palladium(II) acetate and 140 mg of di(1-adamantyl)-n-butylphosphine were added, followed by stirring at 120° C. for 15.5 hours.

To this reaction liquid, 45.2 mg of palladium(II) acetate and 140 mg of di(1-adamantyl)-n-butylphosphine were added, followed by stirring at 120° C. for 6 hours and then at 140° C. for 3 hours. Water was added to this reaction liquid, suction filtration was performed, and the resulting residue was washed with ethyl acetate and hexane. This residue was dissolved in heated toluene, followed by filtration through a filter aid filled with Celite, alumina, and Celite in this order. The obtained solution was concentrated and dried, and then recrystallized with toluene to give 1.50 g of a white solid containing a target substance.

By a train sublimation method, 1.50 g of the obtained white solid was sublimated and purified. The conditions of the sublimation purification were such that the solid was heated under a pressure of 3.48 Pa at 280° C. while the argon gas was made to flow at a flow rate of 15 mL/min. After the purification by sublimation, a target substance was obtained (1.02 g of a white solid, collection rate: 68%). This synthesis scheme is shown in the following formula (a-1).

[Chemical Formula 20]

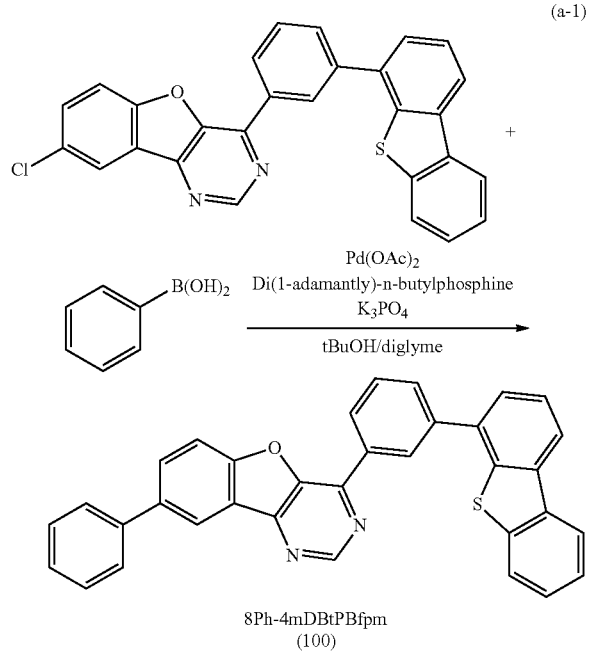

(a-1)

8Ph-4mDBtPBfpm
(100)

Figure 8:
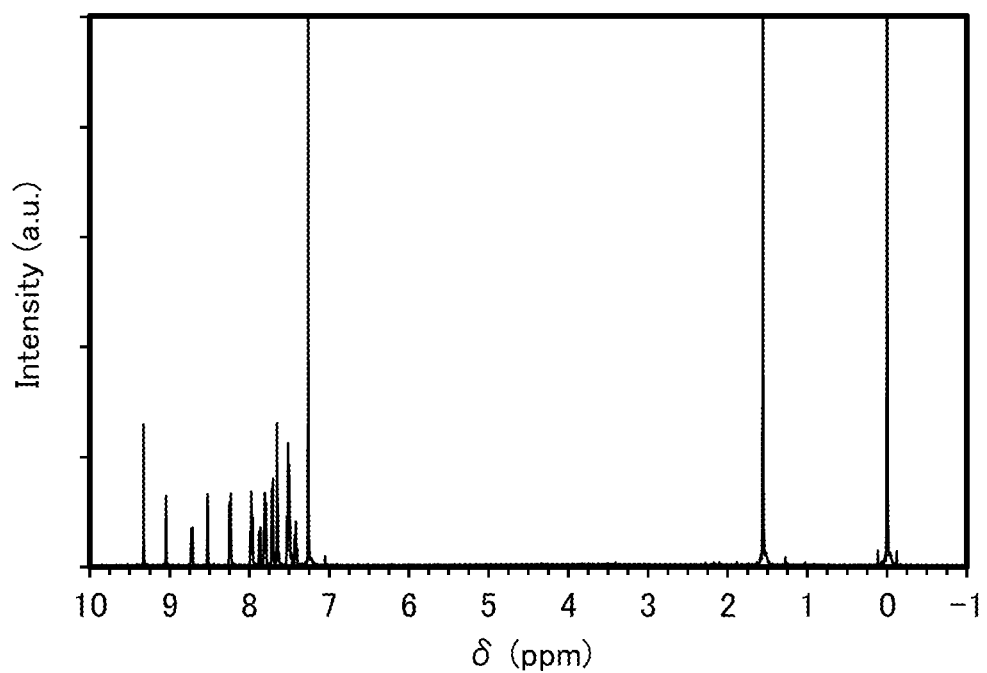
FIG. 8 is a $_1$H-NMR chart of an organic compound represented by Structural Formula (100).

Analysis results by nuclear magnetic resonance (H-NMR) spectroscopy of the white solid obtained in the above-described reaction are shown below. FIG. 8 shows a $^1$H-NMR chart. The results reveal that 8Ph-4mDBtPBfpm, the above-described organic compound of one embodiment of the present invention represented by Structural Formula (100), was obtained in this example.

$^1$H-NMR. δ (CDCl$_3$): 7.42 (t, 1H), 7.49-7.53 (m, 4H), 7.64-7.66 (m, 2H), 7.71 (d, 2H), 7.79-7.82 (m, 2H), 7.87 (d, 1H), 7.97 (t, 2H), 8.23-8.25 (m, 2H), 8.52 (s, 1H), 8.72 (d, 1H), 9.05 (s, 1H), 9.33 (s, 1H).

<<Physical Properties of 8 pH-4mDBtPBfpm>>

Next, the ultraviolet-visible absorption spectra (hereinafter, simply referred to as "absorption spectra") and emission spectra of a toluene solution and a solid thin film of 8Ph-4mDBtPBfpm were measured.

Figure 9A:
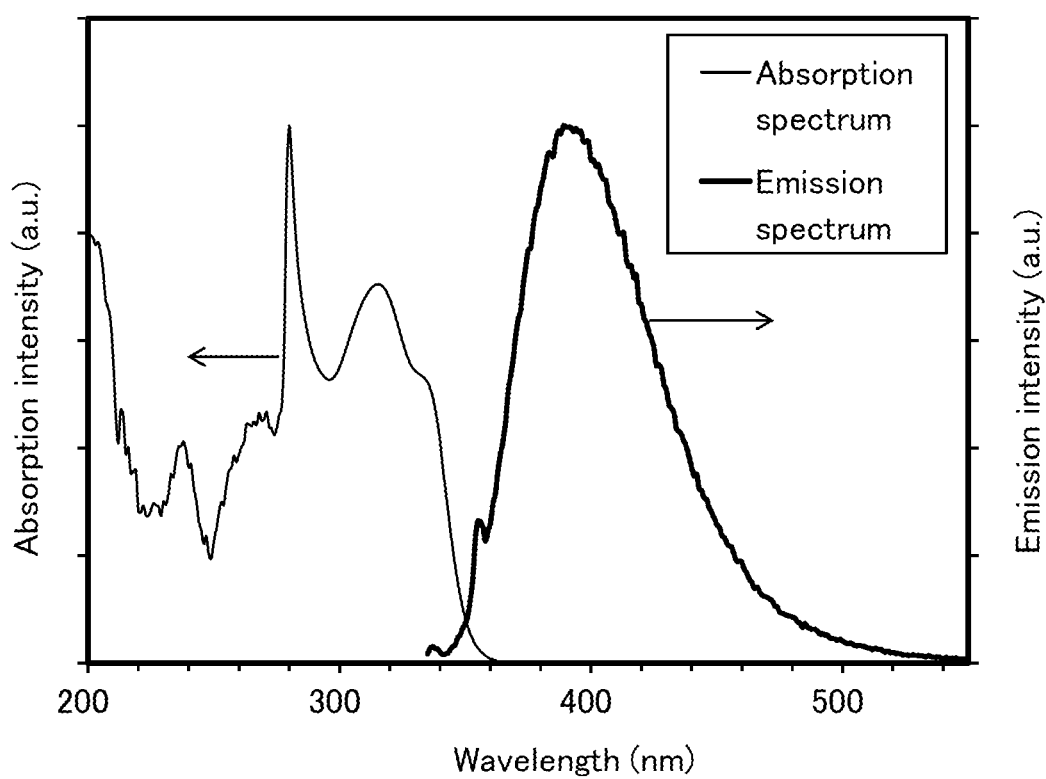
FIGS. 9A and 9B are ultraviolet-visible absorption spectra and emission spectra of the organic compound represented by Structural Formula (100).

The absorption spectrum in the toluene solution was measured with an ultraviolet-visible spectrophotometer (V550, produced by JASCO Corporation). The emission spectrum in the toluene solution was measured with a fluorescence spectrophotometer (FS920, manufactured by Hamamatsu Photonics K.K.). FIG. 9(A) shows the obtained measurement results of the absorption spectrum and the emission spectrum of the toluene solution. The horizontal axis represents wavelength and the vertical axes represent absorption intensity and emission intensity.

As can be seen in FIG. 9(A), 8Ph-4mDBtPBfpm in the toluene solution exhibited absorption peaks at approximately 335 nm, 316 nm, and 280 nm and an emission wavelength peak at 389 nm (excitation wavelength: 320 nm).

Figure 9B:
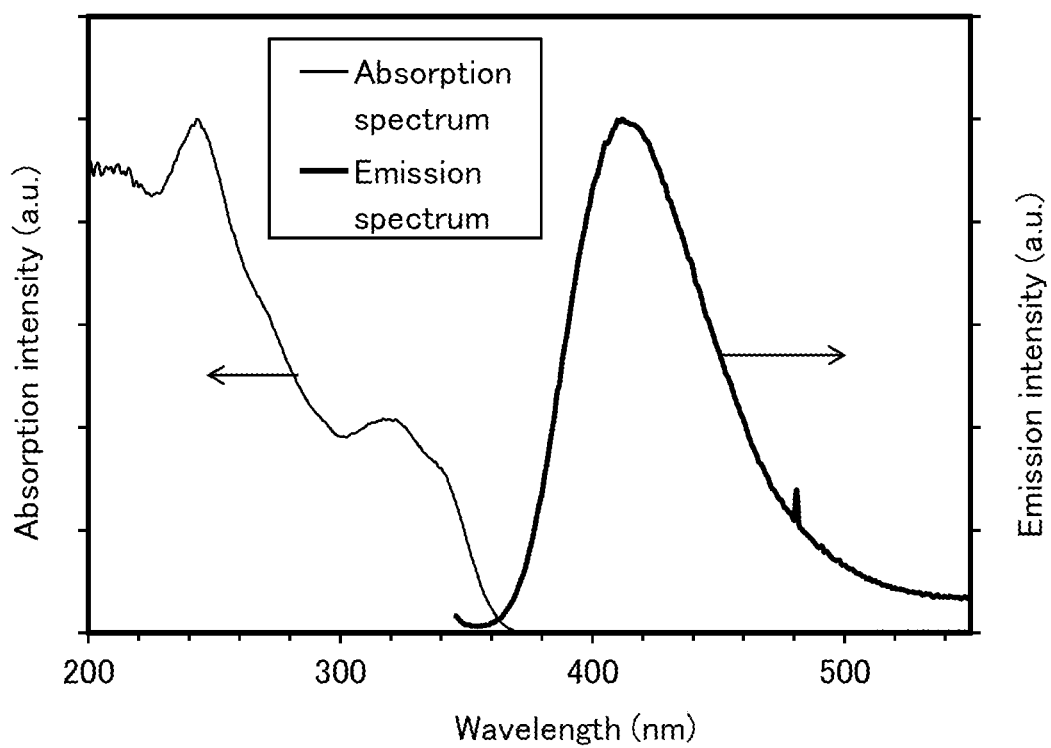

In the measurement of the absorption spectrum of the solid thin film, the solid thin film formed on a quartz substrate by a vacuum evaporation method was used and measurement was performed with an ultraviolet-visible spectrophotometer (U-4100, manufactured by Hitachi High-Technologies Corporation). In the measurement of the emission spectrum of the solid thin film, the solid thin film similar to the above was used and measurement was performed with a fluorescence spectrophotometer (FS920 manufactured by Hamamatsu Photonics K.K.). FIG. 9(B) shows the obtained measurement results of the absorption spectrum and emission spectrum of the solid thin film. The horizontal axis represents wavelength and the vertical axes represent absorption intensity and emission intensity.

As can be seen in FIG. 9(B), 8Ph-4mDBtPBfpm of the solid thin film exhibited absorption peaks at approximately 342 nm, 320 nm, and 243 nm and an emission wavelength peak at 412 nm (excitation wavelength: 340 nm).

The organic compound of one embodiment of the present invention, 8Ph-4mDBtPBfpm, has a high T1 level and thus is a host material suitable for a phosphorescent material (guest material) which emits light in the vicinity of blue to yellow regions. Note that 8Ph-4mDBtPBfpm, the organic compound of one embodiment of the present invention, can also be used as a host material for a substance that emits phosphorescence in the visible region or a light-emitting substance.

Example 2

Synthesis Example 2

In this example, a synthesis method of 4-[3'-(dibenzothiophen-4-yl)biphenyl-3-yl]-8-phenyl-[1]benzofuro[3,2-d]pyrimidine (abbreviation: 8Ph-4mDBtBPBfpm), which is an organic compound of one embodiment of the present invention represented by Structural Formula (101) in Embodiment 1, will be described. Note that the structure of 8Ph-4mDBtBPBfpm is shown below.

[Chemical Formula 21]

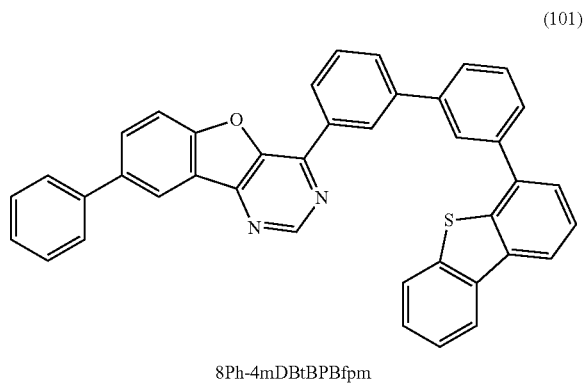

(101)

8Ph-4mDBtBPBfpm

Step 1: Synthesis of 2-hydroxy-5-phenylbenzonitrile

Into a three-neck flask, 1.57 g of a phenylboronic acid, 2.30 g of 5-bromo-2-hydroxybenzonitrile, 3.21 g of potassium carbonate, 43.5 mL of toluene, 14.5 mL of ethanol, and 11.6 mL of water were put, they were degassed by being stirred under reduced pressure, and the air was replaced with nitrogen.

To this mixture, 53.0 mg of palladium(II) acetate and 0.142 g of tris(2-methylphenyl)phosphine (abbreviation: P(o-tol)$_3$) were added, followed by stirring at 100° C. for 8 hours. Water was added to the obtained reaction liquid, and extraction with ethyl acetate was performed. The obtained organic layer was washed with water and a saturated aqueous solution of sodium chloride, and dried with magnesium sulfate.

This mixture was subjected to gravity filtration and the filtrate was concentrated to give a pale brown solid. Heated toluene was added to the obtained solid and filtered through a filter aid filled with Celite, alumina, and Celite in this order. The residue precipitated at this time was dissolved in a mixed solvent of ethyl acetate, dichloromethane, and methanol, followed by filtration through a filter aid filled with Celite, alumina, and Celite in this order. The obtained solution was concentrated and dried to give 1.86 g of a target light brown solid in a yield of 82%. This synthesis scheme is shown in the following formula (b-1).

[Chemical Formula 22]

Step 2: Synthesis of ethyl 3-amino-5-phenylbenzo[b]furan-2-carboxylate

Next, 1.86 g of 2-hydroxy-5-phenylbenzonitrile, which is the target substance obtained in the above Step 1, and 2.65 g of potassium carbonate were put into a three-neck flask, and the air was replaced with nitrogen. To this mixture, 1.91 g of ethyl bromoacetate and 12 mL of N,N-dimethylformamide were added, followed by stirring at 100° C. for 14 hours. The obtained reaction substance was put into iced water, stirred for 1 hour, and subjected to suction filtration to give a residue. The obtained residue was washed with water to give 2.13 g of a target brown solid in a yield of 80%. This synthesis scheme is shown in the following formula (b-2).

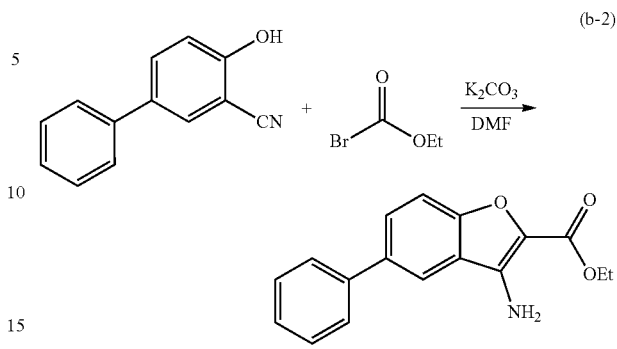

[Chemical Formula 23]

Step 3: Synthesis of 8-phenyl[1]benzofuro[3,2-d]pyrimidin-4(3)-one

Next, 2.13 g of 3-amino-5-phenylbenzo[b]furan-2-carboxylate, which is the target substance obtained in the above Step 2, and 11 mL of formamide were put into a recovery flask and heated at 150° C. To this mixture, 1.59 g of formamidine acetate was added, followed by stirring at 160° C. for 14.5 hours. Water was added to the obtained reaction substance, suction filtration was performed, and the resulting residue was washed with toluene and hexane to give 1.86 g of a target light brown solid in a yield of 94%. This synthesis scheme is shown in the following formula (b-3).

[Chemical Formula 24]

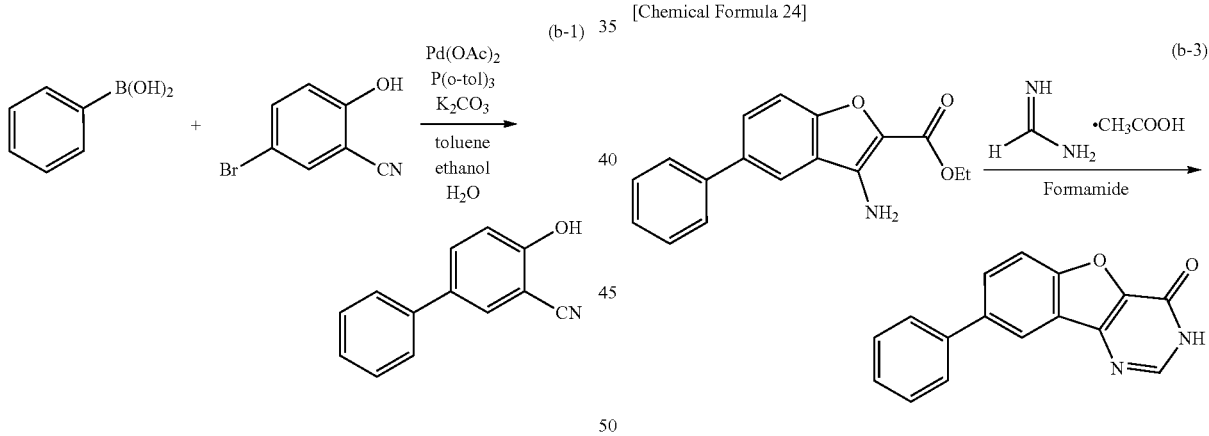

Step 4: Synthesis of 4-chloro-8-phenyl[1]benzofuro[3,2-d]pyrimidine

Next, 1.86 g of 8-phenyl[1]benzofuro[3,2-d]pyrimidin-4(3H)-one, which is the target substance obtained in the above Step 3, and 0.05 mL of N,N-dimethylformamide were put into a three-neck flask and stirred. To this mixture, 10.7 g of phosphoryl chloride was added, followed by stirring at 90° C. for 17 hours. The obtained reaction substance was put into iced water, neutralized with sodium hydroxide and a saturated aqueous solution of sodium bicarbonate, and stirred for 1 hour. This mixture was subjected to suction filtration, and the resulting residue was washed with ethanol to give 1.84 g of a target ocher solid in a yield of 92%. This synthesis scheme is shown in the following formula (b-4).

[Chemical Formula 25]

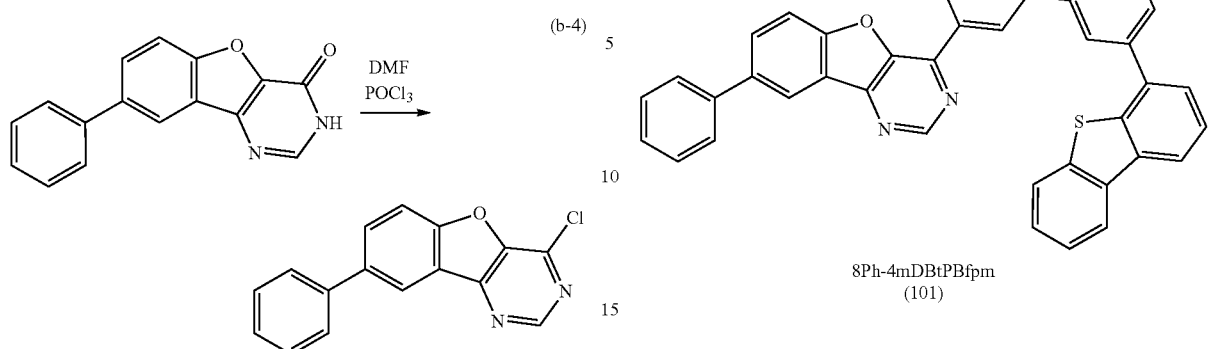

Step 5: Synthesis of 4-[3'-(dibenzothiophen-4-yl)biphenyl-3-yl]-8-phenyl-[1]benzofuro[3,2-d]pyrimidine Next, 1.00 g of 4-chloro-8-phenyl[1]benzofuro[3,2-d]pyrimidine, which is obtained in the above Step 4, 1.52 g of 3'-(dibenzothiophen-4-yl)-1,1'-biphenyl-3-ylboronic acid, 0.997 g of potassium carbonate, 13.5 mL of toluene, 4.5 mL of ethanol, and 3.6 mL of water were put into a three-neck flask, they were degassed by being stirred under reduced pressure, and the air was replaced with nitrogen.

To this mixture, 129 mg of tetrakis(triphenylphosphine)palladium(0) was added, followed by stirring at 100° C. for 6.5 hours. Water was added to the obtained reaction substance, and suction filtration was performed. The obtained residue was washed with water and ethyl acetate, and dissolved in heated toluene, followed by filtration through a filter aid filled with Celite, alumina, and Celite in this order. The obtained solution was concentrated and dried, and then recrystallized with toluene to give 1.11 g of a target white solid in a yield of 53%. This synthesis scheme is shown in the following formula (b-5).

[Chemical Formula 26]

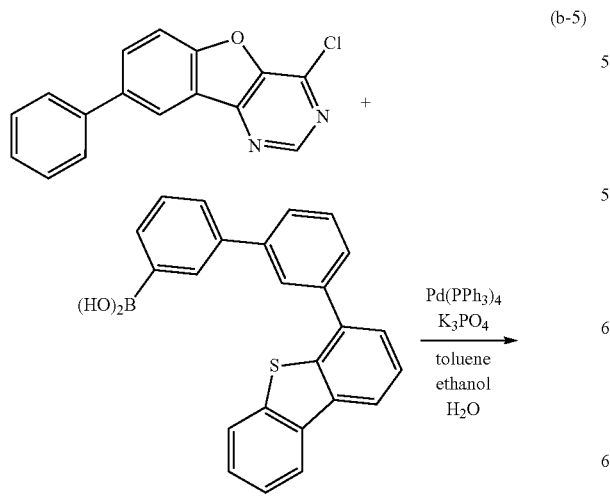

8Ph-4mDBtPBfpm
(101)

By a train sublimation method, 1.10 g of this white solid was sublimated and purified. The conditions of the sublimation purification were such that the solid was heated under a pressure of 2.8 Pa at 295° C. while the argon gas was made to flow at a flow rate of 10 mL/min. After the purification by sublimation, a target substance was obtained (0.90 g of a light yellow solid, collection rate: 82%).

Figure 10:
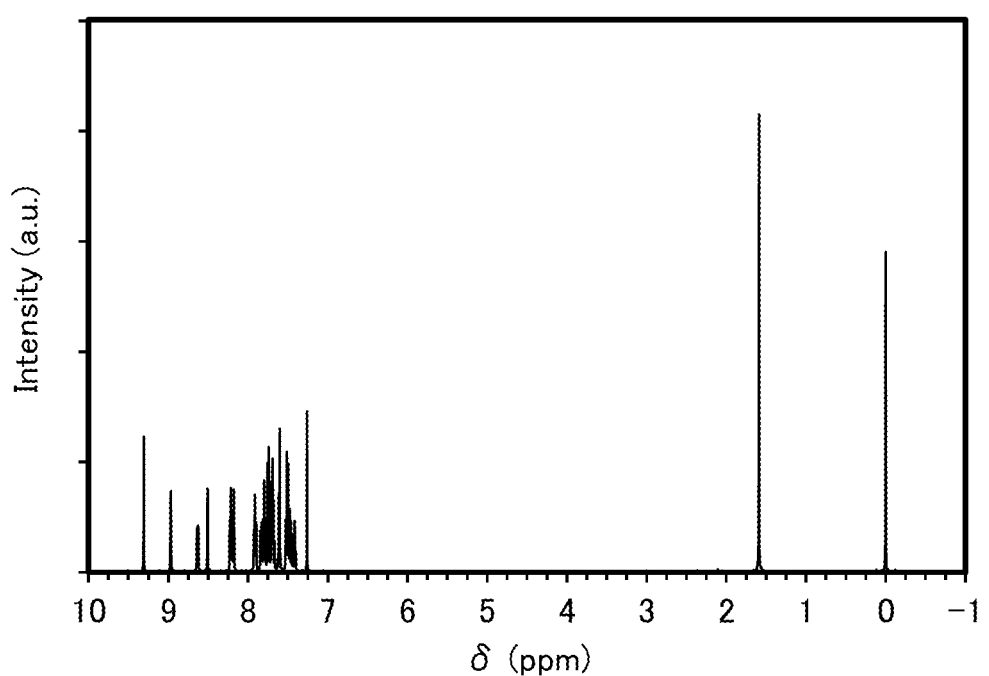
FIG. 10 is a $^1$H-NMR chart of an organic compound represented by Structural Formula (101).

Analysis results by nuclear magnetic resonance (H-NMR) spectroscopy of the white solid obtained in the above-described reaction are shown below. FIG. 10 shows a $^1$H-NMR chart. The results reveal that 8Ph-4mDBtBPBfpm, the above-described organic compound of one embodiment of the present invention represented by Structural Formula (101), was obtained in this example.

$^1$H-NMR. δ (CDCl$_3$): 7.42 (t, 1H), 7.45-7.53 (m, 4H), 7.60-7.61 (m, 2H), 7.67-7.76 (m, 5H), 7.80 (t, 2H), 7.84 (d, 1H), 7.91 (t, 2H), 8.18-8.23 (m, 3H), 8.51 (s, 1H), 8.63 (d, 1H), 8.97 (s, 1H), 9.31 (s, 1H).

<<Physical Properties of 8 pH-4mDBtBPBfpm>>

Next, the ultraviolet-visible absorption spectra (hereinafter, simply referred to as "absorption spectra") and emission spectra of a toluene solution and a solid thin film of 8Ph-4mDBtBPBfpm were measured.

Figure 11A:
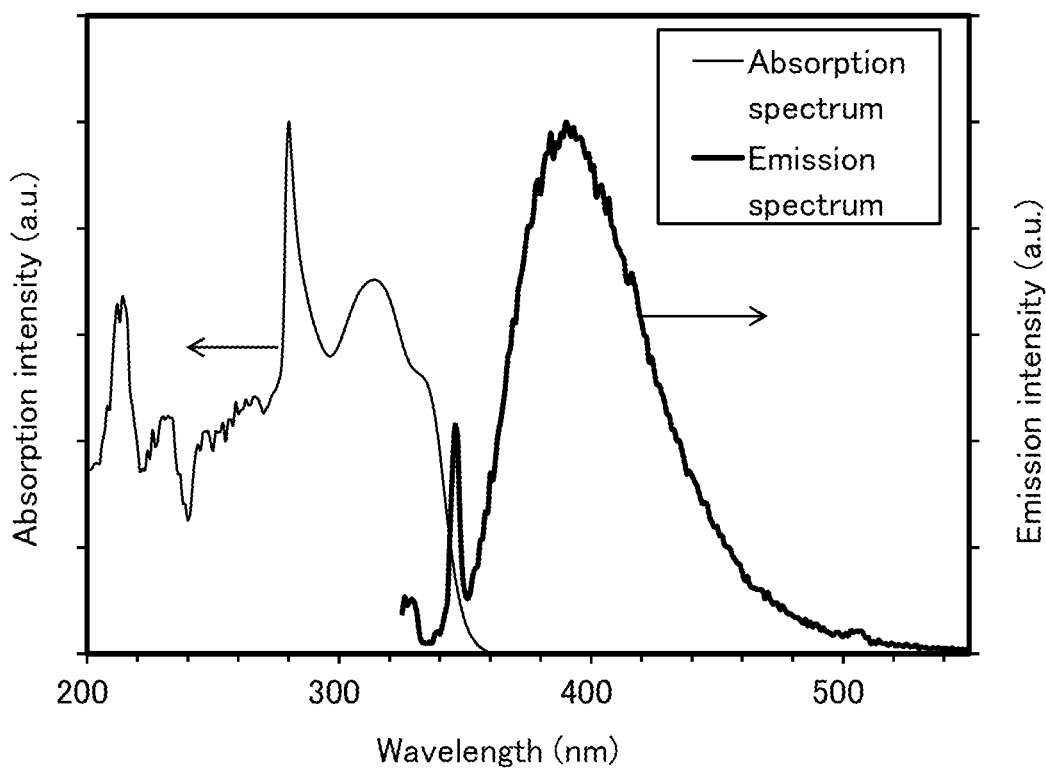
FIGS. 11A and 11B are ultraviolet-visible absorption spectra and emission spectra of the organic compound represented by Structural Formula (101).

The absorption spectrum in the toluene solution was measured with an ultraviolet-visible spectrophotometer (V550, produced by JASCO Corporation). The emission spectrum in the toluene solution was measured with a fluorescence spectrophotometer (FS920, manufactured by Hamamatsu Photonics K.K.). FIG. 11(A) shows the obtained measurement results of the absorption spectrum and the emission spectrum of the toluene solution. The horizontal axis represents wavelength and the vertical axes represent absorption intensity and emission intensity.

As can be seen in FIG. 11(A), 8Ph-4mDBtBPBfpm in the toluene solution exhibited absorption peaks at approximately 332 nm, 314 nm, and 280 nm and an emission wavelength peak at 390 nm (excitation wavelength: 314 nm).

Figure 11B:
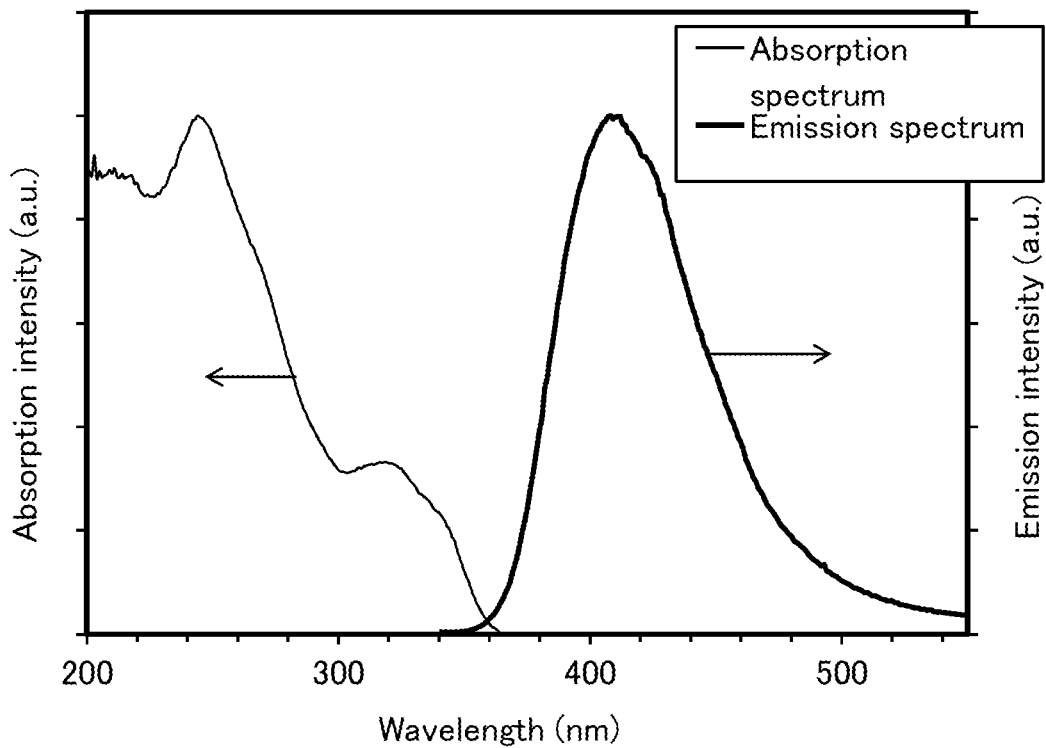

In the measurement of the absorption spectrum of the solid thin film, the solid thin film formed on a quartz substrate by a vacuum evaporation method was used and measurement was performed with an ultraviolet-visible spectrophotometer (U-4100, manufactured by Hitachi High-Technologies Corporation). In the measurement of the emission spectrum of the solid thin film, the solid thin film similar to the above was used and measurement was performed with a fluorescence spectrophotometer (FS920, manufactured by Hamamatsu Photonics K.K.). FIG. 11(B) shows the obtained measurement results of the absorption spectrum and emission spectrum of the solid thin film. The horizontal axis represents wavelength and the vertical axes represent absorption intensity and emission intensity.

As can be seen in FIG. 11(B), 8Ph-4mDBtBPBfpm of the solid thin film exhibited absorption peaks at approximately 340 nm, 320 nm, and 244 nm and an emission wavelength peak at 408 nm (excitation wavelength: 330 nm).

The organic compound of one embodiment of the present invention, 8Ph-4mDBtBPBfpm, has a high T1 level and thus is a host material suitable for a phosphorescent material (guest material) which emits light in the vicinity of blue to yellow regions. Note that 8Ph-4mDBtBPBfpm, the organic compound of one embodiment of the present invention, can also be used as a host material for a substance that emits phosphorescence in the visible region or a light-emitting substance.

Example 3

Synthesis Example 3

In this example, a synthesis method of 4-[3'-(dibenzothiophen-4-yl)biphenyl-3-yl]-2,8-diphenyl[1]benzofuro[3,2-d]pyrimidine (abbreviation: 2,8Ph-4mDBtBPBfpm), which is an organic compound of one embodiment of the present invention represented by Structural Formula (102) in Embodiment 1, will be described. Note that the structure of 2,8Ph-4mDBtBPBfpm is shown below.

[Chemical Formula 27]

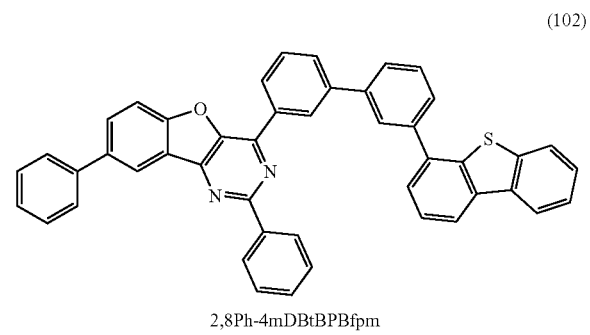

(102)

2,8Ph-4mDBtBPBfpm

Step 1: Synthesis of 2,8-dichloro-4-[3'-(dibenzothiophen-4-yl)biphenyl-3-yl]-[1]benzofuro[3,2-d]pyrimidine Into a three-neck flask, 1.22 g of 2,4,8-trichloro[1]benzofuro[3,2-d]pyrimidine, 1.67 g of 3'-(dibenzothiophen-4-yl)-1,1'-biphenyl-3-ylboronic acid, 1.02 g of potassium carbonate, 13.7 mL of toluene, 4.6 mL of ethanol, and 3.7 mL of water were put, they were degassed by being stirred under reduced pressure, and the air was replaced with nitrogen.

To this mixture, 78.0 mg of bis(triphenylphosphine)palladium(II) dichloride (abbreviation: Pd(PPh$_3$)$_2$Cl$_2$) was added, followed by stirring at 100° C. for 6.5 hours. Water was added to this reaction substance, suction filtration was performed, and the resulting residue was washed with water, ethanol, and toluene.

This residue was dissolved in heated toluene, followed by filtration through a filter aid filled with Celite, alumina, and Celite in this order. The obtained solution was concentrated and dried, and then recrystallized with toluene to give 2.06 g of a target white solid in a yield of 98%. This synthesis scheme is shown in the following formula (c-1).

[Chemical Formula 28]

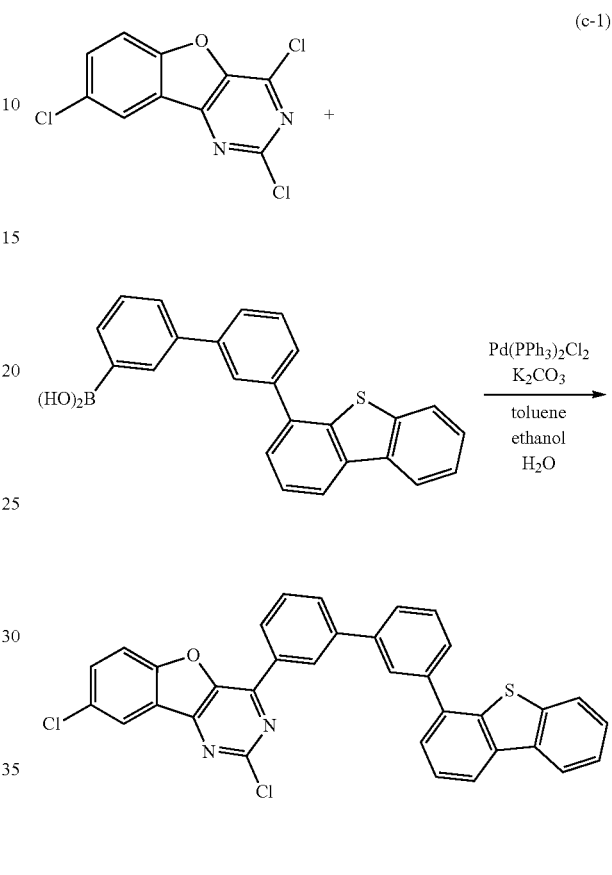

(c-1)

Step 2: Synthesis of 4-[3'-(dibenzothiophen-4-yl)biphenyl-3-yl]-2,8-diphenyl[1]benzofuro[3,2-d]pyrimidine Next, 2.06 g of 2,8-dichloro-4-[3'-(dibenzothiophen-4-yl)biphenyl-3-yl]-[1]benzofuro[3,2-d]pyrimidine, which is the target substance obtained in Step 1, 0.968 g of a phenylboronic acid, 1.09 g of cesium fluoride, and 36 mL of mesitylene were put into a three-neck flask, they were degassed by being stirred under reduced pressure, and the air was replaced with nitrogen.

This mixture was heated to 60° C., and 100 mg of tris(dibenzylideneacetone)dipalladium(0) and 78.3 mg of 2'-(dicyclohexylphosphino)acetophenone ethylene ketal were added thereto, followed by stirring at 100° C. for 18 hours. Water was added to this reaction liquid, suction filtration was performed, and the resulting residue was washed with water, ethanol, and toluene. This residue was dissolved in heated toluene, followed by filtration through a filter aid filled with Celite, alumina, and Celite in this order.

The obtained solution was concentrated and recrystallized with toluene, and the resulting solid was washed with a mixed solution of hexane and methanol. The obtained solid was purified by recycling preparative HPLC to give 0.760 g of a target light yellow solid in a yield of 7.2%. This synthesis scheme is shown in the following formula (c-2).

[Chemical Formula 29]

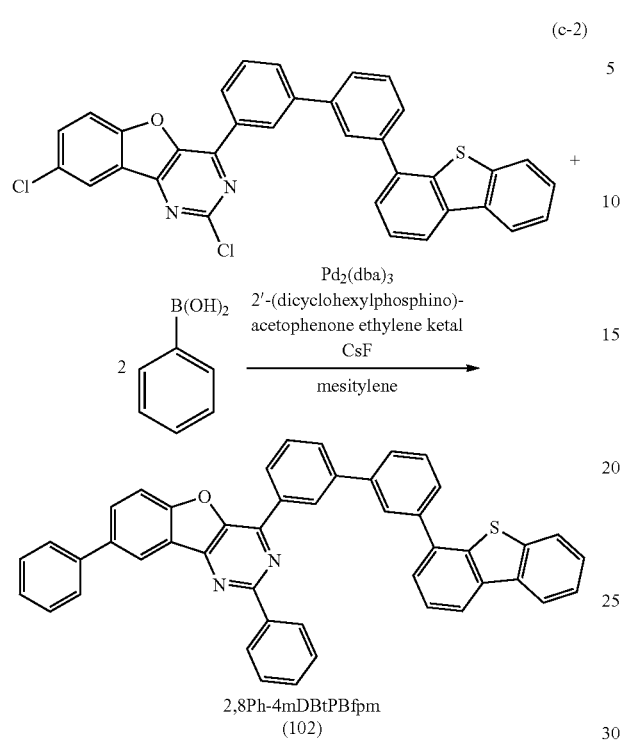

2,8Ph-4mDBtPBfpm
(102)

Figure 12:
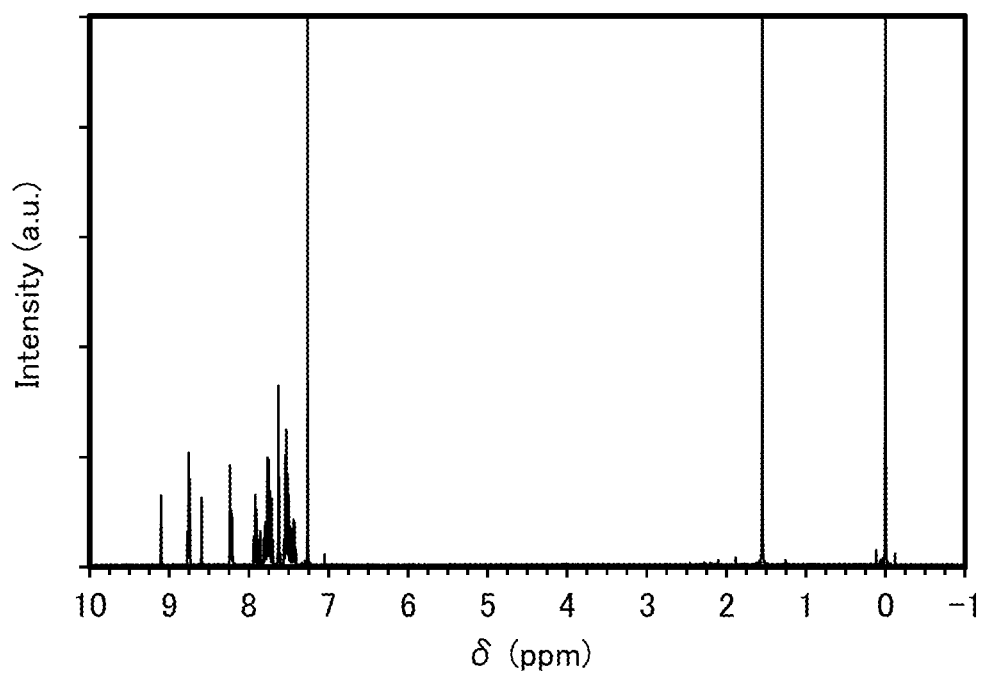
FIG. 12 is a $^1$H-NMR chart of an organic compound represented by Structural Formula (102).

Analysis results by nuclear magnetic resonance (¹H-NMR) spectroscopy of the light yellow solid obtained in the above-described reaction are shown below. FIG. 12 shows a ¹H-NMR chart. The results reveal that 2,8Ph-4mDBtBPBfpm, the above-described organic compound of one embodiment of the present invention represented by Structural Formula (102), was obtained in this example.

¹H-NMR. δ (CDCl$_3$): 7.41-7.56 (m, 8H), 7.60-7.64 (m, 2H), 7.71 (t, 1H), 7.73-7.81 (m, 6H), 7.86 (d, 1H), 7.90-7.94 (m, 2H), 8.20-8.24 (m, 3H), 8.59 (s, 1H), 8.74-8.77 (m, 3H), 9.10 (s, 1H).

The organic compound of one embodiment of the present invention, 2,8Ph-4mDBtBPBfpm, has a high T1 level and thus is a host material suitable for a phosphorescent material (guest material) which emits light in the vicinity of blue to yellow regions. Note that 2,8Ph-4mDBtBPBfpm, the organic compound of one embodiment of the present invention, can also be used as a host material for a substance that emits phosphorescence in the visible region or a light-emitting substance.

Example 4

Synthesis Example 4

In this example, a synthesis method of 2,4-bis(dibenzofuran-4-yl)-8-phenyl-[1]benzofuro[3,2-d]pyrimidine (abbreviation: 8Ph-2,4DBf2Bfpm), which is an organic compound of one embodiment of the present invention represented by Structural Formula (200) in Embodiment 1, will be described. Note that the structure of 8Ph-2,4DBf2Bfpm is shown below.

[Chemical Formula 30]

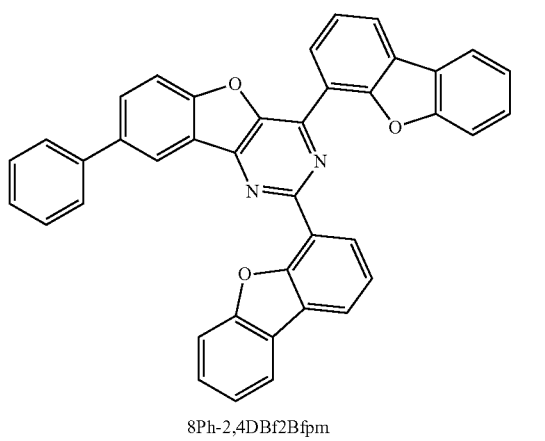

8Ph-2,4DBf2Bfpm

Step 1: Synthesis of 2,4-bis(dibenzofuran-4-yl)-8-chloro-[1]benzofuro[3,2-d]pyrimidine Into a three-neck flask, 1.56 g of 2,4,8-trichloro[1]benzofuro[3,2-d]pyrimidine, 2.42 g of dibenzofuran-4-boronic acid, 1.58 g of potassium carbonate, 22 mL of toluene, 7 mL of ethanol, and 5.7 mL of water were put, they were degassed by being stirred under reduced pressure, and the air in the flask was replaced with nitrogen.

To this mixture, bis(triphenylphosphine)palladium(II) dichloride (abbreviation: Pd(PPh$_3$)$_2$Cl$_2$) was added, followed by stirring at 100° C. for 7 hours. Water was added to this reaction liquid, suction filtration was performed, and the resulting residue was washed with water, ethanol, and toluene. This residue was dissolved in heated toluene, followed by filtration through a filter aid filled with Celite, alumina, and Celite in this order.

The obtained solution was concentrated and dried to give 2.84 g of a target white solid in a yield of 93%. This synthesis scheme is shown in the following formula (d-1).

[Chemical Formula 31]

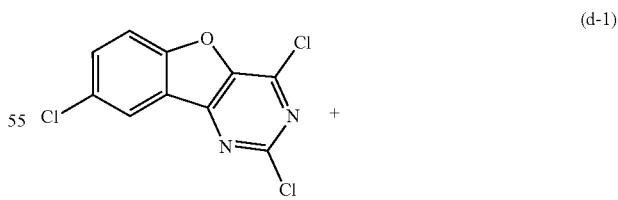

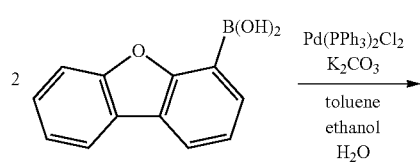

-continued

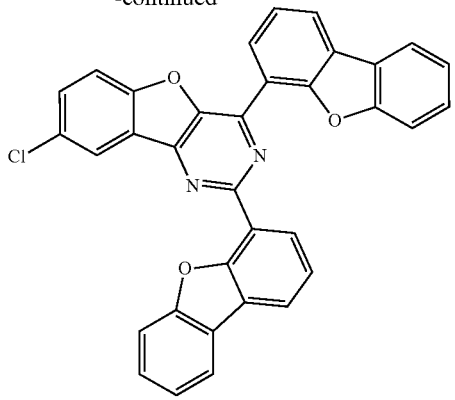

[Chemical Formula 32]

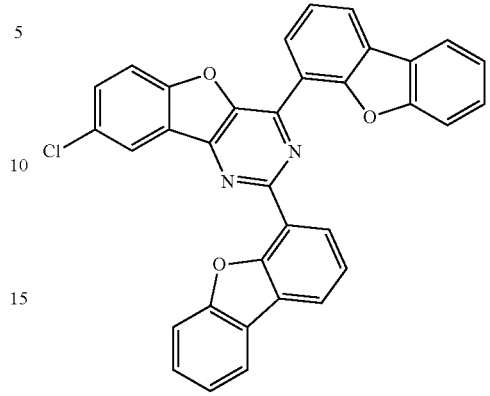

(d-2)

Step 2: Synthesis of 2,4-bis(dibenzofuran-4-yl)-8-phenyl-[1]benzofuro[3,2-d]pyrimidine Next, 2.84 g of 2,4-bis(dibenzofuran-4-yl)-8-chloro-[1]benzofuro[3,2-d]pyrimidine, which is the target substance in Step 1, 0.78 g of a phenylboronic acid, 1.62 g of cesium fluoride, and 53 mL of mesitylene were put into a three-neck flask, they were degassed by being stirred under reduced pressure, and the air in the flask was replaced with nitrogen.

This mixture was heated to 60° C., and 0.147 g of tris(dibenzylideneacetone)dipalladium(0) and 0.115 g of 2'-(dicyclohexylphosphino)acetophenone ethylene ketal were added thereto, followed by stirring at 100° C. for 12.5 hours and then at 120° C. for 26 hours. Furthermore, 0.145 g of tris(dibenzylideneacetone)dipalladium(0) and 0.115 g of 2'-(dicyclohexylphosphino)acetophenone ethylene ketal were added to this mixture, followed by stirring at 120° C. for 23.5 hours.

Water was added to this reaction liquid, suction filtration was performed, and the resulting residue was washed with water, ethanol, and toluene. This residue was dissolved in heated toluene, followed by filtration through a filter aid filled with Celite, alumina, and Celite in this order. The obtained solution was concentrated and dried, and then recrystallized with toluene to give 1.94 g of a target white solid in a yield of 63%.

By a train sublimation method, 1.93 g of this white solid was sublimated and purified. The conditions of the sublimation purification were such that the solid was heated under a pressure of 2.51 Pa at 300° C. while the argon gas was made to flow at a flow rate of 11 mL/min. After the purification by sublimation, 1.73 g of a target light yellow solid was obtained at a collection rate of 90%. This synthesis scheme is shown in the following formula (d-2).

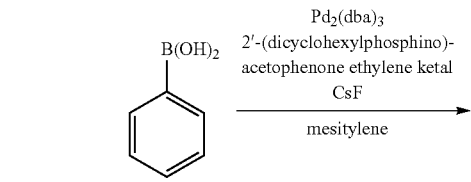

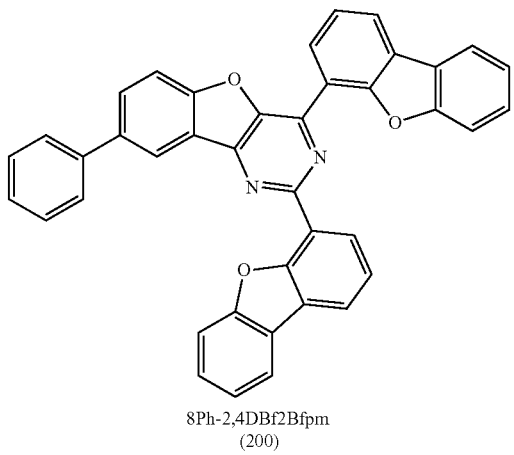

8Ph-2,4DBf2Bfpm
(200)

Figure 13:
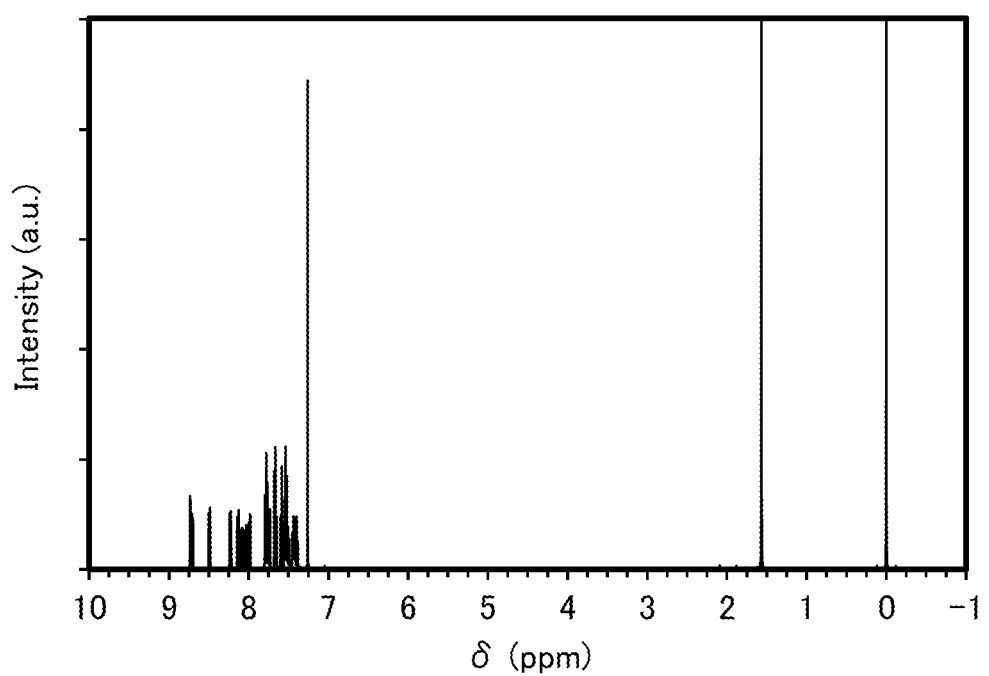
FIG. 13 is a $^1$H-NMR chart of an organic compound represented by Structural Formula (200).

Analysis results by nuclear magnetic resonance ($^1$H-NMR) spectroscopy of the light yellow solid obtained in the above-described reaction are shown below. FIG. 13 shows a $^1$H-NMR chart. The results reveal that 8Ph-2,4DBf2Bfpm, the above-described organic compound of one embodiment of the present invention represented by Structural Formula (200), was obtained in this example.

$^1$H-NMR. δ (CDCl$_3$): 7.38-7.45 (m, 3H), 7.49-7.55 (m, 4H), 7.58 (t, 1H), 7.66 (t, 2H), 7.74 (d, 1H), 7.76-7.80 (m, 3H), 7.99 (d, 1H), 8.04 (d, 1H), 8.08 (d, 1H), 8.13 (d, 1H), 8.23 (d, 1H), 8.49 (d, 1H), 8.71 (d, 1H), 8.73 (s, 1H).

The organic compound of one embodiment of the present invention, 8Ph-2,4DBf2Bfpm, has a high T1 level and thus is a host material suitable for a phosphorescent material (guest material) which emits light in the vicinity of blue to yellow regions. Note that 8Ph-2,4DBf2Bfpm, the organic compound of one embodiment of the present invention, can also be used as a host material for a substance that emits phosphorescence in the visible region or a light-emitting substance.

Example 5

Figure 14:
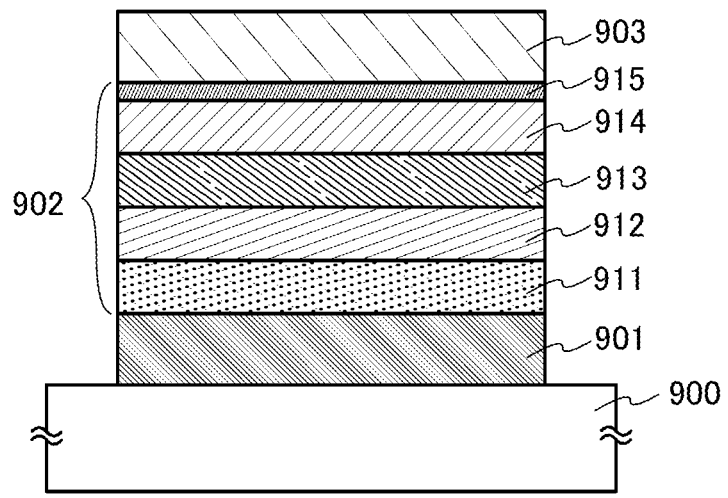
FIG. 14 is a drawing illustrating a light-emitting element.

In this example, the element structures, manufacturing methods, and characteristics of a light-emitting element 1, which is the light-emitting element of one embodiment of the present invention and uses 4-[3-(dibenzothiophen-4-yl)phenyl]-8-phenyl-[1]benzofuro[3,2-d]pyrimidine (abbreviation: 8Ph-4mDBtPBfpm) (Structural Formula (100)) described in Example 1 in its light-emitting layer, a comparative light-emitting element 2 which uses 4,8-bis[3-(dibenzothiophen-4-yl)phenyl]benzofuro[3,2-d]pyrimidine in its light-emitting layer, and a comparative light-emitting element 3 which uses 8-(dibenzothiophen-4-yl)-4-[3'-(dibenzothiophen-4-yl)biphenyl-3-yl]-[1]benzofuro[3,2-d]pyrimidine (abbreviation: 8DBt-4mDBtPBfpm) in its light-emitting layer will be described. Note that FIG. 14 illustrates the element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (70 nm) | DBT3P-II:MoOx (2:1 50 nm) | PCBBiF BP (20 nm) | * | 8Ph-4mDBtPBfpm (20 nm) | NBphen (15 nm) | LiF (1 nm) | Al (200 nm) |
| Comparative light-emitting element 2 | ITSO (70 nm) | DBT3P-II:MoOx (2:1 50 nm) | PCBBiF BP (20 nm) | ** | 4,8mDBtP2Bfpm (20 nm) | NBphen (15 nm) | LiF (1 nm) | Al (200 nm) |
| Comparative light-emitting element 3 | ITSO (70 nm) | DBT3P-II:MoOx (2:1 50 nm) | PCBBiF BP (20 nm) | *** | 8DBt-4mDBtPBfpm (20 nm) | NBphen (15 nm) | LiF (1 nm) | Al (200 nm) |

* 8Ph-4mDBtPBfpm:PCCP:[Ir(ppy)2(4dppy)] (0.6:0.4:0.1 40 nm)
** 4,8mDBtP2Bfpm:PCCP:[Ir(ppy)2(4dppy)] (0.6:0.4:0.1 40 nm)
*** 8DBt-4mDBtPBfpm:PCCP:[Ir(ppy)2(4dppy)] (0.6:0.4:0.1 40 nm)

[Chemical Formula 33]

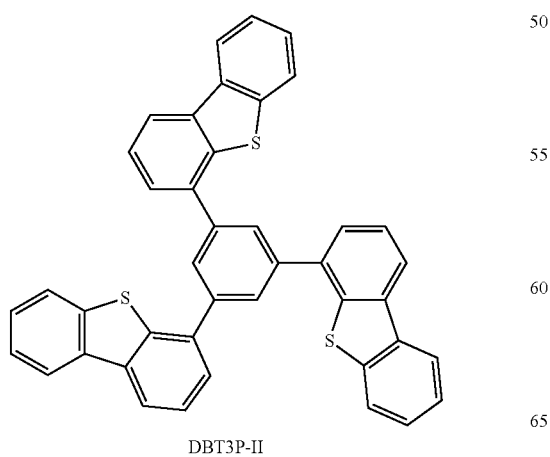

DBT3P-II

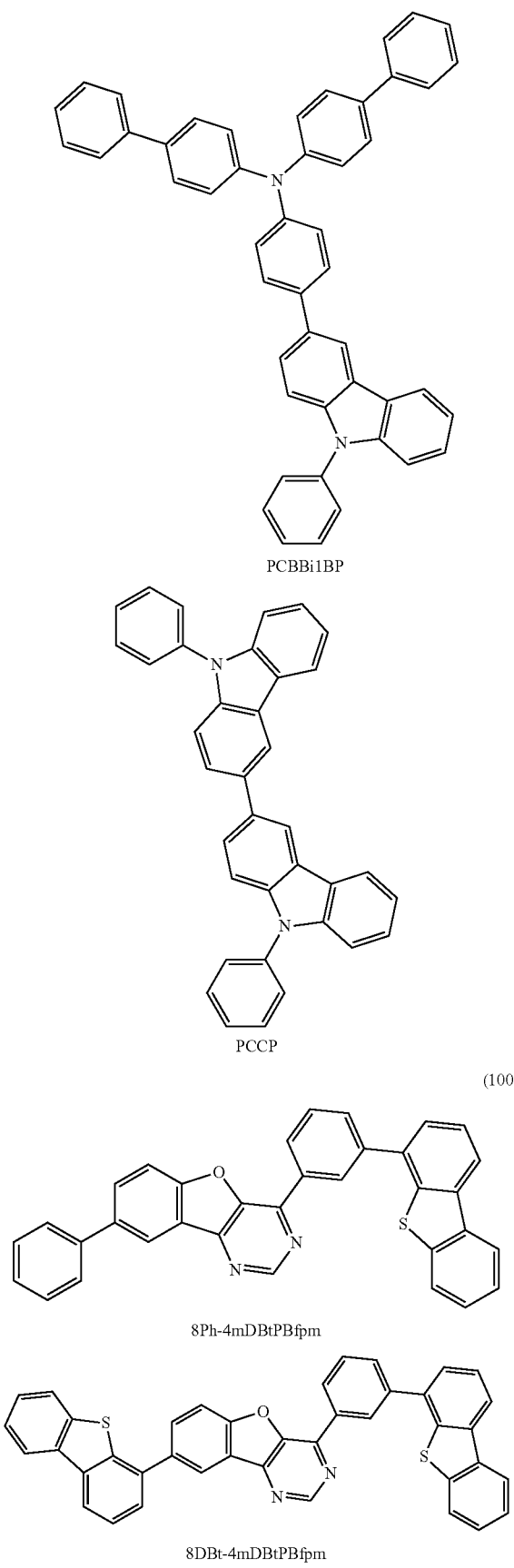

PCBBi1BP

PCCP

8Ph-4mDBtPBfpm

8DBt-4mDBtPBfpm

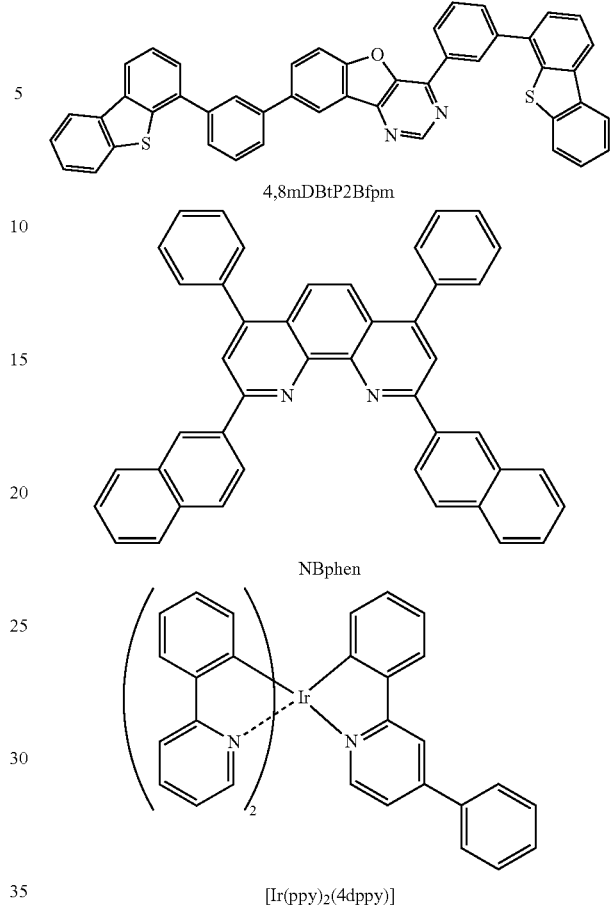

4,8mDBtP2Bfpm

NBphen

[Ir(ppy)$_2$(4dppy)]

<<Fabrication of Light-Emitting Elements>>

The light-emitting elements described in this example have a structure as illustrated in FIG. 14, in which a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus in which the pressure was reduced to about 10$^{-4}$ Pa, vacuum baking at 170° C. for 30 minutes was performed in a heating chamber in the vacuum evaporation apparatus, and then the substrate was naturally cooled down for about 30 minutes.

Next, the hole-injection layer 911 was formed over the first electrode 901. For the formation of the hole-injection layer 911, the pressure in the vacuum evaporation apparatus was reduced to 10$^{-4}$ Pa, and then 1,3,5-tri(dibenzothiophen-4-yl)benzene (abbreviation: DBT3P-II) and molybdenum oxide were co-evaporated such that DBT3P-II:molybdenum oxide was equal to 2:1 (mass ratio) and the thickness was 50 nm.

Then, the hole-transport layer 912 was formed over the hole-injection layer 911. The hole-transport layer 912 was formed to a thickness of 20 nm by evaporation using 4,4'-diphenyl-4''-(9-phenyl-9H-carbazol-3-yl)triphenylamine (abbreviation: PCBBi1BP).

Next, the light-emitting layer 913 was formed over the hole-transport layer 912.

For the light-emitting layer 913 in the light-emitting element 1, co-evaporation using bis[2-(2-pyridinyl-κN)phenyl-κC][2-(4-phenyl-2-pyridinyl-κN)phenyl-κC]iridium (III) (abbreviation: [Ir(ppy)$_2$(4dppy)]) as a guest material (phosphorescent material) in addition to 8Ph-4mDBtPBfpm and 3,3'-bis(9-phenyl-9H-carbazole) (abbreviation: PCCP) was performed such that the weight ratio was 8Ph-4mDBtPBfpm:PCCP:[Ir(ppy)$_2$(4dppy)]=0.6:0.4:0.1. The thickness was set to 40 nm. For the comparative light-emitting element 2, co-evaporation using [Ir(ppy)$_2$(4dppy)] as a guest material (phosphorescent material) in addition to 4,8mDBtP2Bfpm and PCCP was performed such that the weight ratio was 4,8mDBtP2Bfpm:PCCP:[Ir(ppy)$_2$(4dppy)]=0.6:0.4:0.1. The thickness was set to 40 nm. For the comparative light-emitting element 3, co-evaporation using [Ir(ppy)$_2$(4dppy)] as a guest material (phosphorescent material) in addition to 8DBt-4mDBtPBfpm and PCCP was performed such that the weight ratio was 8DBt-4mDBtPBfpm:PCCP:[Ir(ppy)$_2$(4dppy)]=0.6:0.4:0.1. The thickness was set to 40 nm.

Next, the electron-transport layer 914 was formed over the light-emitting layer 913.

The electron-transport layer 914 in the light-emitting element 1 was formed in the following manner: 8Ph-4mDBtPBfpm and 2,9-bis(naphthalen-2-yl)-4,7-diphenyl-1,10-phenanthroline (abbreviation: NBphen) were sequentially deposited by evaporation to thicknesses of 20 nm and 15 nm, respectively. The electron-transport layer 914 in the comparative light-emitting element 2 was formed in the following manner: 4,8mDBtP2Bfpm and NBphen were sequentially deposited by evaporation to thicknesses of 20 nm and 15 nm, respectively. The electron-transport layer 914 in the comparative light-emitting element 3 was formed in the following manner: 8DBt-4mDBtPBfpm and NBphen were sequentially deposited by evaporation to thicknesses of 20 nm and 15 nm, respectively.

Then, the electron-injection layer 915 was formed over the electron-transport layer 914. The electron-injection layer 915 was formed to a thickness of 1 nm by evaporation using lithium fluoride (LiF).

After that, the second electrode 903 was formed over the electron-injection layer 915. The second electrode 903 was formed using aluminum to a thickness of 200 nm by an evaporation method. In this example, the second electrode 903 functions as a cathode.

Through the above steps, the light-emitting elements in each of which an EL layer 902 was provided between a pair of electrodes over the substrate 900 were fabricated. The hole-injection layer 911, the hole-transport layer 912, the light-emitting layer 913, the electron-transport layer 914, and the electron-injection layer 915 described in the above steps were functional layers forming the EL layer in one embodiment of the present invention. Furthermore, in all the evaporation steps in the above fabrication method, an evaporation method by a resistance-heating method was used.

The light-emitting elements fabricated as described above were sealed using another substrate (not illustrated). At the time of the sealing using the another substrate (not illustrated), the another substrate (not illustrated) on which a sealant that solidifies by ultraviolet light was applied was fixed onto the substrate 900 in a glove box containing a nitrogen atmosphere, and the substrates were bonded to each other such that the sealant attached to the periphery of the light-emitting element formed over the substrate 900. At the time of the sealing, the sealant was irradiated with 365-nm ultraviolet light at 6 J/cm$^2$ to be solidified, and the sealant was subjected to heat treatment at 80° C. for 1 hour to be stabilized.

<<Operation Characteristics of Light-Emitting Elements>>

Figure 15:
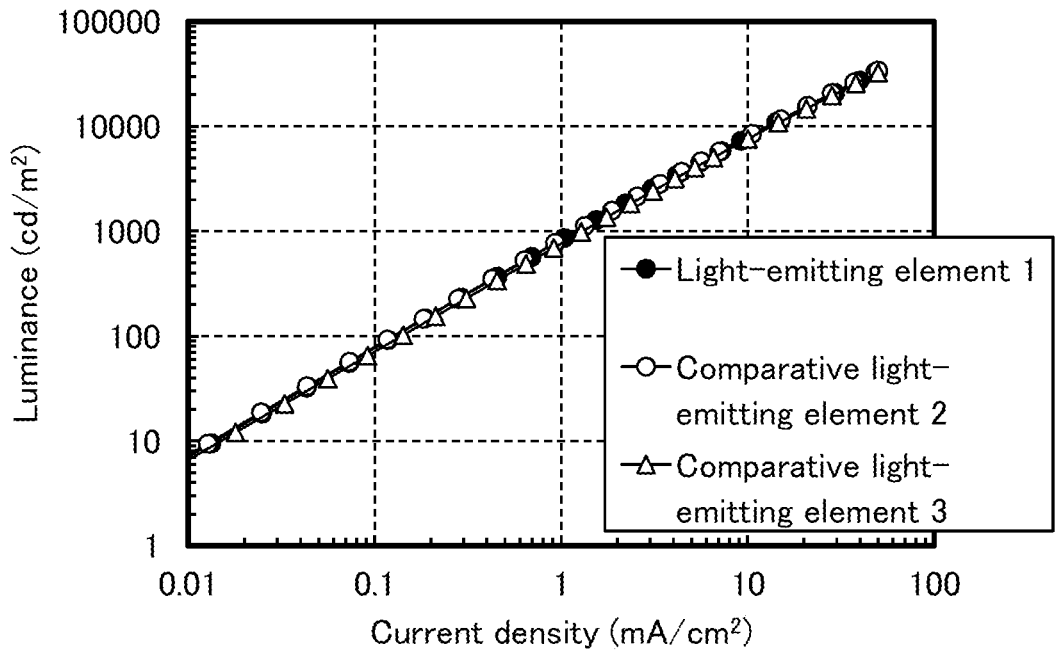
FIG. 15 is a graph showing current density-luminance characteristics of a light-emitting element 1, a comparative light-emitting element 2, and a comparative light-emitting element 3.
Figure 16:
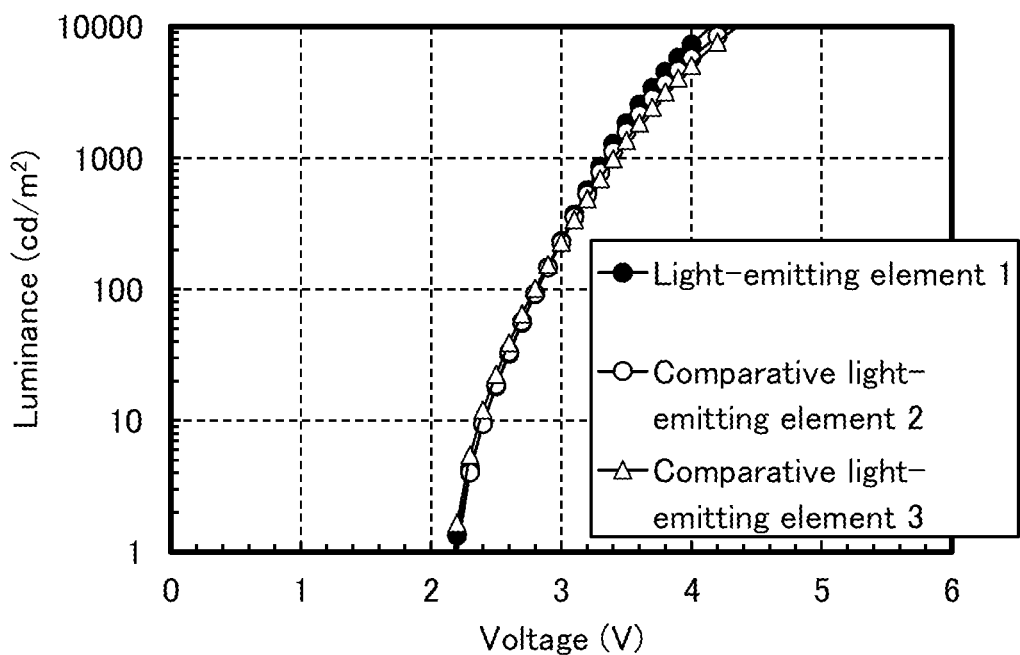
FIG. 16 is a graph showing voltage-luminance characteristics of the light-emitting element 1, the comparative light-emitting element 2, and the comparative light-emitting element 3.
Figure 17:
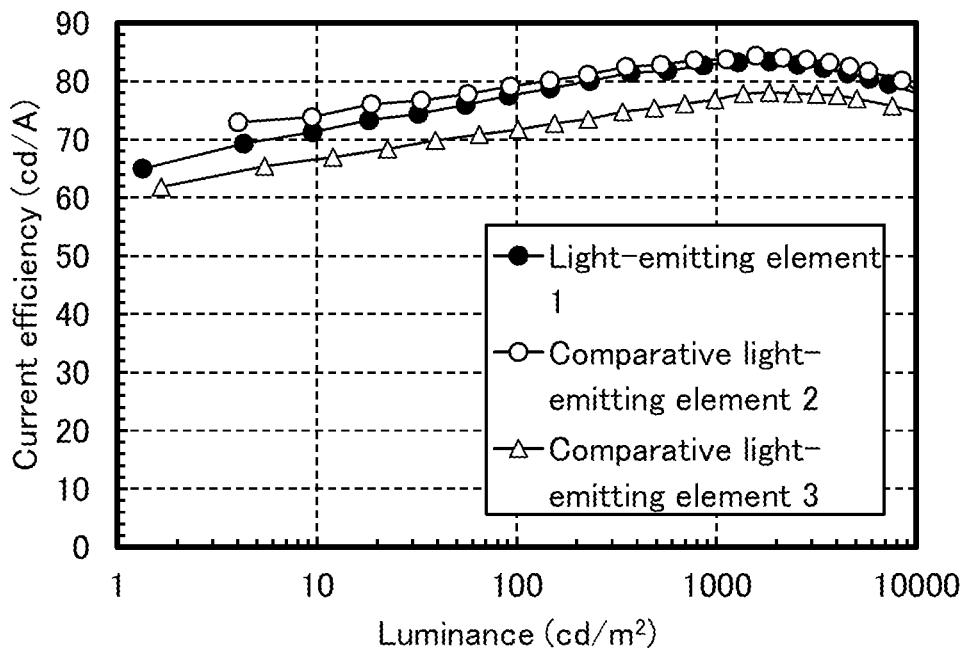
FIG. 17 is a graph showing luminance-current efficiency characteristics of the light-emitting element 1, the comparative light-emitting element 2, and the comparative light-emitting element 3.
Figure 18:
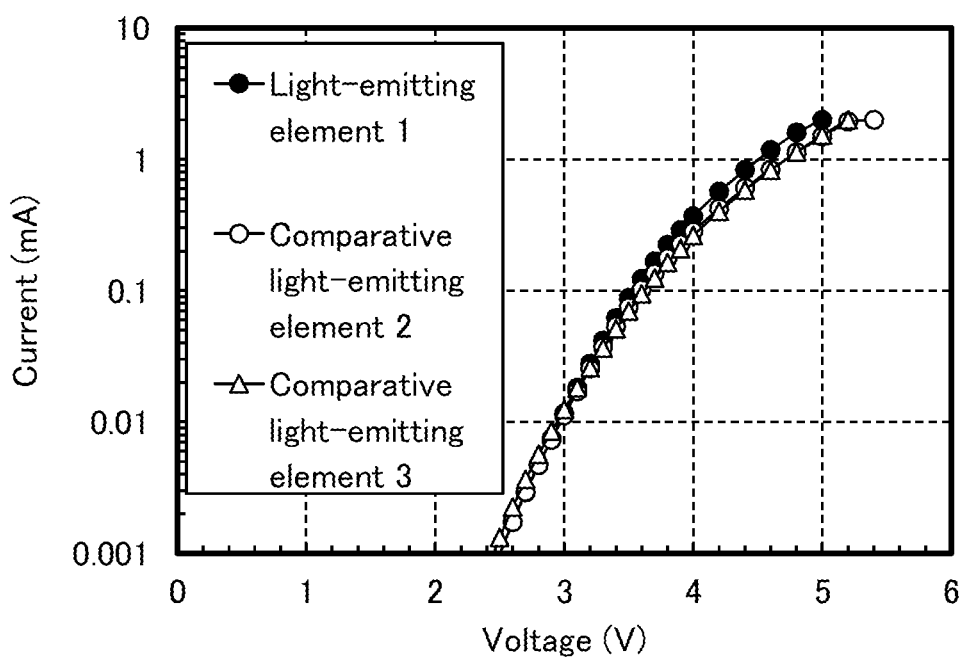
FIG. 18 is a graph showing voltage-current characteristics of the light-emitting element 1, the comparative light-emitting element 2, and the comparative light-emitting element 3.

Operation characteristics of each of the fabricated light-emitting elements were measured. Note that the measurement was carried out at room temperature (an atmosphere maintained at 25° C.). As the results of the operation characteristics of the light-emitting elements, the current density-luminance characteristics are shown in FIG. 15, the voltage-luminance characteristics are shown in FIG. 16, the luminance-current efficiency characteristics are shown in FIG. 17, and the voltage-current characteristics are shown in FIG. 18.

Table 2 below shows initial values of main characteristics of each of the light-emitting elements at around 1000 cd/m$^2$.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.3 | 0.041 | 1.0 | (0.45, 0.54) | 900 | 83 | 79 | 24 |
| Comparative light-emitting element 2 | 3.4 | 0.054 | 1.3 | (0.44, 0.55) | 1100 | 84 | 77 | 25 |
| Comparative light-emitting element 3 | 3.4 | 0.051 | 1.3 | (0.44, 0.55) | 980 | 77 | 71 | 22 |

Figure 19:
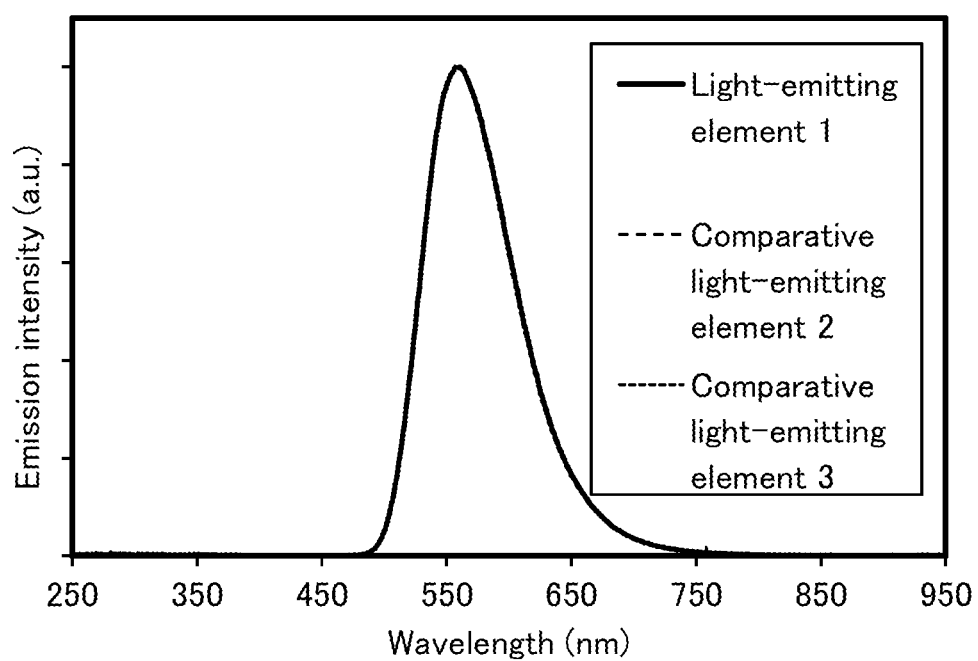
FIG. 19 is a graph showing emission spectra of the light-emitting element 1, the comparative light-emitting element 2, and the comparative light-emitting element 3.

FIG. 19 shows emission spectra of the case where current at a current density of 2.5 mA/cm$^2$ was supplied to the light-emitting element 1, the comparative light-emitting element 2, and the comparative light-emitting element 3. As shown in FIG. 19, the emission spectra of the light-emitting element 1, the comparative light-emitting element 2, and the comparative light-emitting element 3 have peaks at around 558 nm, and it is suggested that each peak is derived from light emission of [Ir(ppy)$_2$(4dppy)] contained in the light-emitting layer 913.

Figure 20:
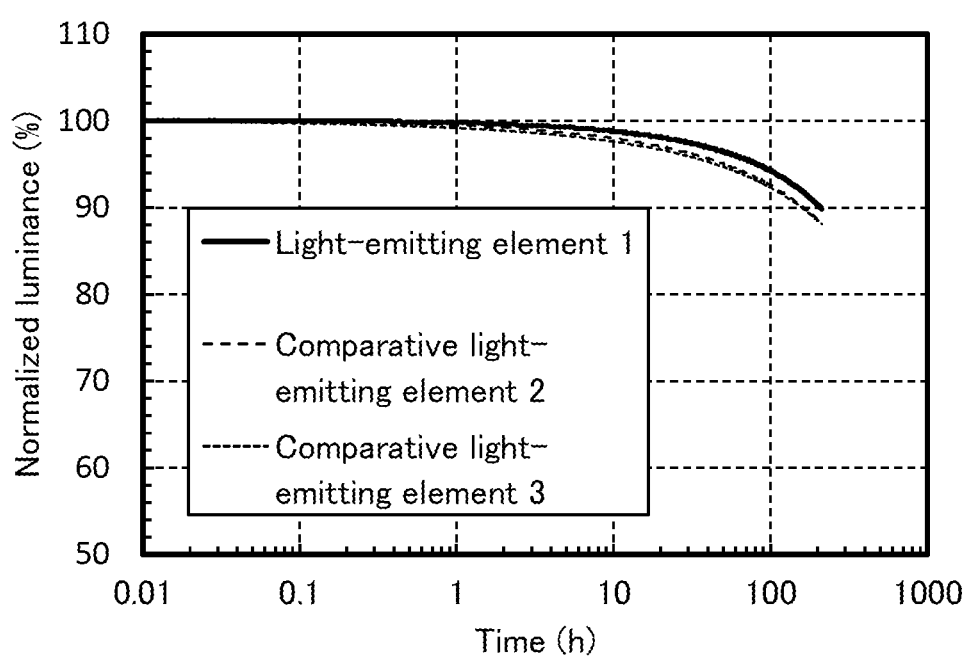
FIG. 20 is a graph showing reliability of the light-emitting element 1, the comparative light-emitting element 2, and the comparative light-emitting element 3.
Figure 21:
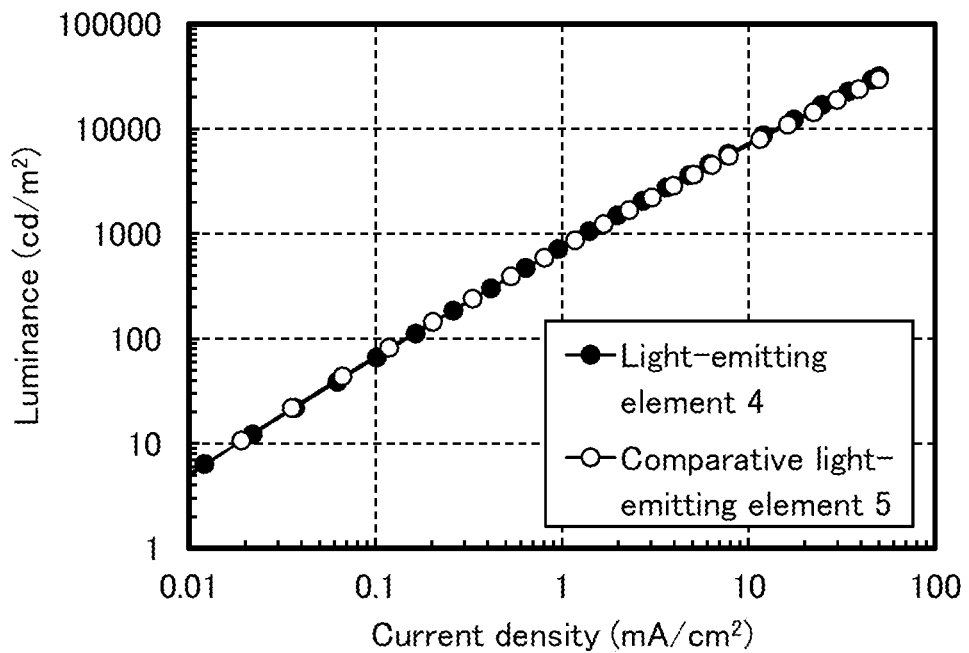
FIG. 21 is a graph showing current density-luminance characteristics of a light-emitting element 4 and a comparative light-emitting element 5.
Figure 22:
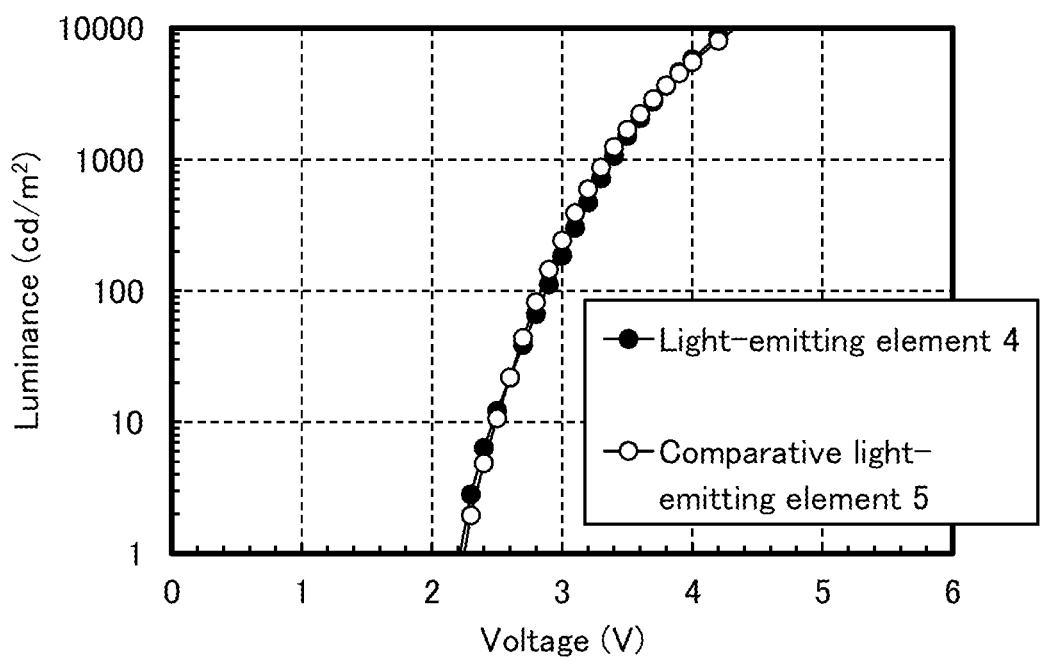
FIG. 22 is a graph showing voltage luminance characteristics of the light-emitting element 4 and the comparative light-emitting element 5.
Figure 23:
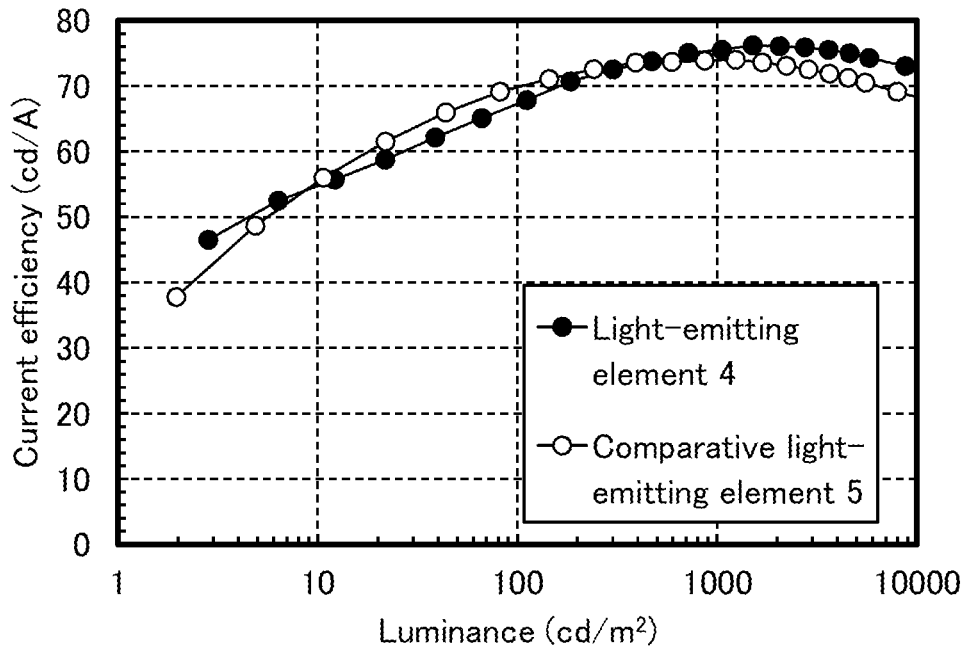
FIG. 23 is a graph showing luminance-current efficiency characteristics of the light-emitting element 4 and the comparative light-emitting element 5.
Figure 24:
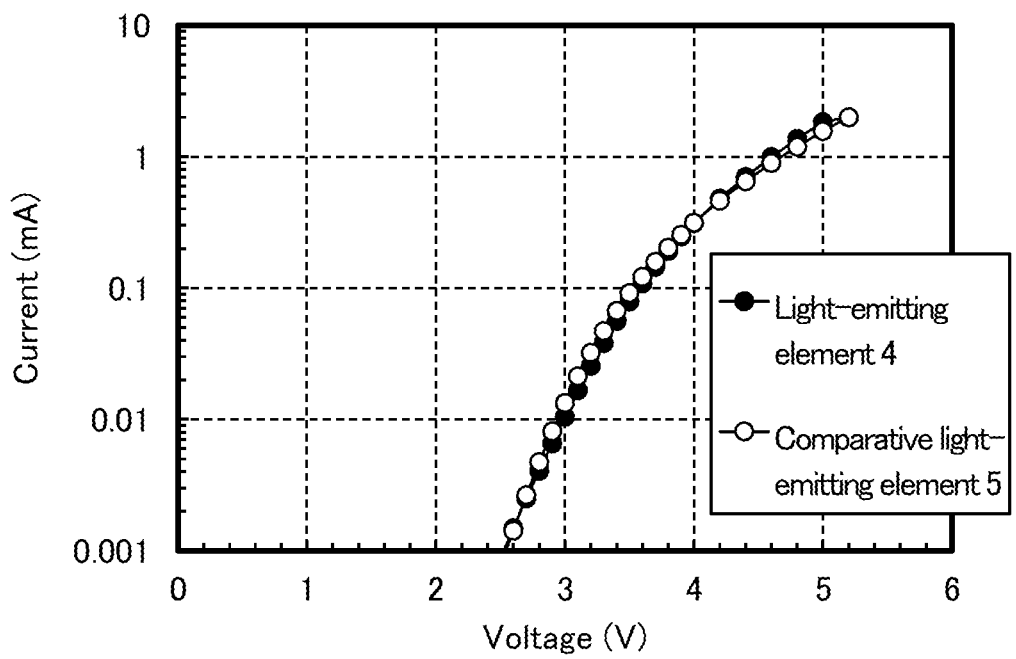
FIG. 24 is a graph showing voltage-current characteristics of the light-emitting element 4 and the comparative light-emitting element 5.

Next, reliability tests were performed on the light-emitting element 1, the comparative light-emitting element 2, and the comparative light-emitting element 3. FIG. 20 shows the results of the reliability tests. In FIG. 20, the vertical axis represents normalized luminance (%) with an initial luminance of 100%, and the horizontal axis represents driving time (h) of the elements. As the reliability tests, constant current driving tests where a constant current was supplied at a current density of 50 mA/cm$^2$ were performed.

The results of the reliability tests revealed that the light-emitting element 1 suffered less degradation in the initial stage of driving because the time taken until the luminance is reduced by 5% from the initial luminance (LT95) of the light-emitting element 1 was 83 hours and those of the comparative light-emitting element 2 and the comparative light-emitting element 3 were 51 hours and 43 hours, respectively. It is useful to use the organic compound of one embodiment of the present invention, 8Ph-4mDBtPBfpm (Structural Formula (100)), in improving element characteristics of the light-emitting element. Note that 4,8mDBtP2Bfpm used in the comparative light-emitting element 2 has a structure in which dibenzothiophene is directly bonded to the 8-position of a benzofuropyrimidine skeleton via a phenyl group, and 8DBt-4mDBtPBfpm used in the comparative light-emitting element 3 has a structure in which dibenzothiophene is bonded to the 8-position of a benzofuropyrimidine skeleton, while 8Ph-4mDBtPBfpm used in the light-emitting element 1 has a molecular structure which includes a phenyl group at the 8-position of a benzofuropyrimidine skeleton. From the above facts, in order to suppress initial degradation, it is not that the substituent at the 8-position of a benzofuropyrimidine skeleton may be anything, but introducing an unsubstituted phenyl group is important.

Thus, when an organic compound having a structure including a phenyl group, which is not a bulky substituent, at the 8-position of a benzofuropyrimidine skeleton or a benzothienopyrimidine skeleton like the organic compound of one embodiment of the present invention is used in a light-emitting element, transfer of excitation energy between molecules becomes smooth, which brings about an effect on the suppression of initial degradation of the light-emitting element. Accordingly, a reliable light-emitting element can be provided.

Example 6

In this example, a light-emitting element 4, which is the light-emitting element of one embodiment of the present invention and uses 8Ph-4mDBtPBfpm (Structural Formula (100)) described in Example 1 in its light-emitting layer, and a comparative light-emitting element 5, which uses 4,8mDBtP2Bfpm in its light-emitting layer, were fabricated and the measured characteristics of the light-emitting elements are shown.

Note that the element structure of the light-emitting element 4 and the comparative light-emitting element 5 fabricated in this example is similar to that in FIG. 14 mentioned in Example 5, and the specific composition of each layer of the element structure is as shown in Table 3. Chemical formulae of materials used in this example are shown below.

TABLE 3

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 4 | ITSO (70 nm) | DBT3P-II:MoOx (2:1 45 nm) | PCBBiIBP (20 nm) | * | 8Ph-4mDBtPBfpm (20 nm) | NBphen (10 nm) | LIF (1 nm) | Al (200 nm) |
| Comparative light-emitting element 5 | ITSO (70 nm) | DBT3P-II:MoOx (2:1 45 nm) | PCBBiIBP (20 nm) | ** | 4,8mDBtP2Bfpm (20 nm) | NBphen (10 nm) | LIF (1 nm) | Al (200 nm) |

* 8Ph-4mDBtPBfpm:PCCP:[Ir(ppy)2(4dppy)] (0.6:0.4:0.1 40 nm)
** 4,8mDBtP2Bfpm:PCCP:[Ir(ppy)2(4dppy)] (0.6:0.4:0.1 40 nm)

[Chemical Formulae 34]

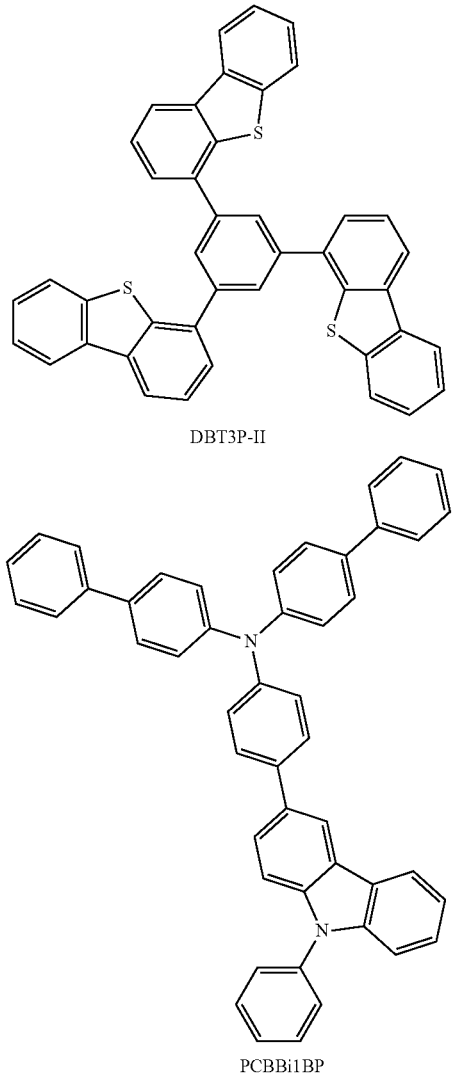

DBT3P-II

PCBBi1BP

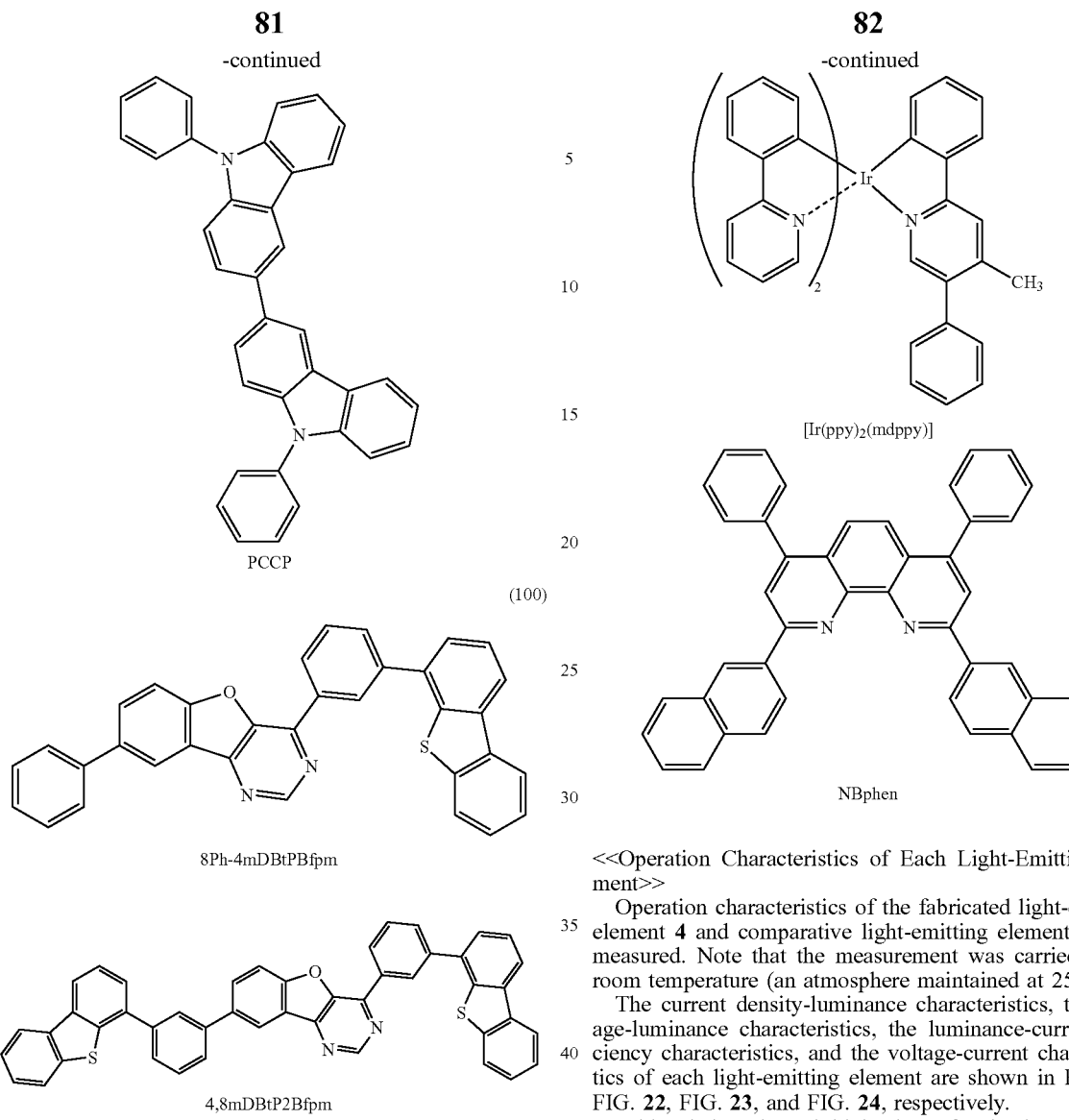

<<Operation Characteristics of Each Light-Emitting Element>>

Operation characteristics of the fabricated light-emitting element 4 and comparative light-emitting element 5 were measured. Note that the measurement was carried out at room temperature (an atmosphere maintained at 25° C.).

The current density-luminance characteristics, the voltage-luminance characteristics, the luminance-current efficiency characteristics, and the voltage-current characteristics of each light-emitting element are shown in FIG. 21, FIG. 22, FIG. 23, and FIG. 24, respectively.

Table 4 below shows initial values of main characteristics of each of the light-emitting elements at around 1000 cd/m².

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 4 | 3.4 | 0.056 | 1.4 | (0.35, 0.62) | 1100 | 76 | 70 | 21 |
| Comparative light-emitting element 5 | 3.3 | 0.047 | 1.2 | (0.35, 0.62) | 870 | 74 | 70 | 20 |

Figure 25:
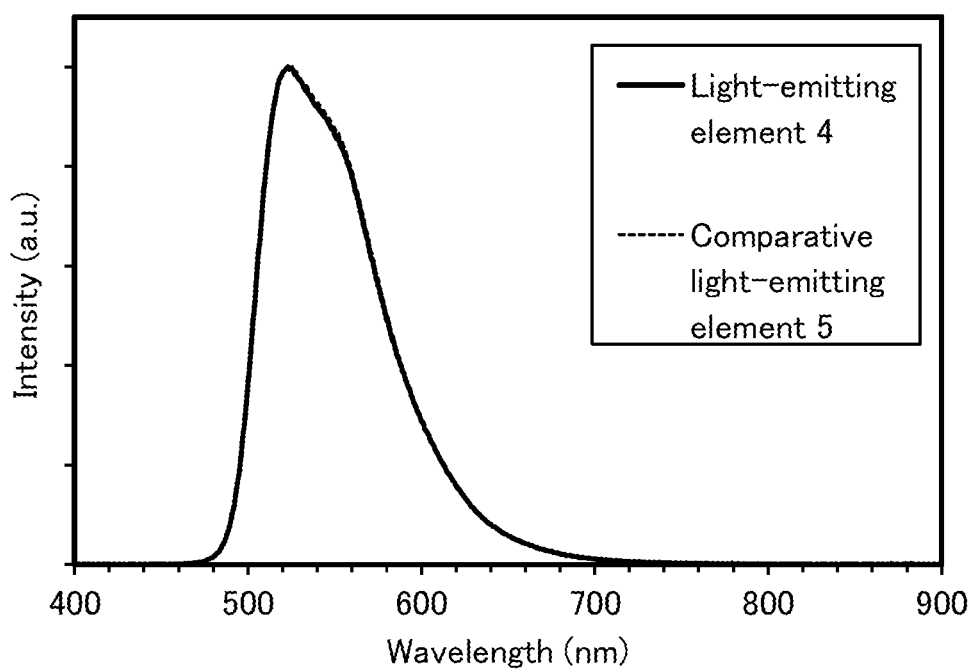
FIG. 25 is a graph showing emission spectra of the light-emitting element 4 and the comparative light-emitting element 5.

FIG. 25 shows emission spectra of the case where current at a current density of 2.5 mA/cm² was supplied to the light-emitting element 4 and the comparative light-emitting element 5. As shown in FIG. 25, the emission spectra of the light-emitting elements have peaks at around 525 nm, and it is suggested that the peaks are derived from light emission of [Ir(ppy)₂(mdppy)] contained in the light-emitting layer 913.

Figure 26:
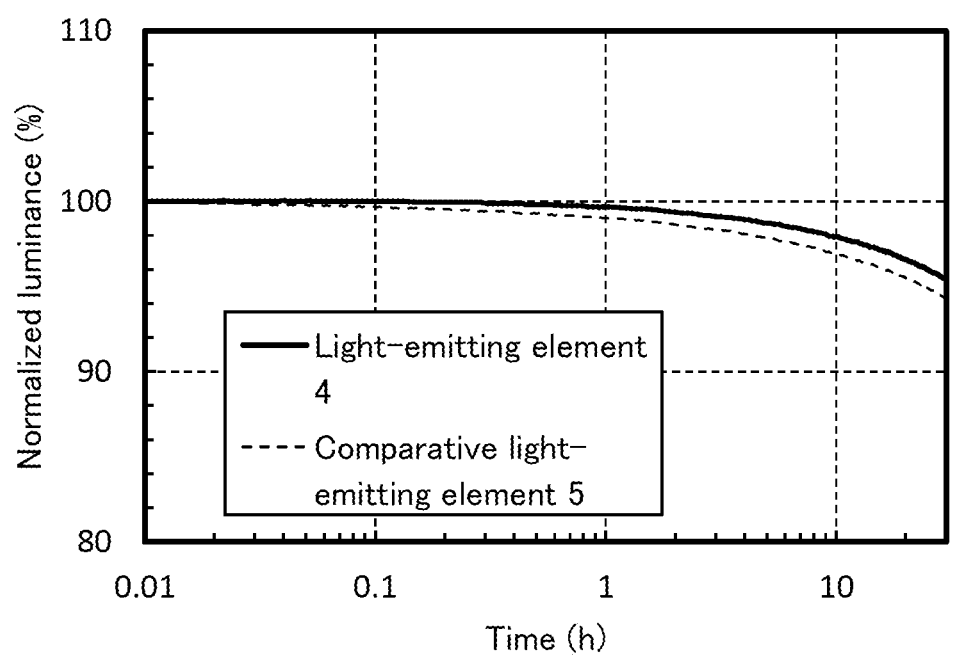
FIG. 26 is a graph showing reliability of the light-emitting element 4 and the comparative light-emitting element 5.
Figure 27:
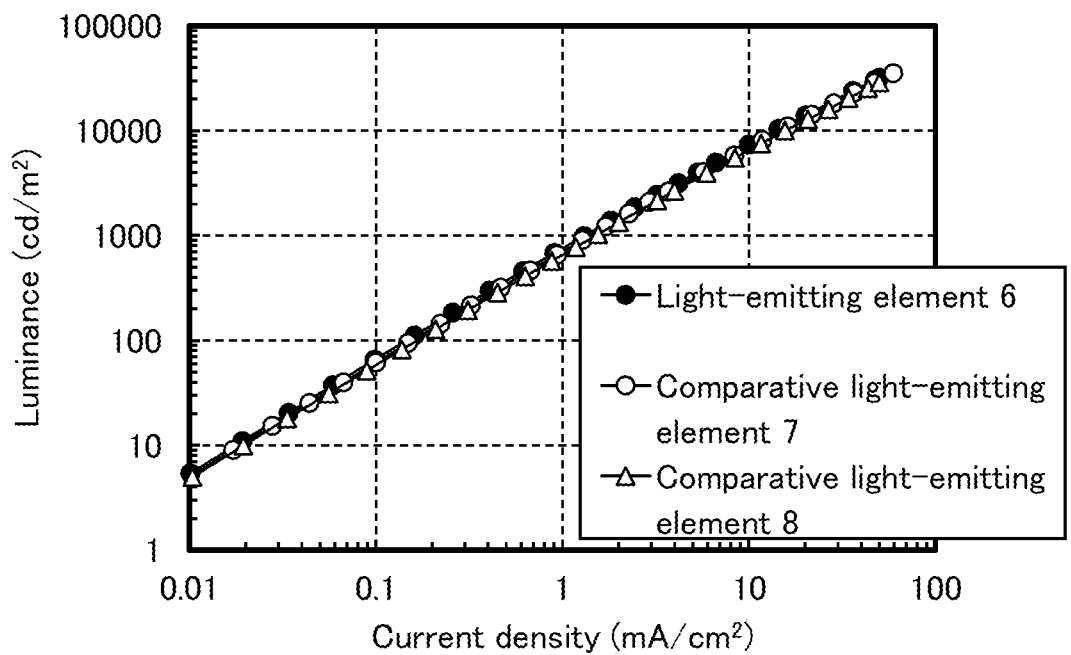
FIG. 27 is a graph showing current density-luminance characteristics of a light-emitting element 6, a comparative light-emitting element 7, and a comparative light-emitting element 8.
Figure 28:
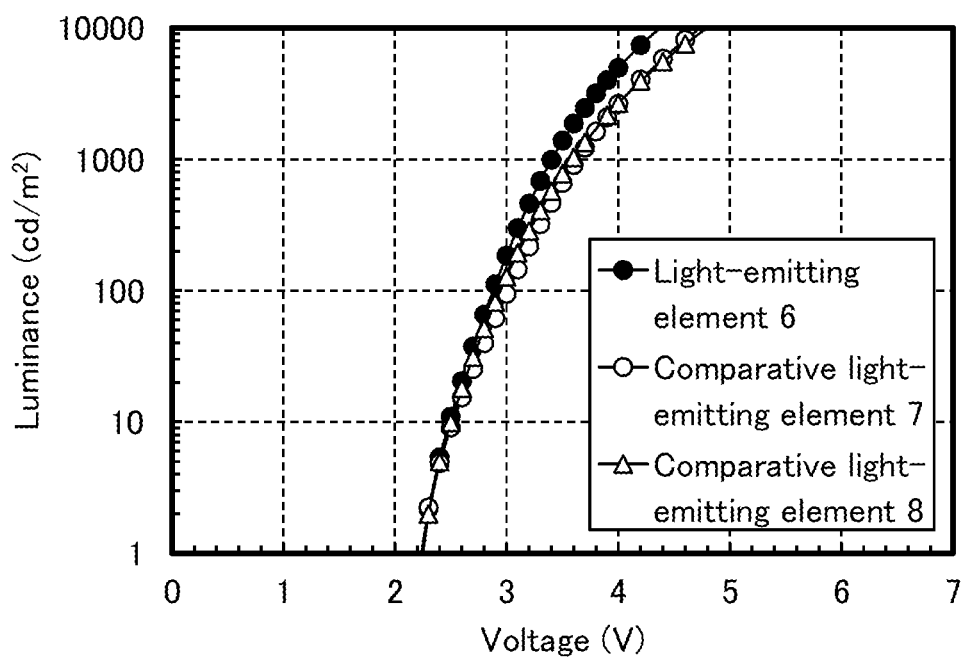
FIG. 28 is a graph showing voltage-luminance characteristics of the light-emitting element 6, the comparative light-emitting element 7, and the comparative light-emitting element 8.
Figure 29:
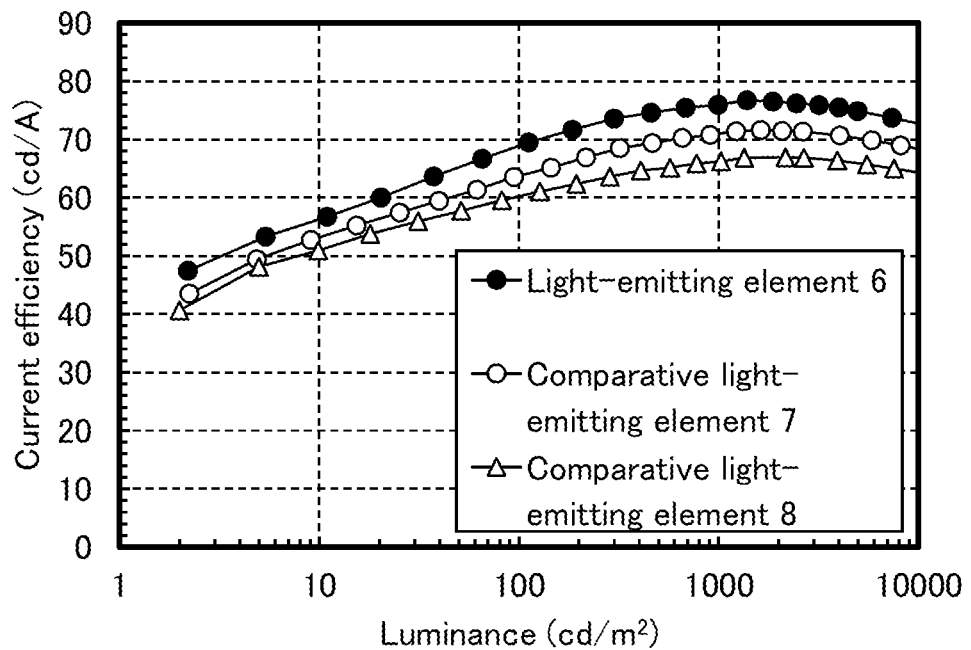
FIG. 29 is a graph showing luminance-current efficiency characteristics of the light-emitting element 6, the comparative light-emitting element 7, and the comparative light-emitting element 8.
Figure 30:
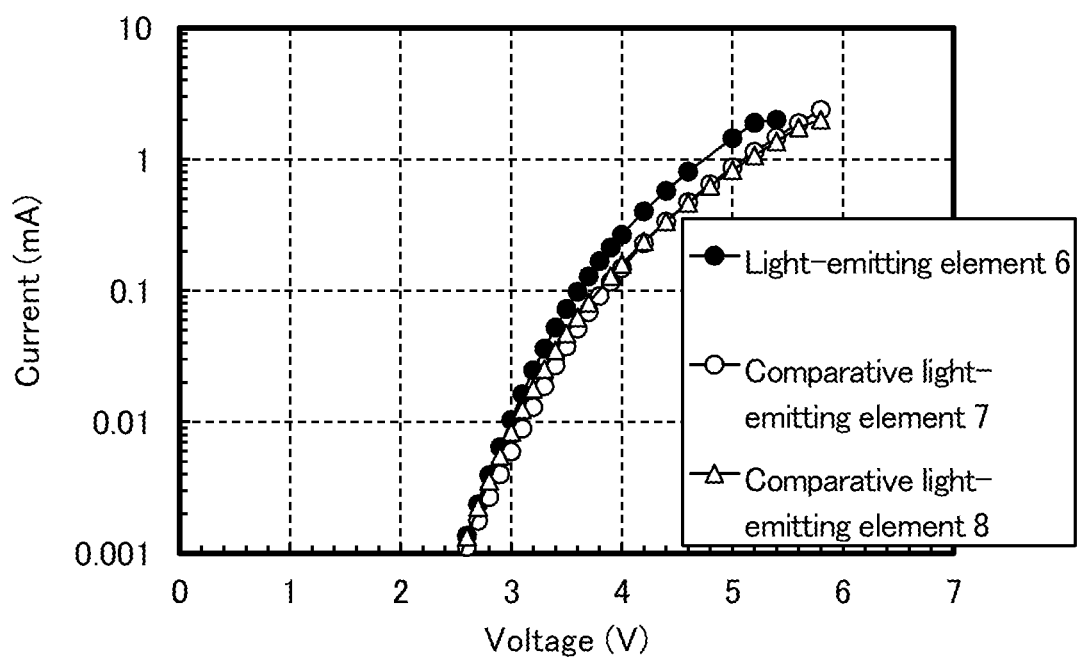
FIG. 30 is a graph showing voltage-current characteristics of the light-emitting element 6, the comparative light-emitting element 7, and the comparative light-emitting element 8.

Next, reliability tests were performed on the light-emitting element 4 and the comparative light-emitting element 5. FIG. 26 shows the results of the reliability tests. In FIG. 26, the vertical axis represents normalized luminance (%) with an initial luminance of 100%, and the horizontal axis represents driving time (h) of the elements. As the reliability tests, constant current driving tests where a constant current was supplied at a current density of 50 mA/cm² were performed.

The results of the reliability tests show that the light-emitting element 4 which used the organic compound of one embodiment of the present invention, 8Ph-4mDBtPBfpm, had a suppressed initial degradation because the time taken until the luminance is reduced by 5% from the initial luminance (LT95) of the light-emitting element 4 was 33 hours and that of the comparative light-emitting element 5 which used the comparative organic compound, 4,8mDBtP2Bfpm, was 24 hours. This is owing to the effect of the organic compound of one embodiment of the present invention, 8Ph-4mDBtPBfpm, having at least a phenyl group at the 8-position of a benzofuropyrimidine skeleton. From the above facts, in order to suppress initial degradation, introducing an unsubstituted phenyl group at the 8-position of a benzofuropyrimidine skeleton is important. Thus, it is useful to use the organic compound of one embodiment of the present invention in improving reliability of the light-emitting element.

Example 7

In this example, a light-emitting element 6, which is the light-emitting element of one embodiment of the present invention and uses 4-[3'-(dibenzothiophen-4-yl)biphenyl-3-yl]-8-phenyl-[1]benzofuro[3,2-d]pyrimidine (abbreviation: 8Ph-4mDBtBPBfpm) (Structural Formula (101)) described in Example 2 in its light-emitting layer, a comparative light-emitting element 7 which uses 8-(dibenzothiophen-4-yl)-4-[3'-(dibenzothiophen-4-yl)biphenyl-3-yl]-[1]benzofuro[3,2-d]pyrimidine (abbreviation: 8DBt-4mDBtBPBfpm) in its light-emitting layer, and a comparative light-emitting element 8, which uses 4-[3'-(dibenzothiophen-4-yl)biphenyl-3-yl]-8-[3-(dibenzothiophen-4-yl)phenyl]-[1]benzofuro[3,2-d]pyrimidine (abbreviation: 8mDBtP-4mDBtBPBfpm) in its light-emitting layer, were fabricated and the measured characteristics of the light-emitting elements are shown.

Note that the element structure of the light-emitting element 6, the comparative light-emitting element 7, and the comparative light-emitting element 8 fabricated in this example is similar to that in FIG. 14 mentioned in Example 5, and the specific composition of each layer of the element structure is as shown in Table 5. Chemical formulae of materials used in this example are shown below.

TABLE 5

| | First electrode | Hole-injection layer | Hole-transport layer | Light-emitting layer | Electron-transport layer | Electron-injection layer | Second electrode |
|---|---|---|---|---|---|---|---|
| Light-emitting element 6 | ITSO (70 nm) | DBT3P-II:MoOx (2:1 45 nm) | PCBBiIBP (20 nm) | * | 8Ph-4mDBtBPBfpm (20 nm) | NBphen (10 nm) | LiF (1 nm) | Al (200 nm) |
| Comparative light-emitting element 7 | ITSO (70 nm) | DBT3P-II:MoOx (2:1 45 nm) | PCBBiIBP (20 nm) | ** | 8DBt-4mDBtBPBfpm (20 nm) | NBphen (10 nm) | LiF (1 nm) | Al (200 nm) |
| Comparative light-emitting element 8 | ITSO (70 nm) | DBT3P-II:MoOx (2:1 45 nm) | PCBBiIBP (20 nm) | *** | 8mDBtP-4mDBtBPBfpm (20 nm) | NBphen (10 nm) | LiF (1 nm) | Al (200 nm) |

* 8Ph-4mDBtBPBfpm:PCCP:[Ir(ppy)2(mdppy)] (0.5:0.5:0.1 40 nm)

** 8DBt-4mDBtBPBfpm:PCCP:[Ir(ppy)2(mdppy)] (0.5:0.5:0.1 40 nm)

*** 8mDBtP-4mDBtBPBfpm:PCCP:[Ir(ppy)2(mdppy)] (0.5:0.5:0.1 40 nm)

[Chemical Formulae 35]
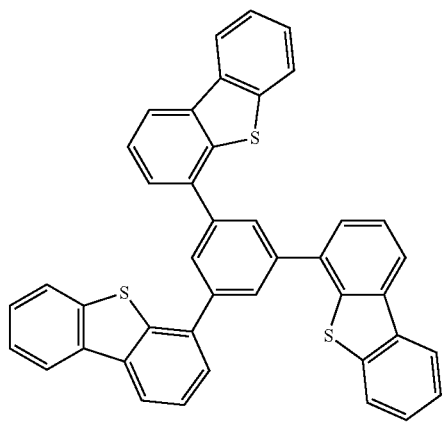
DBT3P-II
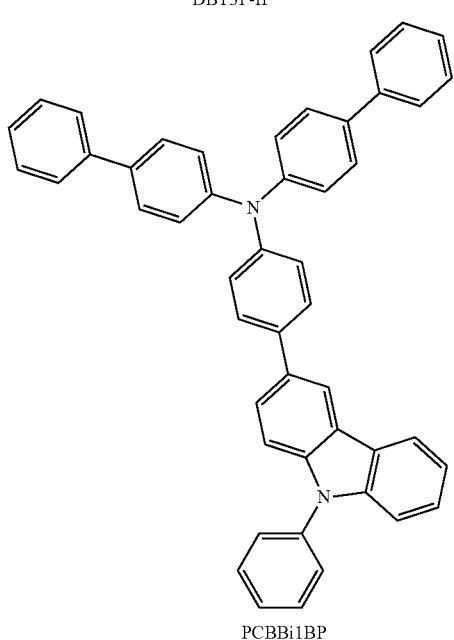
PCBBi1BP
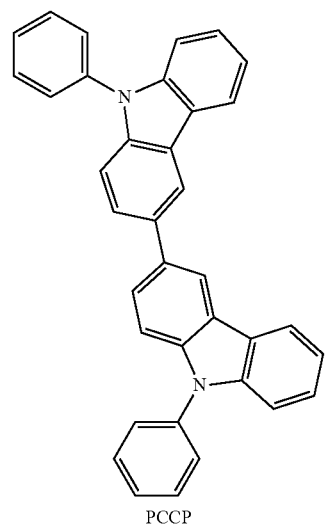
PCCP
(101)
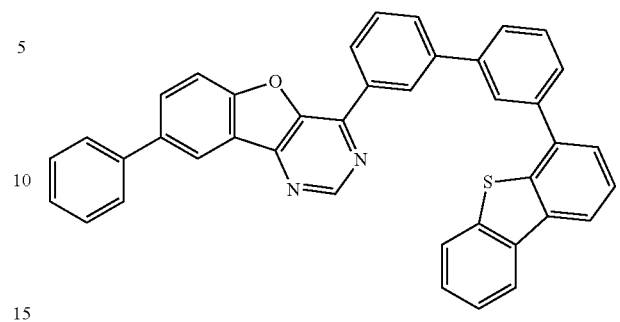
8Ph-4mDBtBPBfpm
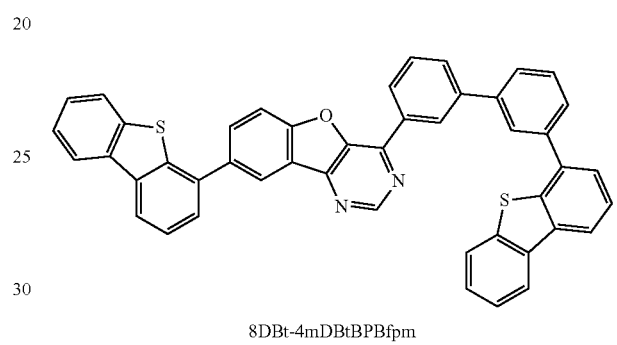
8DBt-4mDBtBPBfpm
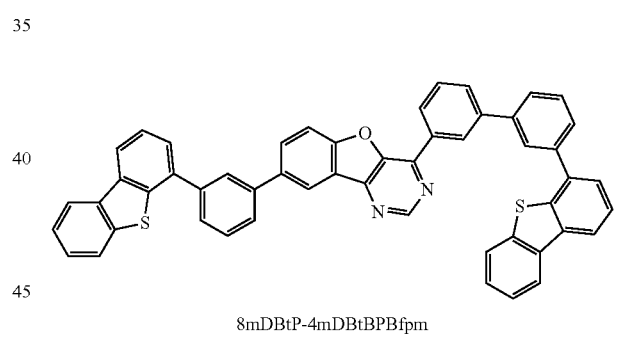
8mDBtP-4mDBtBPBfpm
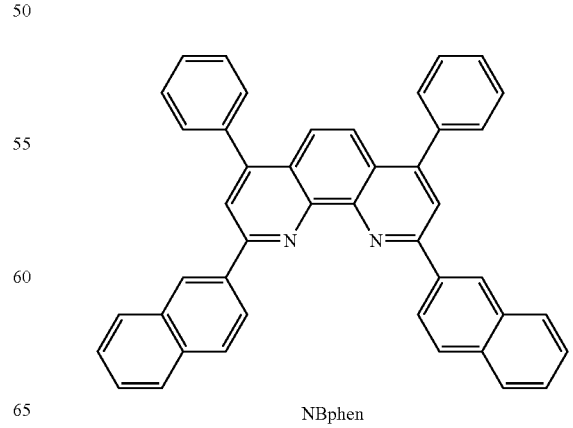
NBphen

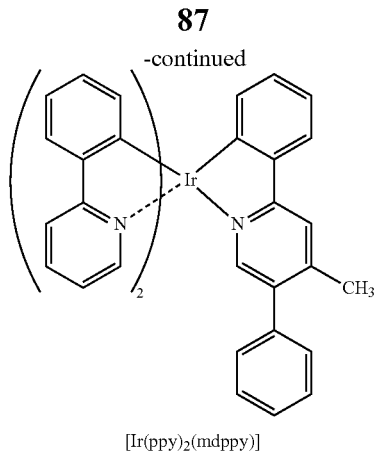

[Ir(ppy)₂(mdppy)]

<<Operation Characteristics of Each Light-Emitting Element>>

Operation characteristics of the fabricated light-emitting element 6, the comparative light-emitting element 7, and the comparative light-emitting element 8 were measured. Note that the measurement was carried out at room temperature (an atmosphere maintained at 25° C.).

The current density-luminance characteristics, the voltage-luminance characteristics, the luminance-current efficiency characteristics, and the voltage-current characteristics of each light-emitting element are shown in FIG. 27, FIG. 28, FIG. 29, and FIG. 30, respectively.

Table 6 below shows initial values of main characteristics of each of the light-emitting elements at around 1000 cd/m².

light-emitting element 7 which used the comparative organic compound, 8DBt-4mDBtBPBfpm, and the comparative light-emitting element 8 which used the comparative organic compound, 8mDBtP-4mDBtBPBfpm. This is owing to the effect of the organic compound of one embodiment of the present invention, 8Ph-4mDBtBPBfpm, having a phenyl group at the 8-position of a benzofuropyrimidine skeleton. From the above facts, in order to suppress initial degradation, introducing an unsubstituted phenyl group at the 8-position of a benzofuropyrimidine skeleton is important. Thus, it is useful to use the organic compound of one embodiment of the present invention in improving reliability of the light-emitting element.

Reference Synthesis Example 1

In this reference synthesis example, a specific example of synthesizing the organic compound represented by the structural formula below and used for the comparative light-emitting element 7 of this example, 8-(dibenzothiophen-4-yl)-4-[3'-(dibenzothiophen-4-yl)biphenyl-3-yl]-[1]benzofuro[3,2-d]pyrimidine (abbreviation: 8DBt-4mDBtBPBfpm) (Structural Formula (300)), will be described.

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 6 | 3.4 | 0.052 | 0.3 | (0.35, 0.62) | 990 | 76 | 70 | 21 |
| Comparative light-emitting element 7 | 3.6 | 0.051 | 1.3 | (0.35, 0.61) | 910 | 71 | 62 | 20 |
| Comparative light-emitting element 8 | 3.6 | 0.062 | 1.6 | (0.34, 0.62) | 1000 | 66 | 58 | 18 |

Figure 31:
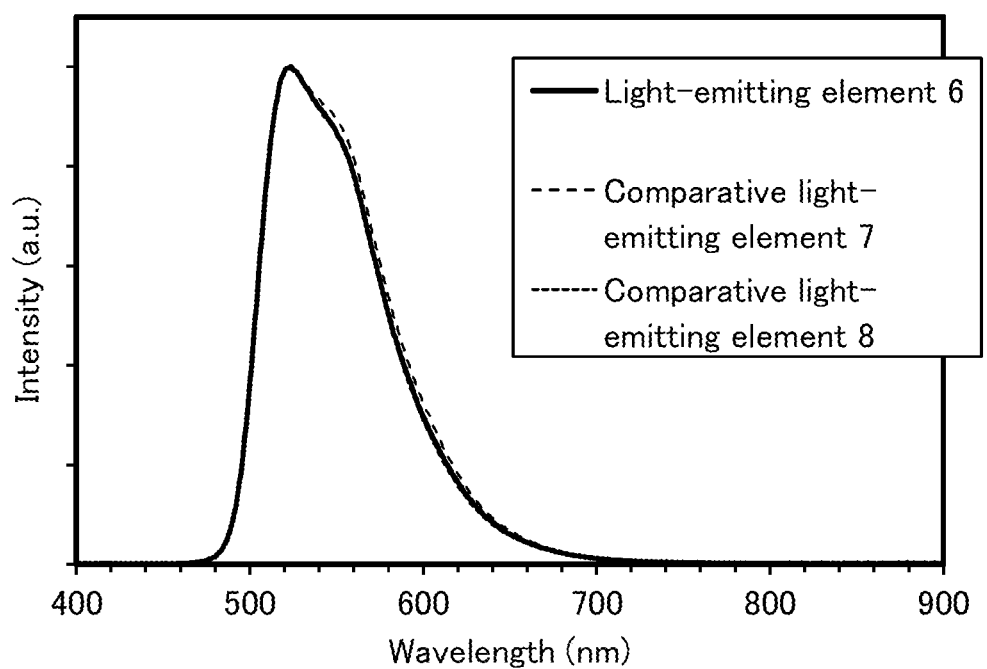
FIG. 31 is a graph showing emission spectra of the light-emitting element 6, the comparative light-emitting element 7, and the comparative light-emitting element 8.

FIG. 31 shows emission spectra of the case where current at a current density of 2.5 mA/cm² was supplied to the light-emitting element 6, the comparative light-emitting element 7, and the comparative light-emitting element 8. As shown in FIG. 31, the emission spectra of the light-emitting elements have peaks at around 523 nm, and it is suggested that the peaks are derived from light emission of [Ir(ppy)₂(mdppy)] contained in the light-emitting layer 913.

Figure 32:
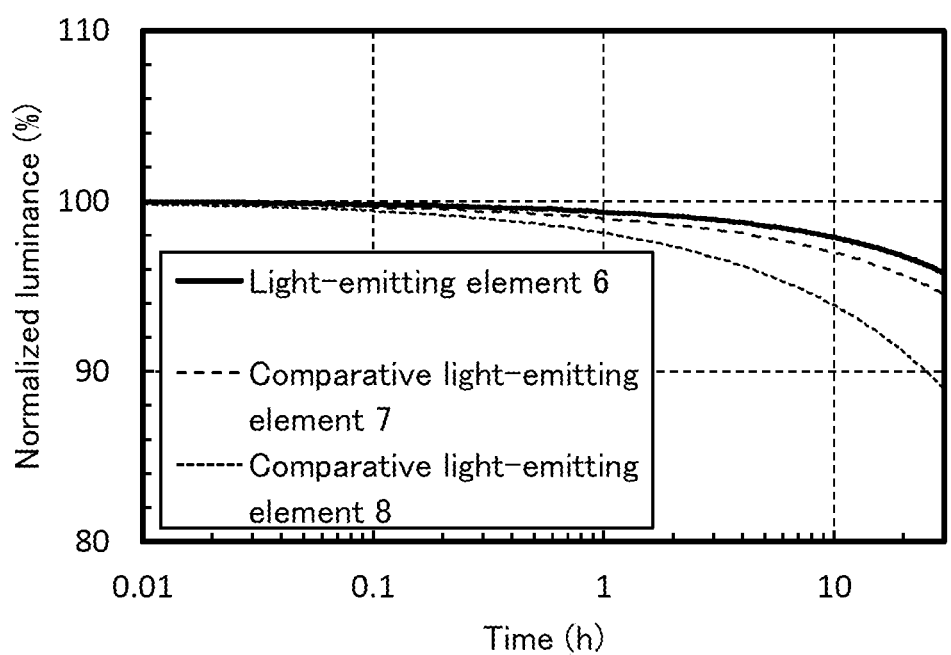
FIG. 32 is a graph showing reliability of the light-emitting element 6, the comparative light-emitting element 7, and the comparative light-emitting element 8.

Next, reliability tests were performed on the light-emitting element 6, the comparative light-emitting element 7, and the comparative light-emitting element 8. FIG. 32 shows the results of the reliability tests. In FIG. 32, the vertical axis represents normalized luminance (%) with an initial luminance of 100%, and the horizontal axis represents driving time (h) of the elements. As the reliability tests, constant current driving tests where a constant current was supplied at a current density of 50 mA/cm² were performed.

The results of the reliability tests show that the light-emitting element 6 which used the organic compound of one embodiment of the present invention, 8Ph-4mDBtBPBfpm, had a suppressed initial degradation compared with the

[Chemical Formula 36]

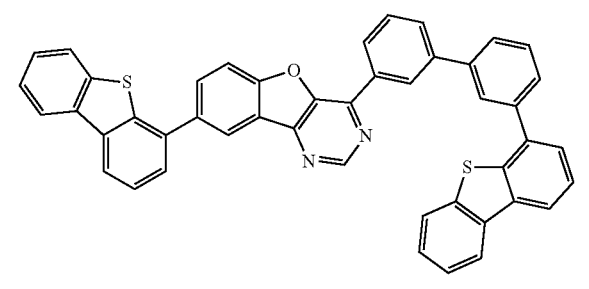

8DBt-4mDBtBPBfpm (300)

Into a three-neck flask, 7.00 g of 8-chloro-4-[3'-(dibenzothiophen-4-yl)biphenyl-3-yl]-[1]benzofuro[3,2-d]pyrimidine, 3.56 g of dibenzothiophene-4-boronic acid, 0.281 g of 2'-(dicyclohexylphosphino)acetophenone ethylene ketal, 6.00 g of cesium fluoride, and 65 mL of mesitylene were put, they were degassed by being stirred under reduced pressure, and the air was replaced with nitrogen.

To this mixture, 0.359 g of tris(dibenzylideneacetone)dipalladium(0) (Pd$_2$(dba)$_3$) was added, followed by stirring at 120° C. for 1 hour. To this mixture, 65 mL of degassed mesitylene was added, and stirring was performed at 120° C. for 9.5 hours. Furthermore, 30 mL of degassed mesitylene was added to the mixture and stirring was performed at 120° C. for 7 hours. To this mixture, 0.360 g of Pd$_2$(dba)$_3$ and 0.284 g of 2'-(dicyclohexylphosphino)acetophenone ethylene ketal were added, and stirring was performed at 130° C. for 15 hours, and then at 140° C. for 6 hours.

To this mixture, 2.37 g of dibenzothiophene-4-boronic acid, 0.359 g of Pd$_2$(dba)$_3$, and 0.283 g of 2'-(dicyclohexylphosphino)acetophenone ethylene ketal were added, and stirring was performed at 140° C. for 40 hours. Water was added to the obtained reaction substance, suction filtration was performed, and the resulting residue was washed with water and ethyl acetate. This residue was dissolved in heated toluene, followed by filtration through a filter aid filled with Celite, alumina, and Celite in this order. The obtained solution was concentrated and dried, and then recrystallized with toluene to give 5.56 g of a target substance (yield: 62%, white solid).

By a train sublimation method, 1.95 g of this white solid was sublimated and purified. The conditions of the sublimation purification were such that the solid was heated under a pressure of 2.8 Pa at 355° C. while the argon gas was made to flow at a flow rate of 15 mL/min. After the purification by sublimation, 1.46 g of a target pale brown substance was obtained at a collection rate of 75%. The synthesis scheme is shown in the following formula (e-1).

[Chemical Formula 37]

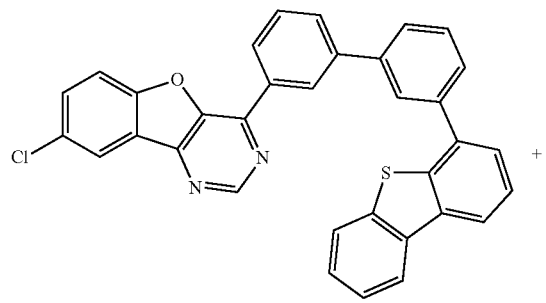

(e-1)

+

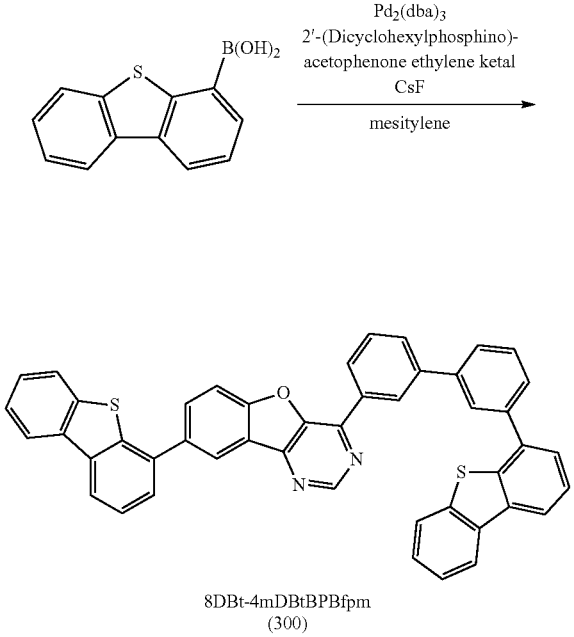

8DBt-4mDBtBPBfpm
(300)

Analysis results by nuclear magnetic resonance ($^1$H-NMR) spectroscopy of the pale brown solid obtained as described above are shown below. It was found that 8DBt-4mDBtBPBfpm was obtained.

$^1$H-NMR. δ (CDCl$_3$): 7.47-7.51 (m, 4H), 7.59-7.65 (m, 4H), 7.70 (t, 1H), 7.76-7.87 (m, 6H), 7.95 (d, 1H), 8.09 (d, 1H), 8.21-8.24 (m, 5H), 8.66-8.68 (m, 2H), 9.01 (s, 1H), 9.34 (s, 1H).

Reference Synthesis Example 2

In this reference synthesis example, a specific example of synthesizing the organic compound represented by the structural formula below and used for the comparative light-emitting element 8 of this example, 4-[3'-(dibenzothiophen-4-yl)biphenyl-3-yl]-8-[3-(dibenzothiophen-4-yl)phenyl]-[1]benzofuro[3,2-d]pyrimidine (abbreviation: 8mDBtP-4mDBtBPBfpm) (Structural Formula (301)), will be described.

[Chemical Formula 38]

(301)

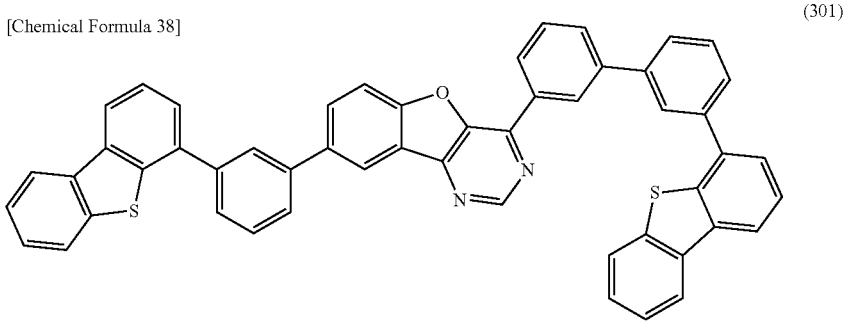

8mDBtP-4mDBtBPBfpm

Into a three-neck flask, 1.23 g of 8-chloro-4-[3'-(dibenzothiophen-4-yl)biphenyl-3-yl]-[1]benzofuro[3,2-d]pyrimidine, 0.837 g of 3-(dibenzothiophene-4-yl)phenylboronic acid, 49.2 mg of 2'-(dicyclohexylphosphino)acetophenone ethylene ketal, 1.03 g of cesium fluoride, and 30 mL of mesitylene were put, they were degassed by being stirred under reduced pressure, and the air was replaced with nitrogen.

To this mixture, 63.2 mg of tris(dibenzylideneacetone)dipalladium(0) (Pd$_2$(dba)$_3$) was added, and stirring was performed at 100° C. for 20.5 hours. To this mixture, 49.1 mg of 2'-(dicyclohexylphosphino)acetophenone ethylene ketal and 63.0 mg of Pd$_2$(dba)$_3$ were added, followed by stirring at 120° C. for 23 hours. Furthermore, 52.3 mg of 2'-(dicyclohexylphosphino)acetophenone ethylene ketal and 62.4 mg of Pd$_2$(dba)$_3$ were added to this mixture, and stirring was performed at 140° C. for 21 hours.

Water was added to the obtained reaction substance, suction filtration was performed, and the resulting residue was washed with water and ethyl acetate. This residue was dissolved in heated toluene, followed by filtration through a filter aid filled with Celite, alumina, and Celite in this order. The obtained solution was concentrated and dried, and then recrystallized with toluene to give 0.70 g of a target substance (yield: 40%, white solid).

By a train sublimation method, 0.70 g of this white solid was sublimated and purified. The conditions of the sublimation purification were such that the solid was heated under a pressure of 2.8 Pa at 375° C. while the argon gas was made to flow at a flow rate of 10 mL/min. After the purification by sublimation, 0.54 g of a target yellowish white solid was obtained at a collection rate of 77%. The synthesis scheme is shown in the following formula (f-1).

Analysis results by nuclear magnetic resonance ($^1$H-NMR) spectroscopy of the yellowish white solid obtained as described above are shown below. It was found that 8mDBtP-4mDBtBPBfpm was obtained.

$^1$H-NMR. δ (CDCl$_3$): 7.45-7.52 (m, 4H), 7.59-7.63 (m, 4H), 7.76-7.70 (m, 2H), 7.75 (t, 1H), 7.79-7.82 (m, 5H), 7.85 (d, 1H), 7.87-7.89 (m, 1H), 8.02 (d, 1H), 8.10 (s, 1H), 8.19-8.23 (m, 5H), 8.62 (s, 1H), 8.65 (d, 1H), 8.98 (s, 1H), 9.32 (s, 1H).

Example 8

Synthesis Example 5

In this example, a synthesis method of 5-[3-(8-phenyl[1]benzofuro[3,2-d]pyrimidin-4-yl)phenyl]-5H-[1]benzothieno[3,2-c]carbazole (abbreviation: 8Ph-4mBTczPBfpm), which is an organic compound of one embodiment of the present invention represented by Structural Formula (117) in Embodiment 1, will be described. Note that the structure of 8Ph-4mBTczPBfpm is shown below.

[Chemical Formula 39]

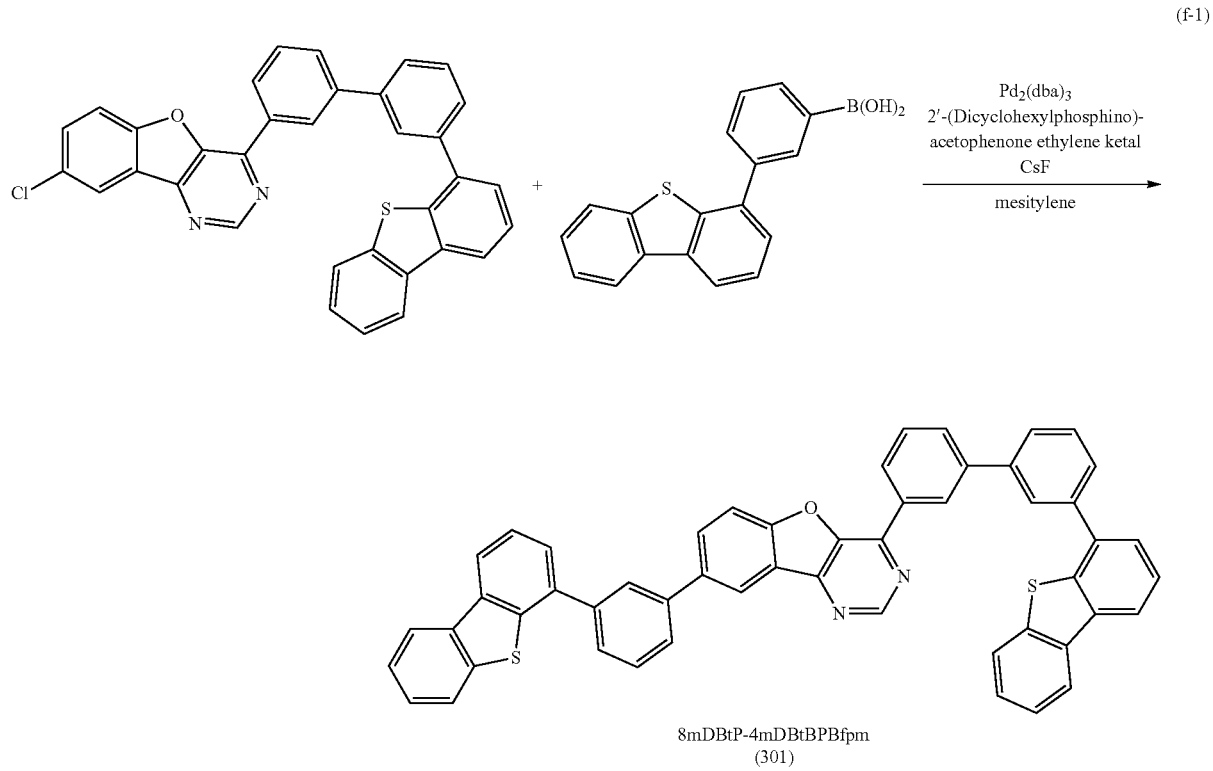

(f-1)

8mDBtP-4mDBtBPBfpm
(301)

[Chemical Formula 40]

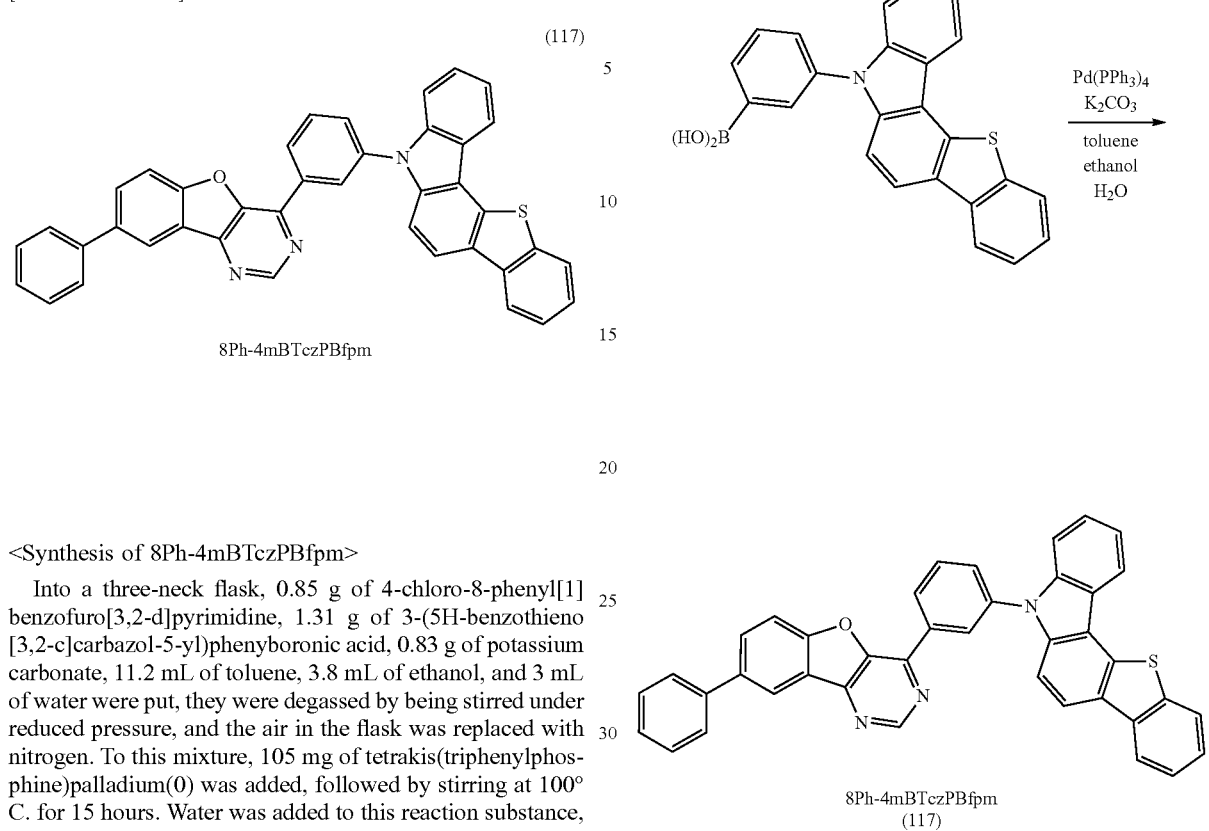

(117)

8Ph-4mBTczPBfpm

<Synthesis of 8Ph-4mBTczPBfpm>

Into a three-neck flask, 0.85 g of 4-chloro-8-phenyl[1]benzofuro[3,2-d]pyrimidine, 1.31 g of 3-(5H-benzothieno[3,2-c]carbazol-5-yl)phenylboronic acid, 0.83 g of potassium carbonate, 11.2 mL of toluene, 3.8 mL of ethanol, and 3 mL of water were put, they were degassed by being stirred under reduced pressure, and the air in the flask was replaced with nitrogen. To this mixture, 105 mg of tetrakis(triphenylphosphine)palladium(0) was added, followed by stirring at 100° C. for 15 hours. Water was added to this reaction substance, suction filtration was performed, and the resulting residue was washed with water, ethanol, and toluene. The obtained residue was dissolved in heated toluene, followed by filtration through a filter aid filled with Celite, alumina, and Celite in this order. The obtained solution was concentrated and dried, and then recrystallized with toluene to give 1.35 g of a target yellow solid in a yield of 75%.

By a train sublimation method, 1.16 g of the obtained yellow solid was sublimated and purified. The conditions of the sublimation purification were such that the solid was heated under a pressure of 2.61 Pa at 310° C. while the argon gas was made to flow at a flow rate of 10 mL/min. After the purification by sublimation, 0.95 g of a target yellow substance was obtained at a collection rate of 82%. This synthesis scheme is shown in the following formula (g-1).

[Chemical Formula 41]

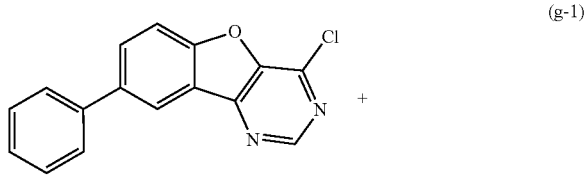

(g-1)

Figure 33:
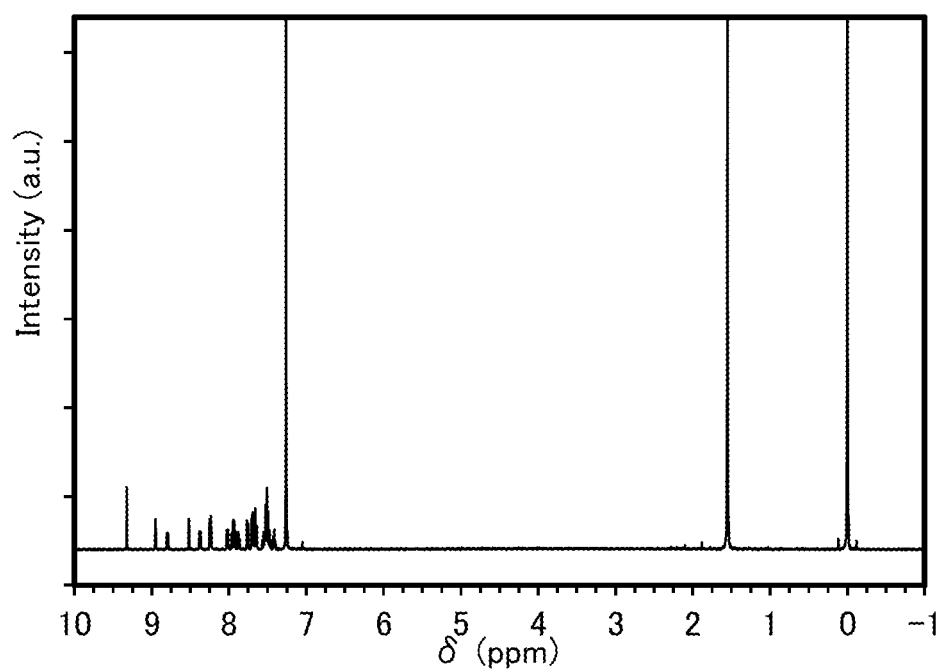
FIG. 33 is a $^1$H-NMR chart of an organic compound represented by Structural Formula (117).
Figure 34:
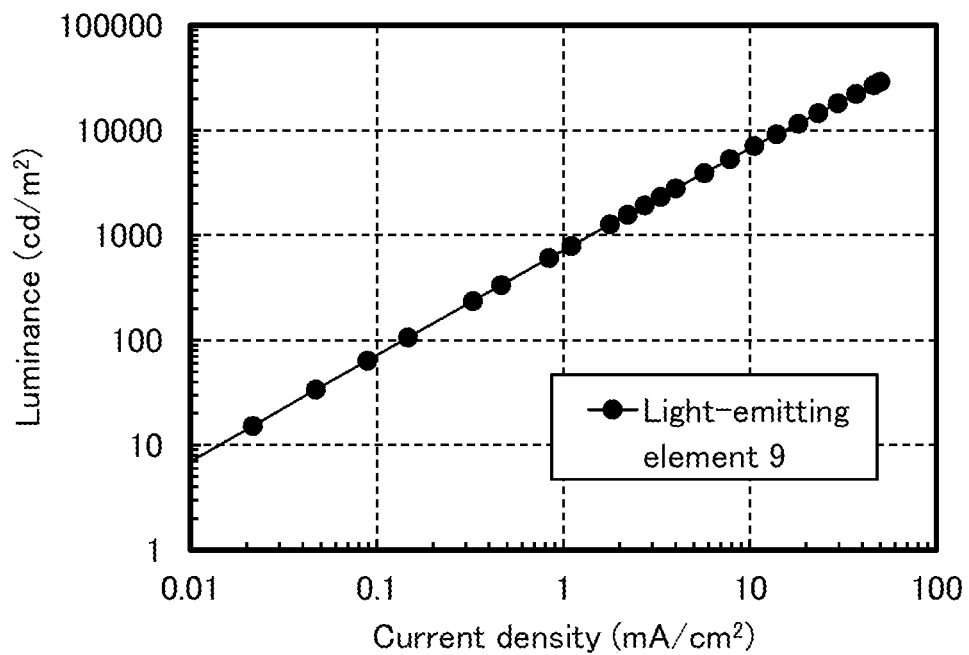
FIG. 34 is a graph showing current density-luminance characteristics of a light-emitting element 9.
Figure 35:
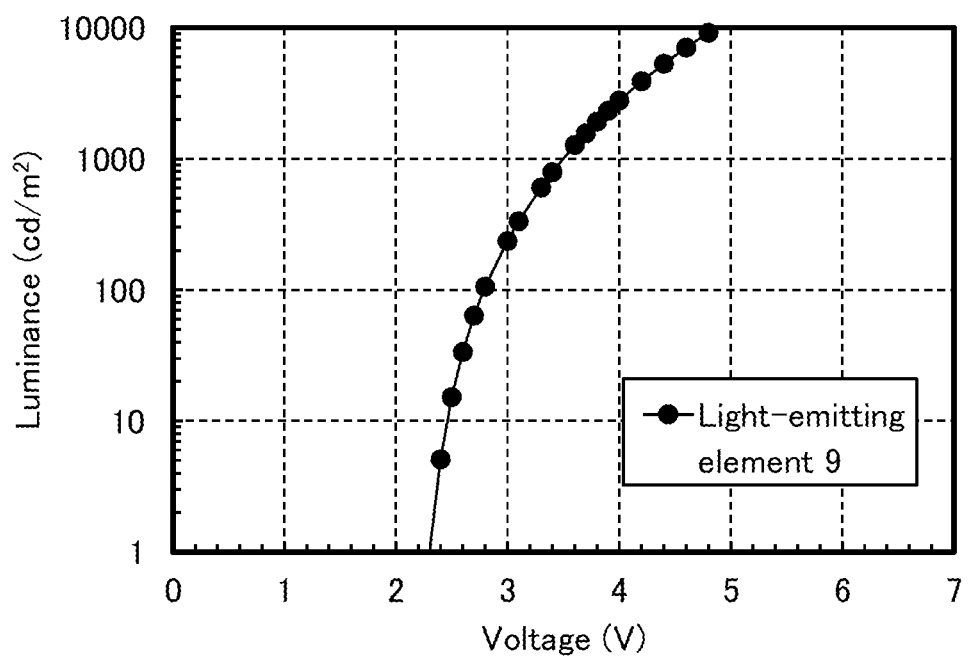
FIG. 35 is a graph showing voltage-luminance characteristics of the light-emitting element 9.
Figure 36:
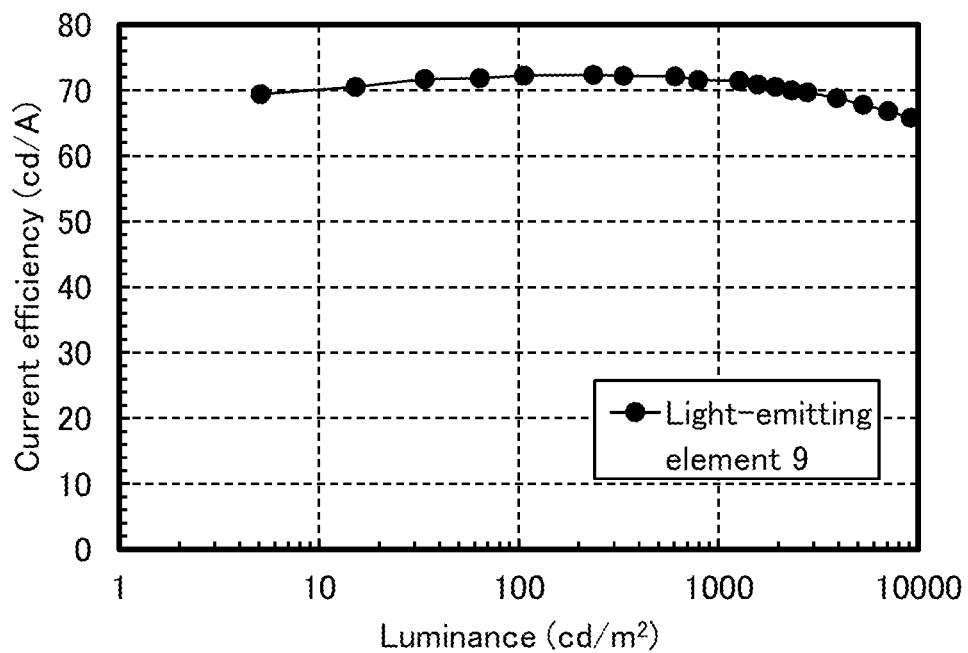
FIG. 36 is a graph showing luminance-current efficiency characteristics of the light-emitting element 9.
Figure 37:
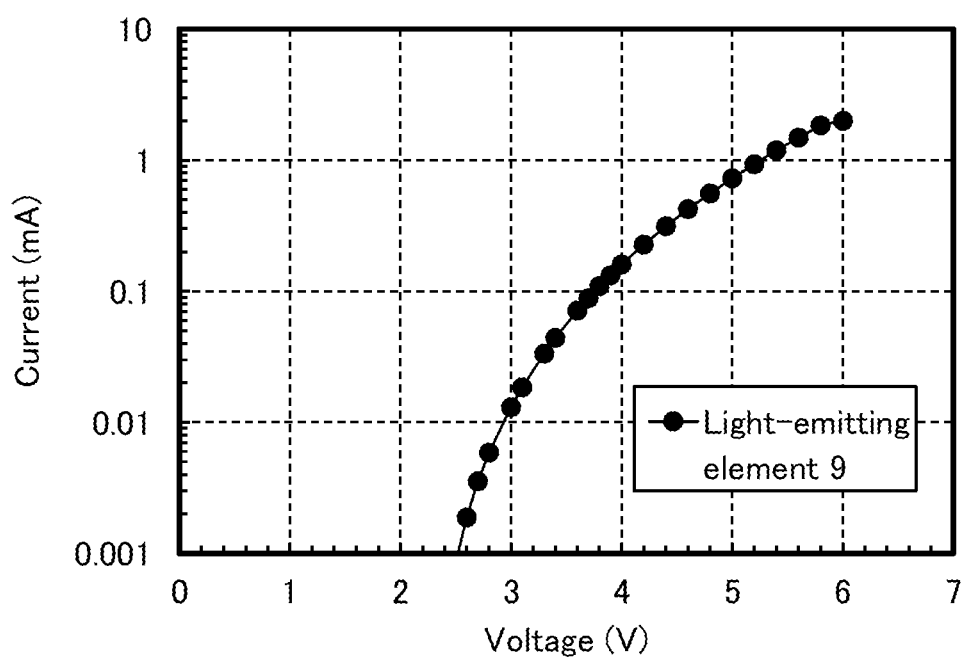
FIG. 37 is a graph showing voltage-current characteristics of the light-emitting element 9.

Analysis results by nuclear magnetic resonance (H-NMR) spectroscopy of the yellow solid obtained in the above-described reaction are shown below. FIG. 33 shows a H-NMR chart. The results reveal that 8Ph-4mBTczPBfpm, the above-described organic compound of one embodiment of the present invention represented by Structural Formula (117), was obtained in this example.

$^1$H-NMR. δ (CDCl$_3$): 9.32 (s, 1H), 8.95 (s, 1H), 8.80 (d, 1H), 8.52 (s, 1H), 8.38 (d, 1H), 8.24 (d, 2H), 8.02 (d, 1H), 7.97-7.92 (m, 2H), 7.87 (d, 1H), 7.76 (d, 1H), 7.71-7.64 (m, 4H), 7.57-7.46 (m, 6H), 7.41 (t, 1H).

Example 9

In this example, a light-emitting element 9, which is the light-emitting element of one embodiment of the present invention and uses 8Ph-2,4DBf2Bfpm (Structural Formula (200)) described in Example 4, PCCP, and [Ir(ppy)$_2$(mdppy)] in its light-emitting layer, was fabricated and the measured characteristics of the light-emitting element are shown.

Note that the element structure of the light-emitting element 9 fabricated in this example is similar to that in FIG. 14 mentioned in Example 5, and the specific composition of each layer of the element structure is as shown in Table 7. Chemical formulae of materials used in this example are shown below.

TABLE 7
| | First electrode | Hole-injection layer | Hole-transport layer | Light-emitting layer | Electron-transport layer | | Electron-injection layer | Second electrode |
|---|---|---|---|---|---|---|---|---|
| Light-emitting element 9 | ITSO (70 nm) | DBT3P-II:MoOx (2:1 45 nm) | PCBBi1BP (20 nm) | * | 8Ph-2,4DBf2Bfpm (20 nm) | NBphen (10 nm) | LiF (1 nm) | Al (200 nm) |
* 8Ph-2,4DBf2Bfpm:PCCP:[Ir(ppy)2(mdppy)] (0.5:0.5:0.1 40 nm)
[Chemical Formula 42]
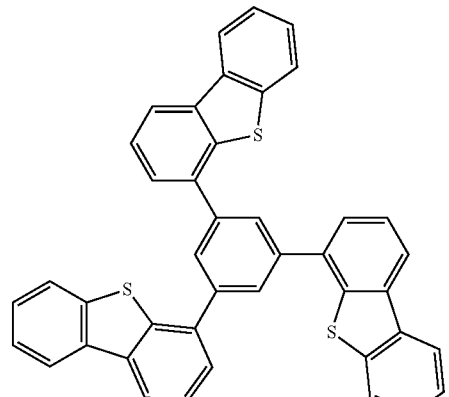
DBT3P-II
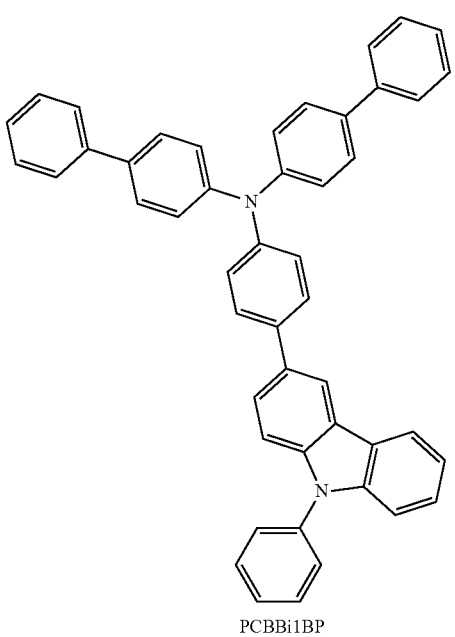
PCBBi1BP
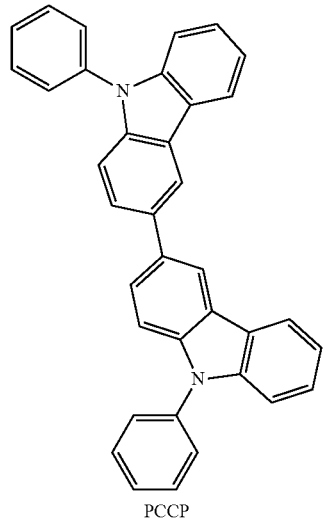
PCCP
(200)
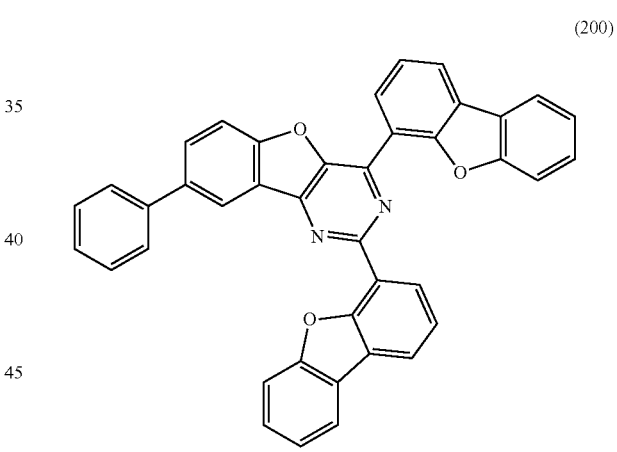
8Ph-2,4DBf2Bfpm
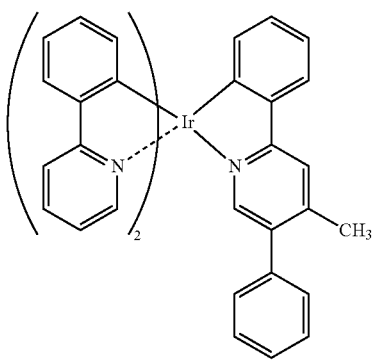
[Ir(ppy)₂(mdppy)]

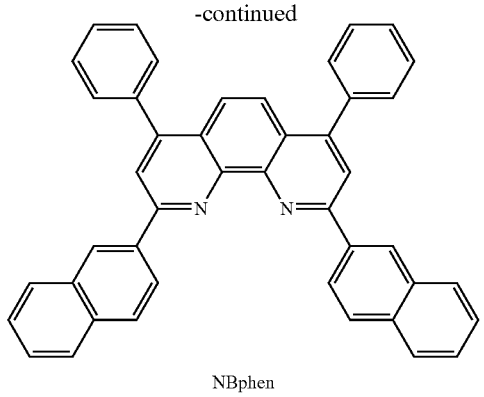

NBphen

<<Operation Characteristics of Light-Emitting Element 9>>

Operation characteristics of the fabricated light-emitting element 9 were measured. Note that the measurement was carried out at room temperature (an atmosphere maintained at 25° C.).

The current density-luminance characteristics, the voltage-luminance characteristics, the luminance-current efficiency characteristics, and the voltage-current characteristics of the light-emitting element 9 are shown in FIG. 34, FIG. 35, FIG. 36, and FIG. 37, respectively.

Table 8 below shows initial values of main characteristics of the light-emitting element 9 at around 1000 cd/m$^2$.

TABLE 8

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 9 | 3.4 | 0.044 | 1.1 | (0.37, 0.60) | 790 | 72 | 66 | 20 |

Figure 38:
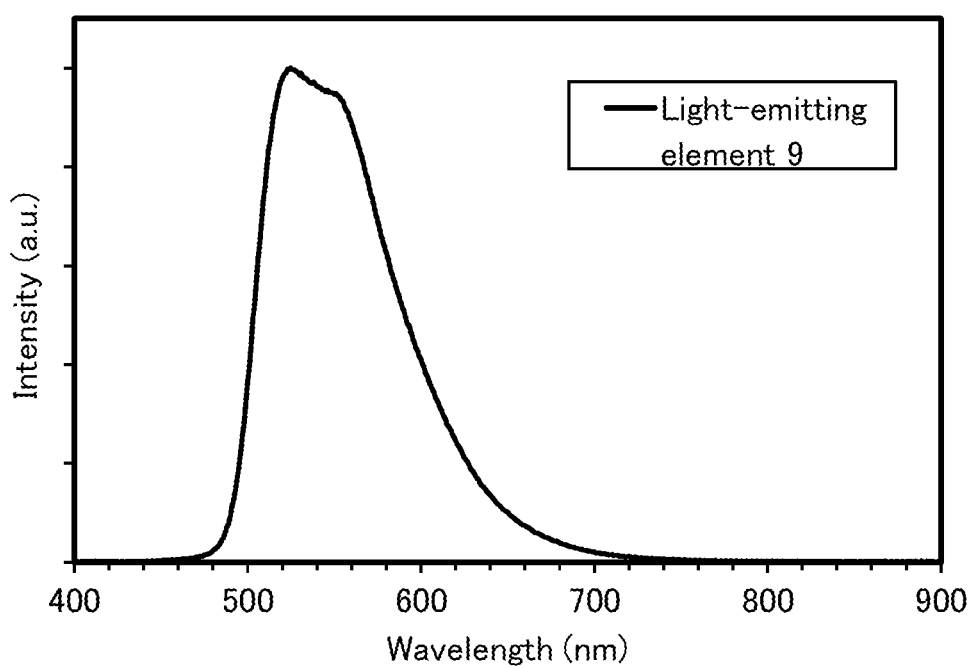
FIG. 38 is a graph showing an emission spectrum of the light-emitting element 9.

FIG. 38 shows emission spectra of the case where current at a current density of 2.5 mA/cm$^2$ was supplied to each light-emitting element. As shown in FIG. 38, the emission spectra of the light-emitting element 9 have peaks at around 525 nm, and it is suggested that the peaks are derived from light emission of [Ir(ppy)$_2$(mdppy)] contained in the light-emitting layer 913.

REFERENCE NUMERALS

101: first electrode, 102: second electrode, 103: EL layer, 103a, 103b: EL layer, 104, 104a, 104b: charge-generation layers, 111, 111, 111b: hole-injection layers, 112, 112a, 112b: hole-transport layers, 113, 113a, 113b, 113c: light-emitting layers, 114, 114a, 114b: electron-transport layers, 115, 115a, 115b: electron-injection layers, 200R, 200G, 200B: optical path lengths, 201: first substrate, 202: transistor (FET), 203R, 203G, 203B, 203W: light-emitting elements, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuits), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: steering wheel, 5106: shifter, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7014: antenna, 7015: shutter button, 7016: image receiving portion, 7018: stand, 7021: external connection portion, 7022, 7023: operation buttons, 7024: connection terminal, 7025: band, 7026: microphone, 7027: icon indicating time, 7028: another icon, 7029: sensor, 7030: speaker, 7052, 7053, 7054: information, 9310: portable information terminal, 9311: display portion, 9312: display region, 9313: hinge, 9315: housing This application is based on Japanese Patent Application Serial No. 2018-104892 filed with Japan Patent Office on May 31, 2018, the entire contents of which are hereby incorporated herein by reference.

The invention claimed is:

1. An organic compound represented by General Formula (G1):

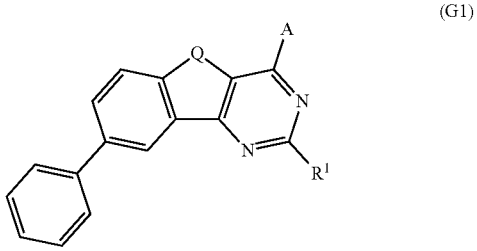

(G1)

wherein Q represents oxygen or sulfur, wherein A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure, wherein R$^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms, and wherein, when the substituted or unsubstituted monocyclic saturated hydrocarbon having 5 to 7 carbon atoms, the substituted or unsubstituted polycyclic saturated hydrocarbon having 7 to 10 carbon atoms, the substituted or unsubstituted aryl group having 6 to 13 carbon atoms, or the substituted or unsubstituted heteroaryl group having 3 to 12 carbon atoms in the $R^1$ comprises a substituent, the substituent comprises at least one of an alkyl group having 1 to 7 carbon atoms, a cycloalkyl group having 5 to 7 carbon atoms, and an aryl group having 6 to 12 carbon atoms.

2. An organic compound represented by General Formula (G2):

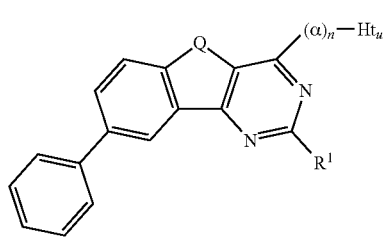

(G2)

wherein Q represents oxygen or sulfur, wherein α represents a substituted or unsubstituted phenylene group, wherein n represents an integer of 0 to 4, wherein $Ht_{uni}$ represents a skeleton having a hole-transport property, and wherein $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

3. The organic compound according to claim 2, wherein the organic compound is represented by General Formula (G3):

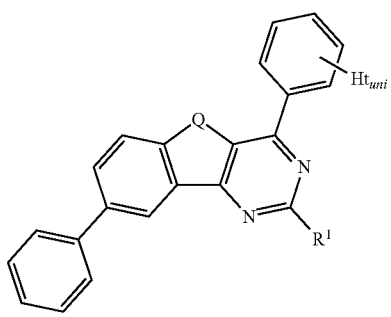

(G3)

4. The organic compound according to claim 2, wherein the organic compound is represented by General Formula (G4):

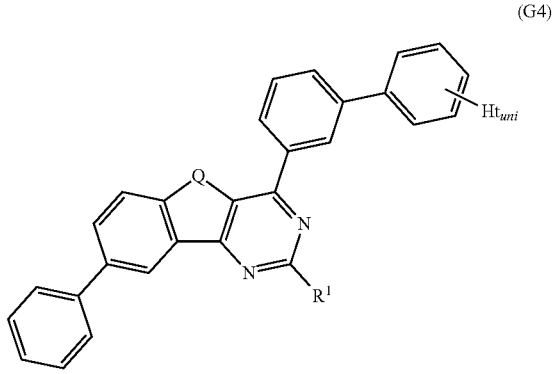

(G4)

5. The organic compound according to claim 2, wherein the $Ht_{uni}$ has any one of a pyrrole ring structure, a furan ring structure, or a thiophene ring structure.

6. The organic compound according to claim 2, wherein the $Ht_{uni}$ is represented by any one of General Formulae (Ht-1) to (Ht-26) below:

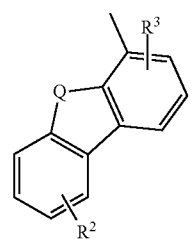

(Ht-1)

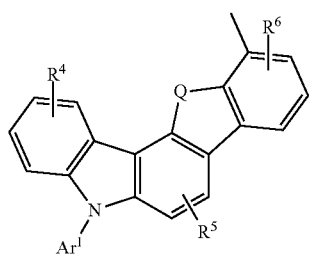

(Ht-2)

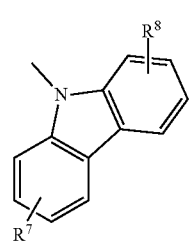

(Ht-3)

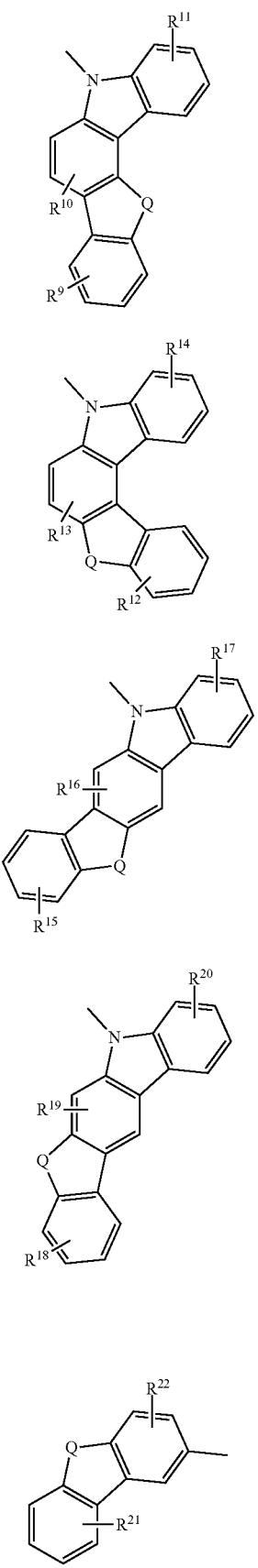
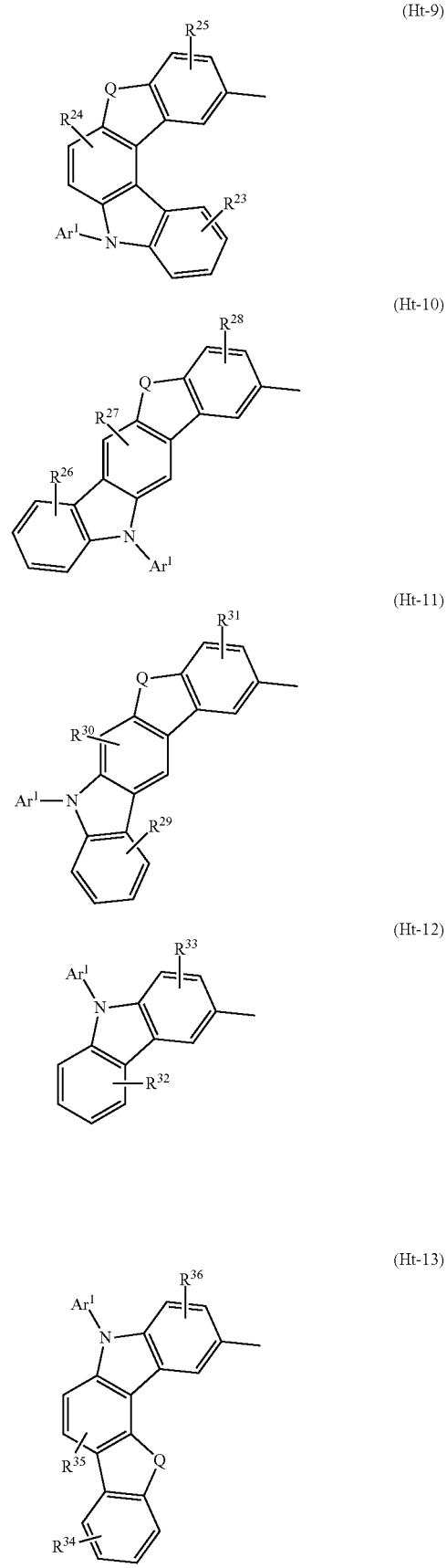

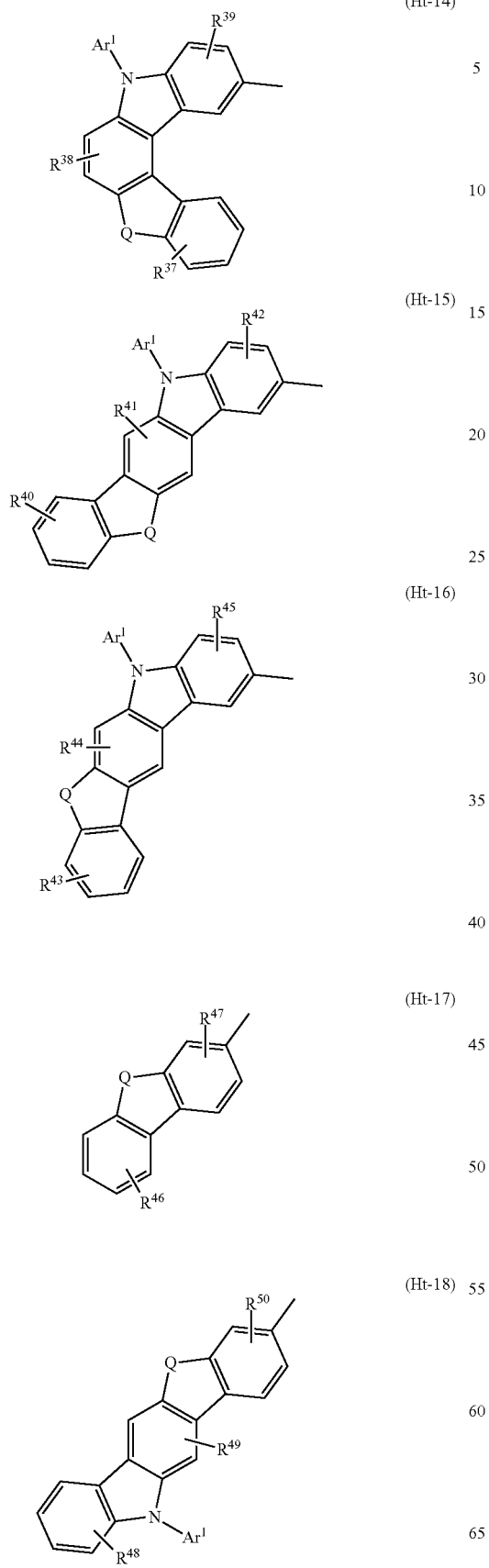
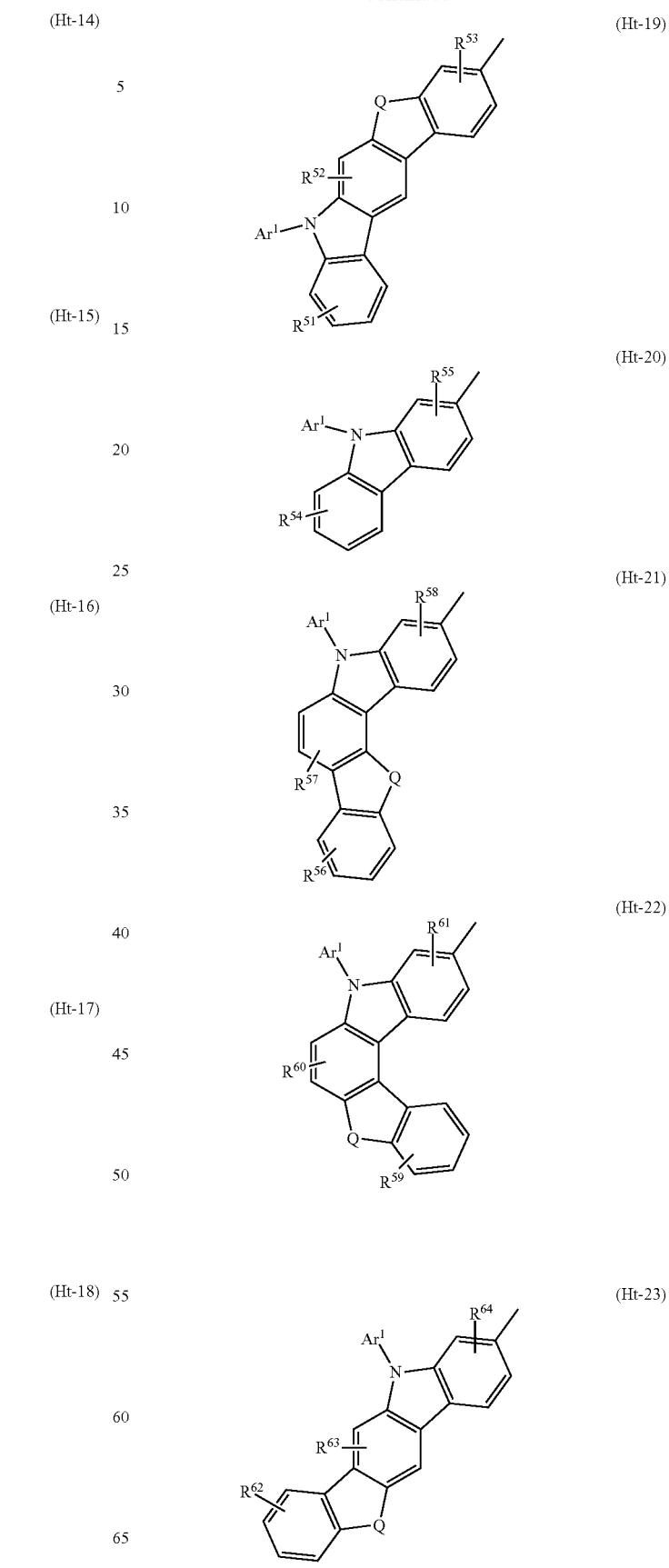

(Ht-24)

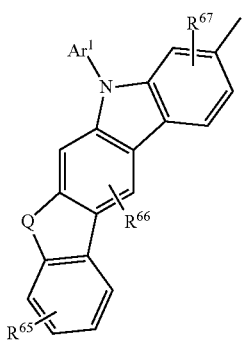

(Ht-25)

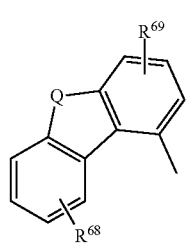

(Ht-26)

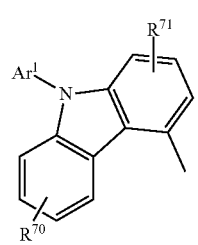

wherein Q represents oxygen or sulfur, wherein $R^2$ to $R^{71}$ each represent 1 to 4 substituents and each independently represent any one of hydrogen, an alkyl group having 1 to 6 carbon atoms, and a substituted or unsubstituted phenyl group, and wherein $Ar^1$ represents a substituted or unsubstituted aryl group having 6 to 13 carbon atoms.

7. An organic compound represented by any one of Structural Formulae (100), (101), (102), (117), and (200):

(100)

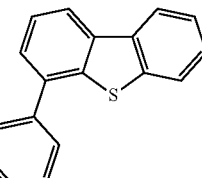

(101)

(102)

(200)

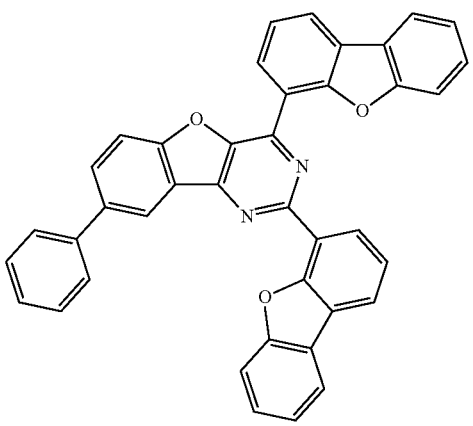

(117)

8. A light-emitting element using the organic compound according to claim 1.

9. A light-emitting element comprising an EL layer between a pair of electrodes,
   wherein the EL layer comprises the organic compound according to claim 1.

10. A light-emitting element comprising an EL layer between a pair of electrodes,
    wherein the EL layer comprises a light-emitting layer, and
    wherein the light-emitting layer comprises the organic compound according to claim 1.

11. A light-emitting element comprising an EL layer between a pair of electrodes,
    wherein the EL layer comprises a light-emitting layer, and
    wherein the light-emitting layer comprises the organic compound according to claim 1, and a phosphorescent material.

12. A light-emitting element comprising an EL layer between a pair of electrodes,
    wherein the EL layer comprises a light-emitting layer, and
    wherein the light-emitting layer comprises the organic compound according to claim 1, a phosphorescent material, and a carbazole derivative.

13. A light-emitting element according to claim 12,
    wherein the carbazole derivative is a bicarbazole derivative.

14. A light-emitting device comprising:
    the light-emitting element according to claim 8; and
    at least one of a transistor and a substrate.

15. An electronic device comprising:
    the light-emitting device according to claim 14; and
    at least one of a microphone, a camera, an operation button, an external connection portion, and a speaker.

16. A lighting device comprising:
    the light-emitting element according to claim 8; and
    at least one of a housing, a cover, and a support base.

17. A light-emitting element using the organic compound according to claim 2.

18. A light-emitting element comprising an EL layer between a pair of electrodes,
    wherein the EL layer comprises a light-emitting layer, and
    wherein the light-emitting layer comprises the organic compound according to claim 2.

19. A light-emitting element comprising an EL layer between a pair of electrodes,
    wherein the EL layer comprises a light-emitting layer, and
    wherein the light-emitting layer comprises the organic compound according to claim 2, a phosphorescent material, and a carbazole derivative.

20. A light-emitting element according to claim 19,
    wherein the carbazole derivative is a bicarbazole derivative.

21. The organic compound according to claim 2,
    wherein, when the substituted or unsubstituted monocyclic saturated hydrocarbon having 5 to 7 carbon atoms, the substituted or unsubstituted polycyclic saturated hydrocarbon having 7 to 10 carbon atoms, the substituted or unsubstituted aryl group having 6 to 13 carbon atoms, or the substituted or unsubstituted heteroaryl group having 3 to 12 carbon atoms in the R1 comprises a substituent, the substituent comprises at least one of an alkyl group having 1 to 7 carbon atoms, a cycloalkyl group having 5 to 7 carbon atoms, and an aryl group having 6 to 12 carbon atoms.

* * * * *